(12) United States Patent
O'Neil et al.

(10) Patent No.: US 12,351,619 B2
(45) Date of Patent: Jul. 8, 2025

(54) SERUM ALBUMIN-BINDING FIBRONECTIN TYPE III DOMAINS AND USES THEREOF

(71) Applicant: ARO BIOTHERAPEUTICS COMPANY, Philadelphia, PA (US)

(72) Inventors: Karyn O'Neil, Philadelphia, PA (US); Yao Xin, Philadelphia, PA (US); Russell C. Addis, Philadelphia, PA (US)

(73) Assignee: ARO Biotherapeutics Company, Philadelphia, PA (US)

( * ) Notice: Subject to any disclaimer, the term of this patent is extended or adjusted under 35 U.S.C. 154(b) by 651 days.

(21) Appl. No.: 17/786,786

(22) PCT Filed: Dec. 18, 2020

(86) PCT No.: PCT/US2020/065878
§ 371 (c)(1),
(2) Date: Jun. 17, 2022

(87) PCT Pub. No.: WO2021/127353
PCT Pub. Date: Jun. 24, 2021

(65) Prior Publication Data
US 2023/0039851 A1    Feb. 9, 2023

Related U.S. Application Data

(60) Provisional application No. 62/949,856, filed on Dec. 18, 2019.

(51) Int. Cl.
C07K 14/765    (2006.01)
C07K 14/78    (2006.01)
C12N 15/63    (2006.01)
G01N 33/49    (2006.01)

(52) U.S. Cl.
CPC ............ *C07K 14/765* (2013.01); *C07K 14/78* (2013.01); *C12N 15/63* (2013.01); *G01N 33/49* (2013.01); *C07K 2319/21* (2013.01); *C07K 2319/55* (2013.01); *C07K 2319/70* (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,560,655 A | 12/1985 | Baker |
| 4,657,866 A | 4/1987 | Kumar |
| 4,767,704 A | 8/1988 | Cleveland et al. |
| 4,927,762 A | 5/1990 | Darfler |
| 5,122,469 A | 6/1992 | Mather et al. |
| 5,223,409 A | 6/1993 | Ladner et al. |
| 5,643,768 A | 7/1997 | Kawasaki |
| 5,856,456 A | 1/1999 | Whitlow et al. |
| 6,172,197 B1 | 1/2001 | McCafferty et al. |
| 6,472,147 B1 | 10/2002 | Janda et al. |
| 6,582,915 B1 | 6/2003 | Griffiths et al. |
| 6,673,901 B2 | 1/2004 | Koide |
| 6,969,108 B2 | 11/2005 | Fukumoto et al. |
| 7,842,476 B2 | 11/2010 | McGregor et al. |
| 8,278,419 B2 | 10/2012 | Jacobs et al. |
| 8,569,227 B2 | 10/2013 | Jacobs |
| 9,644,023 B2 | 5/2017 | Torres et al. |
| 10,662,235 B2 | 5/2020 | Anderson et al. |
| 10,925,932 B2 | 2/2021 | Diem et al. |
| 2004/0253247 A1 | 12/2004 | Dennis et al. |
| 2005/0287153 A1 | 12/2005 | Dennis |
| 2010/0216708 A1 | 8/2010 | Jacobs et al. |
| 2011/0118144 A1 | 5/2011 | Hyun et al. |
| 2011/0274623 A1 | 11/2011 | Jacobs |
| 2013/0079243 A1 | 3/2013 | Diem et al. |
| 2013/0226834 A1 | 8/2013 | Gannalo, II |
| 2015/0152147 A1 | 6/2015 | Gosselin et al. |
| 2015/0210756 A1 | 7/2015 | Torres et al. |
| 2016/0041182 A1 | 2/2016 | Diem et al. |
| 2017/0174748 A1 | 6/2017 | Mitchell et al. |
| 2017/0348397 A1 | 12/2017 | Diem et al. |
| 2019/0127444 A1 | 5/2019 | Brezski et al. |
| 2019/0256575 A1 | 8/2019 | Chen et al. |
| 2019/0263915 A1 | 8/2019 | Goldberg et al. |
| 2019/0330361 A1 | 10/2019 | Chin et al. |
| 2021/0228688 A1 | 7/2021 | Diem et al. |

FOREIGN PATENT DOCUMENTS

| | | |
|---|---|---|
| CN | 102307896 A | 1/2012 |
| CN | 103002923 A | 3/2013 |
| CN | 103827361 A | 5/2014 |
| CN | 104955473 A | 9/2015 |
| JP | 2012507295 A | 3/2012 |
| WO | 1987000195 A1 | 1/1987 |

(Continued)

OTHER PUBLICATIONS

Koide, et al. The Fibronectin Type III Domain as a Scaffold for Novel Binding Proteins, J. Mol. Biol. (1998) 284, pp. 1141-1151.
Extended European Search Report dated Dec. 21, 2023.
Alfthan, et al., "Properties of a single-chain antibody containing different linker peptides," Protein Engineering, 8(7): 725-731 (1995).
Altuvia et al., "Ranking Potential Binding Peptides to MHC Molecules by a Computational Threading Approach", Journal of Molecular Biology, vol. 249, Issue 2, pp. 244-250, 1995.
Andersen et al., "Extending Half-life by Indirect Targeting of the neonatal Fc Receptor (FcRn) Using a Minimal Albumin Binding Domain", Journal of Biological Chemistry, vol. 286, No. 7, pp. 5234-5241, 2011.
Barnes et al., "Methods for growth of cultured cells in serum-free medium" Analytical Biochemistry, vol. 102, Issue 2, pp. 255-270, Mar. 1980.

(Continued)

*Primary Examiner* — Suzanne M Noakes
(74) *Attorney, Agent, or Firm* — Goodwin Procter LLP

(57) ABSTRACT

Fibronectin type III domains (FN3) that bind to serum albumin, related polynucleotides capable of encoding serum albumin-binding FN3 domains, cells expressing the FN3 domains, as well as associated vectors, detectably labeled FN3 domains and FN3 domains fused to a heterologous moiety are useful in extending the half-life of molecules in diagnostic and therapeutic applications.

38 Claims, 2 Drawing Sheets

Specification includes a Sequence Listing.

(56) References Cited

FOREIGN PATENT DOCUMENTS

| WO | 1990003430 A1 | 4/1990 |
|---|---|---|
| WO | 9013646 A1 | 11/1990 |
| WO | 9411026 A3 | 8/1994 |
| WO | 0034317 | 6/2000 |
| WO | 2004003019 A2 | 1/2004 |
| WO | 2009085462 A1 | 7/2009 |
| WO | 2010051274 A2 | 5/2010 |
| WO | 2010093627 A2 | 8/2010 |
| WO | 2011140086 A2 | 11/2011 |
| WO | 2011150133 A2 | 12/2011 |
| WO | 2013049275 A1 | 4/2013 |
| WO | 2013177398 A2 | 11/2013 |
| WO | 2014081944 A2 | 5/2014 |
| WO | 2014530014 A | 11/2014 |
| WO | 2015089073 A2 | 6/2015 |
| WO | 2015143199 A1 | 9/2015 |
| WO | 2016197071 A1 | 12/2016 |
| WO | 2017210425 A1 | 12/2017 |
| WO | 2017223180 A2 | 12/2017 |
| WO | 2018052828 A1 | 3/2018 |
| WO | 2018111973 A1 | 6/2018 |
| WO | 2021127353 A1 | 6/2021 |

OTHER PUBLICATIONS

Binz et al., "High-affinity binders selected from designed ankyrin repeat protein libraries," Nature Biotechnology, vol. 22, No. 5, pp. 575-585 (May 2004).
Birtalan et al., "The Intrinsic Contributions of Tyrosine, Serine, Glycine and Arginine to the Affinity and Specificity of Antibodies", Journal of Molecular Biology, vol. 377, Issue 5, pp. 1518-1528, Apr. 2008.
Bork et al., "Proposed acquisition of an animal protein domain by bacteria", Proc. Natl. Acad, Sci, vol. 89, pp. 8990-8994, Oct. 1992.
Breton et al., "Prolonged Half-Life in the Circulation of a Chemical Conjugate Between a Pro-Urokinase Derivative and Human Serum Albumin", Eur. J. Biochem., vol. 231, pp. 563-569, 1995.
Connell, "Expression Systems for use in actinomycetes and related organisms", Curr. Opin. Biotechnol., vol. 12, pp. 446-449, 2001.
Coppieters et al., "Formatted Anti-Tumor necrosis Factor a VHH Proteins Derived From Camelids Show Superior Potency and Targeting to inflamed Joints in a Murine Model of Collagen-Induced Arthritis", Arthritis & Rheumatism, vol. 54, No. 6, pp. 1856-1866, Jun. 2006.
Database Geneseq (online) Aug. 13, 2015 (Aug. 13, 2015), "Staphylococcal leukotoxin binding FN3 domain (Luk122), Seq Id 145", XP055768899, retrieved from EBI accession No. GSP:BCB11489 Database accession No. BCB11489 (1 page).
Database Geneseq, "Staphylococcal LukE binding FN3 domain (Luk51), Seq Id 50", XP002796459, EBI accession No. GSP:BCB11394, *sequence*, (2015). (2 pages).
David et al., "Protein iodination with solid state lactoperoxidase" Biochemistry, vol. 13, No. 5, pp. 1014-1021, 1974.
Dennis "Albumin Binding as a General Strategy for Improving the Pharmacokinetics of Proteins", Journal of Biological Chemistry, vol. 277, No. 38, pp. 35035-35043, 2002.
Dennis et al., "Imaging Tumors with an Albumin-Binding Fab, a Novel Tumor-Targeting Agent", Cancer Research, vol. 67, pp. 254-261, Jan. 2007.
Duttaroy et al., "Development of a Long-Acting Insulin Analog Using Albumin Fusion Technology", Diabetes, vol. 54, pp. 251-258, Jan. 2005.
Final Office Action for U.S. Appl. No. 15/611,296 dated Aug. 4, 2020.
Flisiak et al., "Albinterferon-alfa 2b: a new treatment option for hepatitis C", Expert Opinion on Biological therapy, vol. 10, issue 10, pp. 1509-1515, 201 O.
Hallewell et al., "Genetically engineered Polymers of Human CuZn Superoxide Dismutase", Journal of Biological Chemistry, vol. 264, No. 9, pp. 5260-5268, 1989.
Ham et al., "Media and growth requirements", Methods in Enzymology, vol. 58, pp. 44-93, 1979.
Hanes et al., "In vitro selection and evolution of the functional proteins by using ribosome display", Proc Natl. Acad. Sci,. USA, vol. 94, pp. 4937-4942, May 1997.
Holt et al., "Anti-serum albumin domain antibodies for extending the half-lives of short lived drugs", Protein Engineering Design & Selection, vol. 21, No. 5, pp. 283-288, 2008.
Hunter, "Preparation of Iodine-131 Labelled Human Growth Hormone of High Specific Activity", Nature, vol. 194, 1962.
International Preliminary Report on Patentability for PCTUS2017035442 dated Dec. 4, 2018.
International Preliminary Report on Patentability for PCTUS2020065878 dated May 17, 2022.
International Search Report and Written Opinion for PCTUS2017035442 dated Aug. 11, 2017.
International Search Report and Written Opinion for PCTUS2020065878 dated Mar. 31, 2021.
Jacobs et al., "Design of novel FN3 domains with high stability by a consensus sequence approach", Protein Engineering Design & Selection, vol. 25, No. 3,, pp. 107-117, 2012.
Jacobs Sa et al, "Fusion to a highly stable consensus albumin binding domain allows for tunable pharmacokinetics", Protein Engineering, Design and Selection, Oxford Journal, London, GB, vol. 28, No. 10, doi: 10.1093/PROTEIN/GZV040, ISSN 1741-0126, (Oct. 1, 2015), pp. 385-393, (Aug. 13, 2015), XP002751271.
Koide et al., "High-affinity single-domain binding proteins with a binary-code interface," PNAS, vol. 104, No. 16, pp. 6632-6637 (Apr. 17, 2007).
Koide, et al., "Teaching an Old Scaffold New Tricks: Monobodies Constructed Using Alternative Surfaces of the FN3 Scaffold", Journal of Molecular Biology, Academic Press, vol. 415, No. 3, pp. 393-405 (2011).
Kontermann et al., "Strategies for extended serum half-lite of protein therapeutics" Current Opinion in Biotechnology, vol. 22, pp. 868-876, 2011.
Lehmann et al., "Engineering proteins for theromostability: the use of sequence alignments versus rational design and directed evolution", Current Opinion in Biotechnology, vol. 12, pp. 371-375, 2001.
Luckow et al., "Trends in the Development of Baculovirus Expression Vetors", Biotechnology, vol. 6, pp. 47-55, 1988.
Makrides "Strategies for Achieving High-Level Expression of Genes in *Eschericia coli*", Microbiological Reviews, vol. 60, No. 3, pp. 512-538, 1996.
Malm et al., "Engineering of bispecific affibody molecule towards HER2 and HER3 by addition of an albumin-binding domain allows for affinity purification and in vivo half-life extension", Biotechnology Journal, vol. 9, Issue 9, pp. 1215-1222, Sep. 2014.
Mayfield et al., "Expression and assembly of a fully active antibody in algae, PNAS, vol. 100, No. 2, pp. 438-442, Jan. 2003.
Meinke, et al., "Cellulose-Binding Polypeptides from Cellulomonas fimi: Endoglucanase D (CenD), a Family A ~- 1,4-Glucanase," Journal of Bacteriology, 175(7): 1910-1918 (1993).
Metzner et al., "Genetic fusion to albumin improves the pharmacokinetic properties of factor IX", Thromb. Haemost. vol. 102, pp. 634-644, 2009.
Muller et al., "Improved Pharmacokinetics of Recombinant bispecific Antibody Molecules by Fusion to Human Serum Albumin", Journal of Biological Chemistry, vol. 282, No. 17, p. 12650-12660, Apr. 2007.
Muller et al., "Superior serum half life of albumin tagged TNF ligands", Biochemical and Biophysical Research Communications, vol. 396, pp. 793-799, 2010.
Non Final Office Action for U.S. Appl. No. 15/611,296 dated Aug. 6, 2019.
Non Final Office Action for U.S. Appl. No. 15/611,296 dated Feb. 6, 2020.
Non Final Office Action for U.S. Appl. No. 17/153,229 dated Apr. 5, 2023.
Notice of Allowance for U.S. Appl. No. 15/611,296 dated Oct. 21, 2020.

(56) References Cited

OTHER PUBLICATIONS

Notice of Allowance for U.S. Appl. No. 17/153,229 dated Jul. 28, 2023.

Nygren, "Conjugation of Horseradish Peroxidase to Fab Fragments with Different Homobifunctional and Heterobifunctional Cross-Linking Reagents", Journal of Histochemistry and Cytochemistry, vol. 30, No. 5, pp. 407-412, 1982.

Odegrip et al., "CIS display: In vitro selection of peptides from libraries of protein-DNA complexes", Proc Natl Acad Sci USA, vol. 101, No. 9, pp. 2806-2810, Mar. 2004.

Olson et al., "Design, expression, and stability of a diverse protein library based on the human fibronectin type III domain", Protein Science, vol. 16, No. 3, pp. 476-484, 2007.

Orlova et al., "Site-Specific Radiometal labeling and Improved Biodistribution Using ABY-027, A Novel HER2-Targeting Affibody Molecule-Albumin-Binding Domain Fusion Protein", J. Nucl Med, vol. 54, No. 6, pp. 961-968, Jun. 2013.

Osborn et al., "Albutropin: a growth hormone-albumin fusion with improved pharmacokinetics and pharmacodynamics in rats and monkeys", European Journal of Pharmacology, vol. 456, pp. 149-158, 2002.

Pain et al., "Preparation of Protein A-Peroxidase monoconjugate Using a Heterobifunctional Reagent, and its use in Enzyme Immunoassays", Journal of Immunological Methods, vol. 40, pp. 219-230, 1981.

Raju et al., "Glycoengineering of Therapeutic Glycoproteins: In Virto Galactosylation and Sialylation of Glycoproteins with Terminal N-Acetylglucosamine and Galactose Residues", Biochemistry, vol. 40, pp. 8868-8876, 2001.

Roberts et al., "RNA-peptide fusions for the in vitro selection of peptides and proteins", Proc. Natl. Acad Sci, USA. vol. 94, pp. 12297-12302, Nov. 1997.

Robinson, et al., "Covalent Attachment of Arc Repressor Subunits by a Peptide Linker Enhances Affinity for Operator DNA," Biochemistry, 35: 109-116 (1996).

Schulte "Use of albumin fusion technology to prolong the half-life of recombinant factor VIIa", Thrombosis Research, 122, Suppl. 4, pp. S14-S19, 2008.

Sharp et al., "Synonymous codon usage in *Saccharomyces Cerevisiae*", Yeast, vol. 7, pp. 657-678, 1991.

Sheffield et al., "Prolonged in vivo anticoagulant activity of a hirudin-albumin fusion protein secreted from Pichia pastoris" Blood Coagulation and Fibrinolysis, vol. 12, pp. 433-443, 2001.

Sinclair et al., "Synonymous codon usage bias and the expression of human glucocerebrosidase in the methylotrophic yeast, Pichia pastoris", Protein Expression and Purification, vol. 26, pp. 96-105, 2002.

Tijink et al., "Improved tumor targeting of anti-epidermal growth factor receptor nanobodies through albumin binding: taking advantage of modular Nanobody technology", Mol Cancer Ther, 7(8), pp. 2288-2297, 2008.

Walker et al., "Anti-serum albumin domain antibodies in the development of highly potent, efficacious and long-acting interferon", Protein Engineering, Design & Selection, vol. 23, No. 4, pp. 271-278, 2010.

Watanabe, et al., "Gene Cloning of Chitinase A 1 from Bacillus circulans WL-12 Revealed Its Evolutionary Relationship to Serratia Chitinase and to the Type III Homology United of Fibronectin," The Journal of Biological Chemistry, 265 (26): 15659-15665, 1990.

Wunder et al., "Albumin-based Drug Delivery as Novel Therapeutic Approach for Rheumatoid Arthritis", Journal of immunology, vol. 170, pp. 4 793-4801, 2003.

Zhang et al., "PKSolver: An add-in program for pharmacokinetic and pharmacodynamic data analysis in Microsoft Excel", Computer Methods and Programs in Biomedicine, vol. 99, pp. 306-314, 2010.

Zola, "Monoclonal Antibodies", Encyclopedia of Life Sciences, vol. 9 pp. 14 7-158, 2010.

Table: Summary of Pharmacokinetics parameters

| Test Article | Albumin-binding Centyrin | Route of Administration | Dose (mg/kg) | $C_{max}$ (nM) | $T_{max}$ (hr) | Terminal $t_{1/2}$ (hr) | $AUC_{inf}$ (nM*hr) |
|---|---|---|---|---|---|---|---|
| ALB34 | H9 | i.v. | 5 | 7357.46 | 0.25 | 23.67 | 354,103.49 |
| ALB40 | B7 | i.v. | 5 | 7390.17 | 0.25 | 224.40 | 1,137,560.8 |

FIG. 2

SEQUENCE LISTING

<160> NUMBER OF SEQ ID NOS: 83

<210> SEQ ID NO 1
<211> LENGTH: 89
<212> TYPE: PRT
<213> ORGANISM: Homo sapiens

<400> SEQUENCE: 1

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Glu Phe Thr Thr
                85

<210> SEQ ID NO 2
<211> LENGTH: 94
<212> TYPE: PRT
<213> ORGANISM: Artificial Sequence
<220> FEATURE:
<223> OTHER INFORMATION: synthetic sequence
<220> FEATURE:
<221> NAME/KEY: MISC_FEATURE
<222> LOCATION: (75)..(81)
<223> OTHER INFORMATION: each X is any amino acid
<220> FEATURE:
<221> NAME/KEY: MISC_FEATURE
<222> LOCATION: (82)..(86)
<223> OTHER INFORMATION: each X is any amino acid or deleted

<400> SEQUENCE: 2

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Xaa Xaa Xaa Xaa Xaa Xaa
65                  70                  75                  80

Xaa Xaa Xaa Xaa Xaa Xaa Pro Leu Ser Ala Glu Phe Thr Thr
                85                  90

<210> SEQ ID NO 3
<211> LENGTH: 89
<212> TYPE: PRT
<213> ORGANISM: Artificial Sequence
<220> FEATURE:
<223> OTHER INFORMATION: synthetic sequence
<220> FEATURE:
<221> NAME/KEY: MISC_FEATURE
<222> LOCATION: (22)..(27)
<223> OTHER INFORMATION: each X is Ala, Arg, Asn, Asp, Glu, Gln, Gly,
      His, Ile, Leu, Lys, Phe, Pro, Ser, Thr, Trp, Tyr or Val
<220> FEATURE:
<221> NAME/KEY: MISC_FEATURE
<222> LOCATION: (28)..(28)

```
<223> OTHER INFORMATION: X is Phe, Ile, Leu, Val or Tyr
<220> FEATURE:
<221> NAME/KEY: MISC_FEATURE
<222> LOCATION: (29)..(29)
<223> OTHER INFORMATION: X is Asp, Glu or Thr
<220> FEATURE:
<221> NAME/KEY: MISC_FEATURE
<222> LOCATION: (75)..(79)
<223> OTHER INFORMATION: each X is Ala, Arg, Asn, Asp, Glu, Gln, Gly,
      His, Ile, Leu, Lys, Phe, Pro, Ser, Thr, Trp, Tyr or Val
<220> FEATURE:
<221> NAME/KEY: MISC_FEATURE
<222> LOCATION: (81)..(82)
<223> OTHER INFORMATION: each X is Ala, Arg, Asn, Asp, Glu, Gln, Gly,
      His, Ile, Leu, Lys, Phe, Pro, Ser, Thr, Trp, Tyr or Val

<400> SEQUENCE: 3

Leu Pro Ala Pro Lys Asn Leu Val Val Ser Glu Val Thr Glu Asp Ser
1               5                   10                  15

Leu Arg Leu Ser Trp Xaa Xaa Xaa Xaa Xaa Xaa Xaa Ser Phe Leu
            20                  25                  30

Ile Gln Tyr Gln Glu Ser Glu Lys Val Gly Glu Ala Ile Asn Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val Xaa Xaa Xaa Xaa Xaa Ser
65                  70                  75                  80

Xaa Xaa Leu Ser Ala Glu Phe Thr Thr
                85

<210> SEQ ID NO 4
<211> LENGTH: 89
<212> TYPE: PRT
<213> ORGANISM: Artificial Sequence
<220> FEATURE:
<223> OTHER INFORMATION: synthetic sequence

<400> SEQUENCE: 4

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val Lys Gly Gly His Arg Ser
65                  70                  75                  80

Asn Pro Leu Ser Ala Ile Phe Thr Thr
                85

<210> SEQ ID NO 5
<211> LENGTH: 97
<212> TYPE: PRT
<213> ORGANISM: Artificial Sequence
<220> FEATURE:
<223> OTHER INFORMATION: synthetic sequence
<220> FEATURE:
<221> NAME/KEY: MISC_FEATURE
<222> LOCATION: (22)..(27)
<223> OTHER INFORMATION: each X is A, D, E, F, G, H, I, K, L, N, P, Q,
      R, S, T, V, W or Y
<220> FEATURE:
<221> NAME/KEY: MISC_FEATURE
<222> LOCATION: (28)..(30)
```

```
<223> OTHER INFORMATION: each X is A, D, E, F, G, H, I, K, L, N, P, Q,
      R, S, T, V, W, Y or deleted
<220> FEATURE:
<221> NAME/KEY: MISC_FEATURE
<222> LOCATION: (78)..(84)
<223> OTHER INFORMATION: each X is A, D, E, F, G, H, I, K, L, N, P, Q,
      R, S, T, V, W or Y
<220> FEATURE:
<221> NAME/KEY: MISC_FEATURE
<222> LOCATION: (85)..(87)
<223> OTHER INFORMATION: each X is A, D, E, F, G, H, I, K, L, N, P, Q,
      R, S, T, V, W, Y or deleted

<400> SEQUENCE: 5

Leu Pro Ala Pro Lys Asn Leu Val Val Ser Arg Val Thr Glu Asp Ser
1               5                   10                  15

Ala Arg Leu Ser Trp Xaa Xaa Xaa Xaa Xaa Xaa Xaa Xaa Phe Asp
            20                  25                  30

Ser Phe Leu Ile Gln Tyr Gln Glu Ser Glu Lys Val Gly Glu Ala Ile
            35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Xaa Xaa Xaa
65                  70                  75                  80

Xaa Xaa Xaa Xaa Xaa Xaa Xaa Ser Asn Pro Leu Ser Ala Ile Phe Thr
                85                  90                  95

Thr

<210> SEQ ID NO 6
<211> LENGTH: 96
<212> TYPE: PRT
<213> ORGANISM: Artificial Sequence
<220> FEATURE:
<223> OTHER INFORMATION: synthetic sequence
<220> FEATURE:
<221> NAME/KEY: MISC_FEATURE
<222> LOCATION: (75)..(81)
<223> OTHER INFORMATION: each X is A, D, E, F, G, H, I, K, L, N, P, Q,
      R, S, T, V, W or Y
<220> FEATURE:
<221> NAME/KEY: MISC_FEATURE
<222> LOCATION: (82)..(86)
<223> OTHER INFORMATION: each X is A, D, E, F, G, H, I, K, L, N, P, Q,
      R, S, T, V, W, Y or deleted

<400> SEQUENCE: 6

Leu Pro Ala Pro Lys Asn Leu Val Val Ser Arg Val Thr Glu Asp Ser
1               5                   10                  15

Ala Arg Leu Ser Trp Thr Ala Pro Ala Ala Phe Asp Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Xaa Xaa Xaa Xaa Xaa
65                  70                  75                  80

Xaa Xaa Xaa Xaa Xaa Xaa Ser Asn Pro Leu Ser Ala Ile Phe Thr Thr
                85                  90                  95

<210> SEQ ID NO 7
<211> LENGTH: 89
<212> TYPE: PRT
<213> ORGANISM: Artificial Sequence
<220> FEATURE:
```

<223> OTHER INFORMATION: synthetic sequence
<220> FEATURE:
<221> NAME/KEY: MISC_FEATURE
<222> LOCATION: (32)..(32)
<223> OTHER INFORMATION: X is A, D, E, F, G, H, I, K, L, N, P, Q, R, S,
    T, V, W,Y, or M
<220> FEATURE:
<221> NAME/KEY: MISC_FEATURE
<222> LOCATION: (34)..(34)
<223> OTHER INFORMATION: X is A, D, E, F, G, H, I, K, L, N, P, Q, R, S,
    T, V, W,Y, or M
<220> FEATURE:
<221> NAME/KEY: MISC_FEATURE
<222> LOCATION: (36)..(36)
<223> OTHER INFORMATION: X is A, D, E, F, G, H, I, K, L, N, P, Q, R, S,
    T, V, W,Y, or M
<220> FEATURE:
<221> NAME/KEY: MISC_FEATURE
<222> LOCATION: (38)..(41)
<223> OTHER INFORMATION: each X is A, D, E, F, G, H, I, K, L, N, P, Q,
    R, S, T, V, W,Y, or M
<220> FEATURE:
<221> NAME/KEY: MISC_FEATURE
<222> LOCATION: (68)..(68)
<223> OTHER INFORMATION: X is A, D, E, F, G, H, I, K, L, N, P, Q, R, S,
    T, V, W,Y, or M
<220> FEATURE:
<221> NAME/KEY: MISC_FEATURE
<222> LOCATION: (70)..(70)
<223> OTHER INFORMATION: X is A, D, E, F, G, H, I, K, L, N, P, Q, R, S,
    T, V, W,Y, or M
<220> FEATURE:
<221> NAME/KEY: MISC_FEATURE
<222> LOCATION: (72)..(72)
<223> OTHER INFORMATION: X is A, D, E, F, G, H, I, K, L, N, P, Q, R, S,
    T, V, W,Y, or M
<220> FEATURE:
<221> NAME/KEY: MISC_FEATURE
<222> LOCATION: (78)..(79)
<223> OTHER INFORMATION: each X is A, D, E, F, G, H, I, K, L, N, P, Q,
    R, S, T, V, W,Y, or M
<220> FEATURE:
<221> NAME/KEY: MISC_FEATURE
<222> LOCATION: (81)..(81)
<223> OTHER INFORMATION: X is A, D, E, F, G, H, I, K, L, N, P, Q, R, S,
    T, V, W,Y, or M

<400> SEQUENCE: 7

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Xaa
            20                  25                  30

Ile Xaa Tyr Xaa Glu Xaa Xaa Xaa Xaa Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Xaa Val Xaa Ile Xaa Gly Val Lys Gly Gly Xaa Xaa Ser
65                  70                  75                  80

Xaa Pro Leu Ser Ala Ile Phe Thr Thr
                85

<210> SEQ ID NO 8
<211> LENGTH: 89
<212> TYPE: PRT
<213> ORGANISM: Artificial Sequence
<220> FEATURE:
<223> OTHER INFORMATION: synthetic sequence
<220> FEATURE:
<221> NAME/KEY: MISC_FEATURE
<222> LOCATION: (32)..(32)
<223> OTHER INFORMATION: X is A, D, E, F, G, H, I, K, L, N, P, Q, R, S,
    T, V or W

```
<220> FEATURE:
<221> NAME/KEY: MISC_FEATURE
<222> LOCATION: (34)..(34)
<223> OTHER INFORMATION: X is A, D, E, F, G, H, I, K, L, N, P, Q, R, S,
      T, V or W
<220> FEATURE:
<221> NAME/KEY: MISC_FEATURE
<222> LOCATION: (36)..(36)
<223> OTHER INFORMATION: X is A, D, E, F, G, H, I, K, L, N, P, Q, R, S,
      T, V or W
<220> FEATURE:
<221> NAME/KEY: MISC_FEATURE
<222> LOCATION: (38)..(41)
<223> OTHER INFORMATION: each X is A, D, E, F, G, H, I, K, L, N, P, Q,
      R, S, T, V or W
<220> FEATURE:
<221> NAME/KEY: MISC_FEATURE
<222> LOCATION: (46)..(46)
<223> OTHER INFORMATION: X is A, D, E, F, G, H, I, K, L, N, P, Q, R, S,
      T, V or W
<220> FEATURE:
<221> NAME/KEY: MISC_FEATURE
<222> LOCATION: (48)..(48)
<223> OTHER INFORMATION: X is A, D, E, F, G, H, I, K, L, N, P, Q, R, S,
      T, V or W
<220> FEATURE:
<221> NAME/KEY: MISC_FEATURE
<222> LOCATION: (68)..(68)
<223> OTHER INFORMATION: X is A, D, E, F, G, H, I, K, L, N, P, Q, R, S,
      T, V or W
<220> FEATURE:
<221> NAME/KEY: MISC_FEATURE
<222> LOCATION: (70)..(70)
<223> OTHER INFORMATION: X is A, D, E, F, G, H, I, K, L, N, P, Q, R, S,
      T, V or W
<220> FEATURE:
<221> NAME/KEY: MISC_FEATURE
<222> LOCATION: (72)..(72)
<223> OTHER INFORMATION: X is A, D, E, F, G, H, I, K, L, N, P, Q, R, S,
      T, V or W
<220> FEATURE:
<221> NAME/KEY: MISC_FEATURE
<222> LOCATION: (78)..(79)
<223> OTHER INFORMATION: each X is A, D, E, F, G, H, I, K, L, N, P, Q,
      R, S, T, V or W
<220> FEATURE:
<221> NAME/KEY: MISC_FEATURE
<222> LOCATION: (81)..(81)
<223> OTHER INFORMATION: X is A, D, E, F, G, H, I, K, L, N, P, Q, R, S,
      T, V or W
<220> FEATURE:
<221> NAME/KEY: MISC_FEATURE
<222> LOCATION: (84)..(84)
<223> OTHER INFORMATION: X is A, D, E, F, G, H, I, K, L, N, P, Q, R, S,
      T, V or W
<220> FEATURE:
<221> NAME/KEY: MISC_FEATURE
<222> LOCATION: (86)..(86)
<223> OTHER INFORMATION: X is A, D, E, F, G, H, I, K, L, N, P, Q, R, S,
      T, V or W

<400> SEQUENCE: 8

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Xaa
            20                  25                  30

Ile Xaa Tyr Xaa Glu Xaa Xaa Xaa Xaa Gly Glu Ala Ile Xaa Leu Xaa
        35                  40                  45

Val Pro Gly Ser Glu Arg Ser Tyr Asp Leu Thr Gly Leu Lys Pro Gly
    50                  55                  60

Thr Glu Tyr Xaa Val Xaa Ile Xaa Gly Val Lys Gly Gly Xaa Xaa Ser
65                  70                  75                  80

Xaa Pro Leu Xaa Ala Xaa Phe Thr Thr
```

```
<210> SEQ ID NO 9
<211> LENGTH: 19
<212> TYPE: DNA
<213> ORGANISM: Artificial Sequence
<220> FEATURE:
<223> OTHER INFORMATION: synthetic sequence

<400> SEQUENCE: 9
gtgacacggc ggttagaac                                                  19

<210> SEQ ID NO 10
<211> LENGTH: 20
<212> TYPE: DNA
<213> ORGANISM: Artificial Sequence
<220> FEATURE:
<223> OTHER INFORMATION: synthetic sequence

<400> SEQUENCE: 10
gcctttggga agcttctaag                                                 20

<210> SEQ ID NO 11
<211> LENGTH: 30
<212> TYPE: DNA
<213> ORGANISM: Artificial Sequence
<220> FEATURE:
<223> OTHER INFORMATION: synthetic sequence

<400> SEQUENCE: 11
cggcggttag aacgcggcta caattaatac                                      30

<210> SEQ ID NO 12
<211> LENGTH: 22
<212> TYPE: DNA
<213> ORGANISM: Artificial Sequence
<220> FEATURE:
<223> OTHER INFORMATION: synthetic sequence

<400> SEQUENCE: 12
catgattacg ccaagctcag aa                                              22

<210> SEQ ID NO 13
<211> LENGTH: 385
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (198)..(224)
<223> OTHER INFORMATION: N is any base

<400> SEQUENCE: 13
gtgacacggc ggttagaacg cggctacaat taatacataa ccccatcccc ctgttgacaa     60
ttaatcatcg gctcgtataa tgtgtggaat tgtgagcgga taacaatttc acacaggaaa    120
caggatctac catgctgccg gcgccgaaaa acctggttgt ttctgaagtt accgaagact    180
ctctgcgtct gtcttggnnn nnnnnnnnn nnnnnnnnnn nnnnttygac tctttcctga    240
tccagtacca ggaatctgaa aaagttggtg aagcgatcaa cctgaccgtt ccgggttctg    300
aacgttctta cgacctgacc ggtctgaaac cgggtaccga atacaccgtt tctatctacg    360
gtgttcttag aagcttccca aaggc                                          385
```

```
<210> SEQ ID NO 14
<211> LENGTH: 382
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (198)..(221)
<223> OTHER INFORMATION: N is any base

<400> SEQUENCE: 14
gtgacacggc ggttagaacg cggctacaat taatacataa ccccatcccc ctgttgacaa      60
ttaatcatcg gctcgtataa tgtgtggaat tgtgagcgga taacaatttc acacaggaaa     120
caggatctac catgctgccg gcgccgaaaa acctggttgt ttctgaagtt accgaagact     180
ctctgcgtct gtcttggnnn nnnnnnnnn nnnnnnnnnn nttygactct ttcctgatcc      240
agtaccagga atctgaaaaa gttggtgaag cgatcaacct gaccgttccg ggttctgaac     300
gttcttacga cctgaccggt ctgaaaccgg gtaccgaata caccgtttct atctacggtg     360
ttcttagaag cttcccaaag gc                                              382

<210> SEQ ID NO 15
<211> LENGTH: 379
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (198)..(218)
<223> OTHER INFORMATION: N is any base

<400> SEQUENCE: 15
gtgacacggc ggttagaacg cggctacaat taatacataa ccccatcccc ctgttgacaa      60
ttaatcatcg gctcgtataa tgtgtggaat tgtgagcgga taacaatttc acacaggaaa     120
caggatctac catgctgccg gcgccgaaaa acctggttgt ttctgaagtt accgaagact     180
ctctgcgtct gtcttggnnn nnnnnnnnn nnnnnnntt ygactctttc ctgatccagt      240
accaggaatc tgaaaaagtt ggtgaagcga tcaacctgac cgttccgggt tctgaacgtt     300
cttacgacct gaccggtctg aaaccgggta ccgaatacac cgtttctatc tacggtgttc     360
ttagaagctt cccaaaggc                                                  379

<210> SEQ ID NO 16
<211> LENGTH: 376
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (198)..(215)
<223> OTHER INFORMATION: N is any base

<400> SEQUENCE: 16
gtgacacggc ggttagaacg cggctacaat taatacataa ccccatcccc ctgttgacaa      60
ttaatcatcg gctcgtataa tgtgtggaat tgtgagcgga taacaatttc acacaggaaa     120
caggatctac catgctgccg gcgccgaaaa acctggttgt ttctgaagtt accgaagact     180
ctctgcgtct gtcttggnnn nnnnnnnnn nnnnttyga ctctttcctg atccagtacc      240
aggaatctga aaaagttggt gaagcgatca acctgaccgt tccgggttct gaacgttctt     300
```
acgacctgac cggtctgaaa ccgggtaccg aatacaccgt ttctatctac ggtgttctta    360
gaagcttccc aaaggc    376

<210> SEQ ID NO 17
<211> LENGTH: 131
<212> TYPE: DNA
<213> ORGANISM: Artificial Sequence
<220> FEATURE:
<223> OTHER INFORMATION: synthetic sequence

<400> SEQUENCE: 17
cggcggttag aacgcggcta caattaatac ataaccccat cccctgttg acaattaatc    60 atcggctcgt ataatgtgtg gaattgtgag cggataacaa tttcacacag gaaacaggat    120
ctaccatgct g    131

<210> SEQ ID NO 18
<211> LENGTH: 30
<212> TYPE: DNA
<213> ORGANISM: Artificial Sequence
<220> FEATURE:
<223> OTHER INFORMATION: synthetic sequence

<400> SEQUENCE: 18
cggcggttag aacgcggcta caattaatac    30

<210> SEQ ID NO 19
<211> LENGTH: 81
<212> TYPE: DNA
<213> ORGANISM: Artificial Sequence
<220> FEATURE:
<223> OTHER INFORMATION: synthetic sequence

<400> SEQUENCE: 19
ccaagacaga cgggcagagt cttcggtaac gcgagaaaca accaggtttt tcggcgccgg    60
cagcatggta gatcctgttt c    81

<210> SEQ ID NO 20
<211> LENGTH: 26
<212> TYPE: DNA
<213> ORGANISM: Artificial Sequence
<220> FEATURE:
<223> OTHER INFORMATION: synthetic sequence

<400> SEQUENCE: 20
ccgaagactc tgcccgtctg tcttgg    26

<210> SEQ ID NO 21
<211> LENGTH: 45
<212> TYPE: DNA
<213> ORGANISM: Artificial Sequence
<220> FEATURE:
<223> OTHER INFORMATION: synthetic sequence

<400> SEQUENCE: 21
cagtggtctc acggattcct ggtactggat caggaaagag tcgaa    45

<210> SEQ ID NO 22
<211> LENGTH: 54
<212> TYPE: DNA
<213> ORGANISM: Artificial Sequence
<220> FEATURE:
<223> OTHER INFORMATION: synthetic sequence

<400> SEQUENCE: 22

```
catgcggtct cttccgaaaa agttggtgaa gcgatcgtcc tgaccgttcc gggt        54
```

<210> SEQ ID NO 23
<211> LENGTH: 29
<212> TYPE: DNA
<213> ORGANISM: Artificial Sequence
<220> FEATURE:
<223> OTHER INFORMATION: synthetic sequence

<400> SEQUENCE: 23

```
ggtggtgaag atcgcagaca gcgggttag                                   29
```

<210> SEQ ID NO 24
<211> LENGTH: 21
<212> TYPE: DNA
<213> ORGANISM: Artificial Sequence
<220> FEATURE:
<223> OTHER INFORMATION: synthetic sequence

<400> SEQUENCE: 24

```
cggcggttag aacgcggcta c                                           21
```

<210> SEQ ID NO 25
<211> LENGTH: 61
<212> TYPE: DNA
<213> ORGANISM: Artificial Sequence
<220> FEATURE:
<223> OTHER INFORMATION: synthetic sequence

<400> SEQUENCE: 25

```
aagatcagtt gcggccgcta gactagaacc gctgccaccg ccggtggtga agatcgcaga   60
c                                                                  61
```

<210> SEQ ID NO 26
<211> LENGTH: 485
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (357)..(392)
<223> OTHER INFORMATION: N is any base

<400> SEQUENCE: 26

```
gtgacacggc ggttagaacg cggctacaat taatacataa ccccatcccc ctgttgacaa   60
ttaatcatcg gctcgtataa tgtgtggaat tgtgagcgga taacaatttc acacaggaaa  120
caggatctac catgctgccg gcgccgaaaa acctggttgt ttctcgcgtt accgaagact  180
ctgcgcgtct gtcttggacc gcgccggacg cggcgttcga ctctttcctg atccagtacc  240
aggaatctga aaaagttggt gaagcgatcg tgctgaccgt tccgggttct gaacgttctt  300
acgacctgac cggtctgaaa ccgggtaccg aatacaccgt ttctatctac ggtgttnnnn  360
nnnnnnnnnn nnnnnnnnnn nnnnnnnnnn nntctaaccc gctgtctgcg atcttcacca  420
ccggcggtca ccatcaccat caccatggca gcggttctag tctagcggcc gcaactgatc  480
ttggc                                                             485
```

<210> SEQ ID NO 27
<211> LENGTH: 482
<212> TYPE: DNA
<213> ORGANISM: Artificial Sequence
<220> FEATURE:

<223> OTHER INFORMATION: synthetic sequence
<220> FEATURE:
<221> NAME/KEY: misc_feature
<222> LOCATION: (357)..(389)
<223> OTHER INFORMATION: N is any base

<400> SEQUENCE: 27

```
gtgacacggc ggttagaacg cggctacaat taatacataa ccccatcccc ctgttgacaa      60
ttaatcatcg gctcgtataa tgtgtggaat tgtgagcgga taacaatttc acacaggaaa     120
caggatctac catgctgccg gcgccgaaaa acctggttgt ttctcgcgtt accgaagact     180
ctgcgcgtct gtcttggacc gcgccggacg cggcgttcga ctctttcctg atccagtacc     240
aggaatctga aaaagttggt gaagcgatcg tgctgaccgt tccgggttct gaacgttctt     300
acgacctgac cggtctgaaa ccgggtaccg aatacaccgt ttctatctac ggtgttnnnn     360
nnnnnnnnnn nnnnnnnnnn nnnnnnnnnt ctaacccgct gtctgcgatc ttcaccaccg     420
gcggtcacca tcaccatcac catggcagcg gttctagtct agcggccgca actgatcttg     480
gc                                                                    482
```

<210> SEQ ID NO 28
<211> LENGTH: 479
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (357)..(386)
<223> OTHER INFORMATION: N is any base

<400> SEQUENCE: 28

```
gtgacacggc ggttagaacg cggctacaat taatacataa ccccatcccc ctgttgacaa      60
ttaatcatcg gctcgtataa tgtgtggaat tgtgagcgga taacaatttc acacaggaaa     120
caggatctac catgctgccg gcgccgaaaa acctggttgt ttctcgcgtt accgaagact     180
ctgcgcgtct gtcttggacc gcgccggacg cggcgttcga ctctttcctg atccagtacc     240
aggaatctga aaaagttggt gaagcgatcg tgctgaccgt tccgggttct gaacgttctt     300
acgacctgac cggtctgaaa ccgggtaccg aatacaccgt ttctatctac ggtgttnnnn     360
nnnnnnnnnn nnnnnnnnnn nnnnnntcta acccgctgtc tgcgatcttc accaccggcg     420
gtcaccatca ccatcaccat ggcagcggtt ctagtctagc ggccgcaact gatcttggc     479
```

<210> SEQ ID NO 29
<211> LENGTH: 476
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (357)..(383)
<223> OTHER INFORMATION: N is any base

<400> SEQUENCE: 29

```
gtgacacggc ggttagaacg cggctacaat taatacataa ccccatcccc ctgttgacaa      60
ttaatcatcg gctcgtataa tgtgtggaat tgtgagcgga taacaatttc acacaggaaa     120
caggatctac catgctgccg gcgccgaaaa acctggttgt ttctcgcgtt accgaagact     180
ctgcgcgtct gtcttggacc gcgccggacg cggcgttcga ctctttcctg atccagtacc     240
aggaatctga aaaagttggt gaagcgatcg tgctgaccgt tccgggttct gaacgttctt     300
```

```
acgacctgac cggtctgaaa ccgggtaccg aatacaccgt ttctatctac ggtgttnnnn    360
nnnnnnnnnn nnnnnnnnnn nnntctaacc cgctgtctgc gatcttcacc accggcggtc    420
accatcacca tcaccatggc agcggttcta gtctagcggc cgcaactgat cttggc        476
```

<210> SEQ ID NO 30
<211> LENGTH: 473
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (357)..(380)
<223> OTHER INFORMATION: N is any base

<400> SEQUENCE: 30

```
gtgacacggc ggttagaacg cggctacaat taatacataa ccccatcccc ctgttgacaa     60
ttaatcatcg gctcgtataa tgtgtggaat tgtgagcgga taacaatttc acacaggaaa    120
caggatctac catgctgccg gcgccgaaaa acctggttgt ttctcgcgtt accgaagact    180
ctgcgcgtct gtcttggacc gcgccggacg cggcgttcga ctctttcctg atccagtacc    240
aggaatctga aaaagttggt gaagcgatcg tgctgaccgt tccgggttct gaacgttctt    300
acgacctgac cggtctgaaa ccgggtaccg aatacaccgt ttctatctac ggtgttnnnn    360
nnnnnnnnnn nnnnnnnnnn tctaacccgc tgtctgcgat cttcaccacc ggcggtcacc    420
atcaccatca ccatggcagc ggttctagtc tagcggccgc aactgatctt ggc           473
```

<210> SEQ ID NO 31
<211> LENGTH: 470
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (357)..(377)
<223> OTHER INFORMATION: N is any base

<400> SEQUENCE: 31

```
gtgacacggc ggttagaacg cggctacaat taatacataa ccccatcccc ctgttgacaa     60
ttaatcatcg gctcgtataa tgtgtggaat tgtgagcgga taacaatttc acacaggaaa    120
caggatctac catgctgccg gcgccgaaaa acctggttgt ttctcgcgtt accgaagact    180
ctgcgcgtct gtcttggacc gcgccggacg cggcgttcga ctctttcctg atccagtacc    240
aggaatctga aaaagttggt gaagcgatcg tgctgaccgt tccgggttct gaacgttctt    300
acgacctgac cggtctgaaa ccgggtaccg aatacaccgt ttctatctac ggtgttnnnn    360
nnnnnnnnnn nnnnnntct aacccgctgt ctgcgatctt caccaccggc ggtcaccatc    420
accatcacca tggcagcggt tctagtctag cggccgcaac tgatcttggc               470
```

<210> SEQ ID NO 32
<211> LENGTH: 7
<212> TYPE: PRT
<213> ORGANISM: Artificial Sequence
<220> FEATURE:
<223> OTHER INFORMATION: synthetic sequence

<400> SEQUENCE: 32

```
Lys Gly Gly His Arg Ser Asn
1               5
```

<210> SEQ ID NO 33
<211> LENGTH: 37
<212> TYPE: DNA
<213> ORGANISM: Artificial Sequence
<220> FEATURE:
<223> OTHER INFORMATION: synthetic sequence

<400> SEQUENCE: 33
aagaaggaga accggtatgc tgccggcgcc gaaaaac                              37

<210> SEQ ID NO 34
<211> LENGTH: 65
<212> TYPE: DNA
<213> ORGANISM: Artificial Sequence
<220> FEATURE:
<223> OTHER INFORMATION: synthetic sequence

<400> SEQUENCE: 34
gagccgccgc caccggttta atggtgatgg tgatggtgac caccggtggt gaagatcgca    60
gacag                                                                65

<210> SEQ ID NO 35
<211> LENGTH: 8
<212> TYPE: PRT
<213> ORGANISM: Artificial Sequence
<220> FEATURE:
<223> OTHER INFORMATION: synthetic sequence

<400> SEQUENCE: 35

Ser Phe Leu Ile Gln Tyr Gln Glu
1               5

<210> SEQ ID NO 36
<211> LENGTH: 8
<212> TYPE: PRT
<213> ORGANISM: Artificial Sequence
<220> FEATURE:
<223> OTHER INFORMATION: synthetic sequence

<400> SEQUENCE: 36

Ser Phe Gln Ile Glu Tyr Trp Glu
1               5

<210> SEQ ID NO 37
<211> LENGTH: 8
<212> TYPE: PRT
<213> ORGANISM: Artificial Sequence
<220> FEATURE:
<223> OTHER INFORMATION: synthetic sequence

<400> SEQUENCE: 37

Ser Phe Lys Ile Leu Tyr Glu Glu
1               5

<210> SEQ ID NO 38
<211> LENGTH: 8
<212> TYPE: PRT
<213> ORGANISM: Artificial Sequence
<220> FEATURE:
<223> OTHER INFORMATION: synthetic sequence

<400> SEQUENCE: 38

Ser Phe His Ile Glu Tyr Trp Glu
1               5

```
<210> SEQ ID NO 39
<211> LENGTH: 6
<212> TYPE: PRT
<213> ORGANISM: Artificial Sequence
<220> FEATURE:
<223> OTHER INFORMATION: synthetic sequence

<400> SEQUENCE: 39

Ser Glu Lys Val Gly Glu
1               5

<210> SEQ ID NO 40
<211> LENGTH: 6
<212> TYPE: PRT
<213> ORGANISM: Artificial Sequence
<220> FEATURE:
<223> OTHER INFORMATION: synthetic sequence

<400> SEQUENCE: 40

Asp Asp Val Gly Gly Glu
1               5

<210> SEQ ID NO 41
<211> LENGTH: 6
<212> TYPE: PRT
<213> ORGANISM: Artificial Sequence
<220> FEATURE:
<223> OTHER INFORMATION: synthetic sequence

<400> SEQUENCE: 41

Tyr Leu Val Phe Gly Glu
1               5

<210> SEQ ID NO 42
<211> LENGTH: 6
<212> TYPE: PRT
<213> ORGANISM: Artificial Sequence
<220> FEATURE:
<223> OTHER INFORMATION: synthetic sequence

<400> SEQUENCE: 42

Gln Ser Ile Val Gly Glu
1               5

<210> SEQ ID NO 43
<211> LENGTH: 10
<212> TYPE: PRT
<213> ORGANISM: Artificial Sequence
<220> FEATURE:
<223> OTHER INFORMATION: synthetic sequence

<400> SEQUENCE: 43

Glu Tyr Thr Val Ser Ile Tyr Gly Val Lys
1               5                   10

<210> SEQ ID NO 44
<211> LENGTH: 10
<212> TYPE: PRT
<213> ORGANISM: Artificial Sequence
<220> FEATURE:
<223> OTHER INFORMATION: synthetic sequence

<400> SEQUENCE: 44

Glu Tyr Asp Val Tyr Ile Leu Gly Val Lys
1               5                   10
```

```
<210> SEQ ID NO 45
<211> LENGTH: 10
<212> TYPE: PRT
<213> ORGANISM: Artificial Sequence
<220> FEATURE:
<223> OTHER INFORMATION: synthetic sequence

<400> SEQUENCE: 45

Glu Tyr Trp Val Ala Ile Trp Gly Val Lys
1               5                   10

<210> SEQ ID NO 46
<211> LENGTH: 10
<212> TYPE: PRT
<213> ORGANISM: Artificial Sequence
<220> FEATURE:
<223> OTHER INFORMATION: synthetic sequence

<400> SEQUENCE: 46

Glu Tyr Arg Val Trp Ile Tyr Gly Val Lys
1               5                   10

<210> SEQ ID NO 47
<211> LENGTH: 7
<212> TYPE: PRT
<213> ORGANISM: Artificial Sequence
<220> FEATURE:
<223> OTHER INFORMATION: synthetic sequence

<400> SEQUENCE: 47

Gly Gly His Arg Ser Asn Pro
1               5

<210> SEQ ID NO 48
<211> LENGTH: 7
<212> TYPE: PRT
<213> ORGANISM: Artificial Sequence
<220> FEATURE:
<223> OTHER INFORMATION: synthetic sequence

<400> SEQUENCE: 48

Gly Gly Trp Glu Ser Gly Pro
1               5

<210> SEQ ID NO 49
<211> LENGTH: 7
<212> TYPE: PRT
<213> ORGANISM: Artificial Sequence
<220> FEATURE:
<223> OTHER INFORMATION: synthetic sequence

<400> SEQUENCE: 49

Gly Gly Gln Val Ser Gly Thr
1               5

<210> SEQ ID NO 50
<211> LENGTH: 7
<212> TYPE: PRT
<213> ORGANISM: Artificial Sequence
<220> FEATURE:
<223> OTHER INFORMATION: synthetic sequence

<400> SEQUENCE: 50

Gly Gly Asn Asp Ser Trp Pro
1               5

<210> SEQ ID NO 51
```

```
<211> LENGTH: 90
<212> TYPE: PRT
<213> ORGANISM: Artificial Sequence
<220> FEATURE:
<223> OTHER INFORMATION: synthetic sequence

<400> SEQUENCE: 51

Met Leu Pro Ala Pro Lys Asn Leu Val Ala Ser Arg Val Thr Glu Asp
1               5                   10                  15

Ser Ala Arg Leu Ser Trp Thr Ala Pro Asp Ala Ala Phe Asp Ser Phe
            20                  25                  30

Asn Ile Ala Tyr Trp Glu Pro Gly Ile Gly Gly Glu Ala Ile Trp Leu
        35                  40                  45

Arg Val Pro Gly Ser Glu Arg Ser Tyr Asp Leu Thr Gly Leu Lys Pro
    50                  55                  60

Gly Thr Glu Tyr Lys Val Trp Ile His Gly Val Lys Gly Gly Ala Ser
65                  70                  75                  80

Ser Pro Pro Leu Ile Ala Arg Phe Thr Thr
                85                  90

<210> SEQ ID NO 52
<211> LENGTH: 90
<212> TYPE: PRT
<213> ORGANISM: Artificial Sequence
<220> FEATURE:
<223> OTHER INFORMATION: synthetic sequence

<400> SEQUENCE: 52

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asn Ile Ala Tyr Trp Glu Pro Gly Ile Gly Gly Glu Ala Ile Trp Leu
        35                  40                  45

Arg Val Pro Gly Ser Glu Arg Ser Tyr Asp Leu Thr Gly Leu Lys Pro
    50                  55                  60

Gly Thr Glu Tyr Lys Val Trp Ile His Gly Val Lys Gly Gly Ala Ser
65                  70                  75                  80

Ser Pro Pro Leu Ile Ala Arg Phe Thr Thr
                85                  90

<210> SEQ ID NO 53
<211> LENGTH: 90
<212> TYPE: PRT
<213> ORGANISM: Artificial Sequence
<220> FEATURE:
<223> OTHER INFORMATION: synthetic sequence

<400> SEQUENCE: 53

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Ala Tyr Trp Glu Pro Gly Ile Gly Gly Glu Ala Ile Trp Leu
        35                  40                  45

Arg Val Pro Gly Ser Glu Arg Ser Tyr Asp Leu Thr Gly Leu Lys Pro
    50                  55                  60

Gly Thr Glu Tyr Lys Val Trp Ile His Gly Val Lys Gly Gly Ala Ser
65                  70                  75                  80
```

Ser Pro Pro Leu Ile Ala Arg Phe Thr Thr
                85                  90

<210> SEQ ID NO 54
<211> LENGTH: 90
<212> TYPE: PRT
<213> ORGANISM: Artificial Sequence
<220> FEATURE:
<223> OTHER INFORMATION: synthetic sequence

<400> SEQUENCE: 54

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asn Ile Ser Tyr Trp Glu Pro Gly Ile Gly Gly Glu Ala Ile Trp Leu
        35                  40                  45

Arg Val Pro Gly Ser Glu Arg Ser Tyr Asp Leu Thr Gly Leu Lys Pro
    50                  55                  60

Gly Thr Glu Tyr Lys Val Trp Ile His Gly Val Lys Gly Gly Ala Ser
65                  70                  75                  80

Ser Pro Pro Leu Ile Ala Arg Phe Thr Thr
                85                  90

<210> SEQ ID NO 55
<211> LENGTH: 90
<212> TYPE: PRT
<213> ORGANISM: Artificial Sequence
<220> FEATURE:
<223> OTHER INFORMATION: synthetic sequence

<400> SEQUENCE: 55

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asn Ile Ala Tyr Ala Glu Pro Gly Ile Gly Gly Glu Ala Ile Trp Leu
        35                  40                  45

Arg Val Pro Gly Ser Glu Arg Ser Tyr Asp Leu Thr Gly Leu Lys Pro
    50                  55                  60

Gly Thr Glu Tyr Lys Val Trp Ile His Gly Val Lys Gly Gly Ala Ser
65                  70                  75                  80

Ser Pro Pro Leu Ile Ala Arg Phe Thr Thr
                85                  90

<210> SEQ ID NO 56
<211> LENGTH: 90
<212> TYPE: PRT
<213> ORGANISM: Artificial Sequence
<220> FEATURE:
<223> OTHER INFORMATION: synthetic sequence

<400> SEQUENCE: 56

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asn Ile Ala Tyr Trp Glu Ala Gly Ile Gly Gly Glu Ala Ile Trp Leu
        35                  40                  45

Arg Val Pro Gly Ser Glu Arg Ser Tyr Asp Leu Thr Gly Leu Lys Pro

Gly Thr Glu Tyr Lys Val Trp Ile His Gly Val Lys Gly Gly Ala Ser
65                  70                  75                  80

Ser Pro Pro Leu Ile Ala Arg Phe Thr Thr
                85                  90

<210> SEQ ID NO 57
<211> LENGTH: 90
<212> TYPE: PRT
<213> ORGANISM: Artificial Sequence
<220> FEATURE:
<223> OTHER INFORMATION: synthetic sequence

<400> SEQUENCE: 57

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Asn Ile Ala Tyr Trp Glu Pro Ala Ile Gly Gly Glu Ala Ile Trp Leu
            35                  40                  45

Arg Val Pro Gly Ser Glu Arg Ser Tyr Asp Leu Thr Gly Leu Lys Pro
        50                  55                  60

Gly Thr Glu Tyr Lys Val Trp Ile His Gly Val Lys Gly Gly Ala Ser
65                  70                  75                  80

Ser Pro Pro Leu Ile Ala Arg Phe Thr Thr
                85                  90

<210> SEQ ID NO 58
<211> LENGTH: 90
<212> TYPE: PRT
<213> ORGANISM: Artificial Sequence
<220> FEATURE:
<223> OTHER INFORMATION: synthetic sequence

<400> SEQUENCE: 58

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Asn Ile Ala Tyr Trp Glu Pro Gly Ala Gly Gly Glu Ala Ile Trp Leu
            35                  40                  45

Arg Val Pro Gly Ser Glu Arg Ser Tyr Asp Leu Thr Gly Leu Lys Pro
        50                  55                  60

Gly Thr Glu Tyr Lys Val Trp Ile His Gly Val Lys Gly Gly Ala Ser
65                  70                  75                  80

Ser Pro Pro Leu Ile Ala Arg Phe Thr Thr
                85                  90

<210> SEQ ID NO 59
<211> LENGTH: 90
<212> TYPE: PRT
<213> ORGANISM: Artificial Sequence
<220> FEATURE:
<223> OTHER INFORMATION: synthetic sequence

<400> SEQUENCE: 59

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

```
Asn Ile Ala Tyr Trp Glu Pro Gly Ile Ala Gly Glu Ala Ile Trp Leu
            35                  40                  45

Arg Val Pro Gly Ser Glu Arg Ser Tyr Asp Leu Thr Gly Leu Lys Pro
    50                  55                  60

Gly Thr Glu Tyr Lys Val Trp Ile His Gly Val Lys Gly Gly Ala Ser
65                  70                  75                  80

Ser Pro Pro Leu Ile Ala Arg Phe Thr Thr
                85                  90

<210> SEQ ID NO 60
<211> LENGTH: 90
<212> TYPE: PRT
<213> ORGANISM: Artificial Sequence
<220> FEATURE:
<223> OTHER INFORMATION: synthetic sequence

<400> SEQUENCE: 60

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asn Ile Ala Tyr Trp Glu Pro Gly Ile Gly Gly Glu Ala Ile Ala Leu
            35                  40                  45

Arg Val Pro Gly Ser Glu Arg Ser Tyr Asp Leu Thr Gly Leu Lys Pro
    50                  55                  60

Gly Thr Glu Tyr Lys Val Trp Ile His Gly Val Lys Gly Gly Ala Ser
65                  70                  75                  80

Ser Pro Pro Leu Ile Ala Arg Phe Thr Thr
                85                  90

<210> SEQ ID NO 61
<211> LENGTH: 90
<212> TYPE: PRT
<213> ORGANISM: Artificial Sequence
<220> FEATURE:
<223> OTHER INFORMATION: synthetic sequence

<400> SEQUENCE: 61

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asn Ile Ala Tyr Trp Glu Pro Gly Ile Gly Gly Glu Ala Ile Trp Leu
            35                  40                  45

Ala Val Pro Gly Ser Glu Arg Ser Tyr Asp Leu Thr Gly Leu Lys Pro
    50                  55                  60

Gly Thr Glu Tyr Lys Val Trp Ile His Gly Val Lys Gly Gly Ala Ser
65                  70                  75                  80

Ser Pro Pro Leu Ile Ala Arg Phe Thr Thr
                85                  90

<210> SEQ ID NO 62
<211> LENGTH: 90
<212> TYPE: PRT
<213> ORGANISM: Artificial Sequence
<220> FEATURE:
<223> OTHER INFORMATION: synthetic sequence

<400> SEQUENCE: 62
```

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Asn Ile Ala Tyr Trp Glu Pro Gly Ile Gly Gly Glu Ala Ile Trp Leu
            35                  40                  45

Arg Val Pro Gly Ser Glu Arg Ser Tyr Asp Leu Thr Gly Leu Lys Pro
        50                  55                  60

Gly Thr Glu Tyr Ala Val Trp Ile His Gly Val Lys Gly Gly Ala Ser
65                  70                  75                  80

Ser Pro Pro Leu Ile Ala Arg Phe Thr Thr
                85                  90

<210> SEQ ID NO 63
<211> LENGTH: 90
<212> TYPE: PRT
<213> ORGANISM: Artificial Sequence
<220> FEATURE:
<223> OTHER INFORMATION: synthetic sequence

<400> SEQUENCE: 63

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Asn Ile Ala Tyr Trp Glu Pro Gly Ile Gly Gly Glu Ala Ile Trp Leu
            35                  40                  45

Arg Val Pro Gly Ser Glu Arg Ser Tyr Asp Leu Thr Gly Leu Lys Pro
        50                  55                  60

Gly Thr Glu Tyr Lys Val Ala Ile His Gly Val Lys Gly Gly Ala Ser
65                  70                  75                  80

Ser Pro Pro Leu Ile Ala Arg Phe Thr Thr
                85                  90

<210> SEQ ID NO 64
<211> LENGTH: 90
<212> TYPE: PRT
<213> ORGANISM: Artificial Sequence
<220> FEATURE:
<223> OTHER INFORMATION: synthetic sequence

<400> SEQUENCE: 64

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Asn Ile Ala Tyr Trp Glu Pro Gly Ile Gly Gly Glu Ala Ile Trp Leu
            35                  40                  45

Arg Val Pro Gly Ser Glu Arg Ser Tyr Asp Leu Thr Gly Leu Lys Pro
        50                  55                  60

Gly Thr Glu Tyr Lys Val Trp Ile Ala Gly Val Lys Gly Gly Ala Ser
65                  70                  75                  80

Ser Pro Pro Leu Ile Ala Arg Phe Thr Thr
                85                  90

<210> SEQ ID NO 65
<211> LENGTH: 90
<212> TYPE: PRT
<213> ORGANISM: Artificial Sequence

```
<220> FEATURE:
<223> OTHER INFORMATION: synthetic sequence

<400> SEQUENCE: 65

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asn Ile Ala Tyr Trp Glu Pro Gly Ile Gly Gly Glu Ala Ile Trp Leu
        35                  40                  45

Arg Val Pro Gly Ser Glu Arg Ser Tyr Asp Leu Thr Gly Leu Lys Pro
    50                  55                  60

Gly Thr Glu Tyr Lys Val Trp Ile His Gly Val Lys Gly Gly Ser Ser
65                  70                  75                  80

Ser Pro Pro Leu Ile Ala Arg Phe Thr Thr
                85                  90

<210> SEQ ID NO 66
<211> LENGTH: 90
<212> TYPE: PRT
<213> ORGANISM: Artificial Sequence
<220> FEATURE:
<223> OTHER INFORMATION: synthetic sequence

<400> SEQUENCE: 66

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asn Ile Ala Tyr Trp Glu Pro Gly Ile Gly Gly Glu Ala Ile Trp Leu
        35                  40                  45

Arg Val Pro Gly Ser Glu Arg Ser Tyr Asp Leu Thr Gly Leu Lys Pro
    50                  55                  60

Gly Thr Glu Tyr Lys Val Trp Ile His Gly Val Lys Gly Gly Ala Ala
65                  70                  75                  80

Ser Pro Pro Leu Ile Ala Arg Phe Thr Thr
                85                  90

<210> SEQ ID NO 67
<211> LENGTH: 90
<212> TYPE: PRT
<213> ORGANISM: Artificial Sequence
<220> FEATURE:
<223> OTHER INFORMATION: synthetic sequence

<400> SEQUENCE: 67

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asn Ile Ala Tyr Trp Glu Pro Gly Ile Gly Gly Glu Ala Ile Trp Leu
        35                  40                  45

Arg Val Pro Gly Ser Glu Arg Ser Tyr Asp Leu Thr Gly Leu Lys Pro
    50                  55                  60

Gly Thr Glu Tyr Lys Val Trp Ile His Gly Val Lys Gly Gly Ala Ser
65                  70                  75                  80

Ser Ala Pro Leu Ile Ala Arg Phe Thr Thr
                85                  90
```

```
<210> SEQ ID NO 68
<211> LENGTH: 90
<212> TYPE: PRT
<213> ORGANISM: Artificial Sequence
<220> FEATURE:
<223> OTHER INFORMATION: synthetic sequence

<400> SEQUENCE: 68

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Asn Ile Ala Tyr Trp Glu Pro Gly Ile Gly Gly Glu Ala Ile Trp Leu
            35                  40                  45

Arg Val Pro Gly Ser Glu Arg Ser Tyr Asp Leu Thr Gly Leu Lys Pro
        50                  55                  60

Gly Thr Glu Tyr Lys Val Trp Ile His Gly Val Lys Gly Gly Ala Ser
65                  70                  75                  80

Ser Pro Pro Leu Ala Ala Arg Phe Thr Thr
                85                  90

<210> SEQ ID NO 69
<211> LENGTH: 90
<212> TYPE: PRT
<213> ORGANISM: Artificial Sequence
<220> FEATURE:
<223> OTHER INFORMATION: synthetic sequence

<400> SEQUENCE: 69

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Asn Ile Ala Tyr Trp Glu Pro Gly Ile Gly Gly Glu Ala Ile Trp Leu
            35                  40                  45

Arg Val Pro Gly Ser Glu Arg Ser Tyr Asp Leu Thr Gly Leu Lys Pro
        50                  55                  60

Gly Thr Glu Tyr Lys Val Trp Ile His Gly Val Lys Gly Gly Ala Ser
65                  70                  75                  80

Ser Pro Pro Leu Ile Ala Ala Phe Thr Thr
                85                  90

<210> SEQ ID NO 70
<211> LENGTH: 89
<212> TYPE: PRT
<213> ORGANISM: Artificial Sequence
<220> FEATURE:
<223> OTHER INFORMATION: synthetic sequence

<400> SEQUENCE: 70

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe His
                20                  25                  30

Ile Glu Tyr Trp Glu Gln Ser Ile Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Arg Val Trp Ile Tyr Gly Val Lys Gly Gly Asn Asp Ser
```

```
                65                  70                  75                  80
Trp Pro Leu Ser Ala Ile Phe Thr Thr
                85

<210> SEQ ID NO 71
<211> LENGTH: 4
<212> TYPE: PRT
<213> ORGANISM: Artificial Sequence
<220> FEATURE:
<223> OTHER INFORMATION: synthetic sequence

<400> SEQUENCE: 71

Gly Ser Gly Ser
1

<210> SEQ ID NO 72
<211> LENGTH: 8
<212> TYPE: PRT
<213> ORGANISM: Artificial Sequence
<220> FEATURE:
<223> OTHER INFORMATION: synthetic sequence

<400> SEQUENCE: 72

Gly Gly Gly Ser Gly Gly Gly Ser
1               5

<210> SEQ ID NO 73
<211> LENGTH: 25
<212> TYPE: PRT
<213> ORGANISM: Artificial Sequence
<220> FEATURE:
<223> OTHER INFORMATION: synthetic sequence

<400> SEQUENCE: 73

Gly Gly Gly Gly Ser Gly Gly Gly Gly Ser Gly Gly Gly Gly Ser Gly
1               5                   10                  15
Gly Gly Gly Ser Gly Gly Gly Gly Ser
            20                  25

<210> SEQ ID NO 74
<211> LENGTH: 4
<212> TYPE: PRT
<213> ORGANISM: Artificial Sequence
<220> FEATURE:
<223> OTHER INFORMATION: synthetic sequence

<400> SEQUENCE: 74

Ala Pro Ala Pro
1

<210> SEQ ID NO 75
<211> LENGTH: 10
<212> TYPE: PRT
<213> ORGANISM: Artificial Sequence
<220> FEATURE:
<223> OTHER INFORMATION: synthetic sequence

<400> SEQUENCE: 75

Ala Pro Ala Pro Ala Pro Ala Pro Ala Pro
1               5                   10

<210> SEQ ID NO 76
<211> LENGTH: 20
<212> TYPE: PRT
<213> ORGANISM: Artificial Sequence
<220> FEATURE:
```

<223> OTHER INFORMATION: synthetic sequence

<400> SEQUENCE: 76

Ala Pro Ala Pro Ala Pro Ala Pro Ala Pro Ala Pro Ala Pro Ala Pro
1               5                   10                  15

Ala Pro Ala Pro
            20

<210> SEQ ID NO 77
<211> LENGTH: 40
<212> TYPE: PRT
<213> ORGANISM: Artificial Sequence
<220> FEATURE:
<223> OTHER INFORMATION: synthetic sequence

<400> SEQUENCE: 77

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro Ala Pro Ala Pro Ala Pro
        35                  40

<210> SEQ ID NO 78
<211> LENGTH: 29
<212> TYPE: PRT
<213> ORGANISM: Artificial Sequence
<220> FEATURE:
<223> OTHER INFORMATION: synthetic sequence

<400> SEQUENCE: 78

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala Ala Ala
            20                  25

<210> SEQ ID NO 79
<211> LENGTH: 608
<212> TYPE: PRT
<213> ORGANISM: Homo sapiens

<400> SEQUENCE: 79

Lys Trp Val Thr Phe Ile Ser Leu Leu Phe Leu Phe Ser Ser Ala Tyr
1               5                   10                  15

Ser Arg Gly Val Phe Arg Arg Asp Ala His Lys Ser Glu Val Ala His
            20                  25                  30

Arg Phe Lys Asp Leu Gly Glu Glu Asn Phe Lys Ala Leu Val Leu Ile
        35                  40                  45

Ala Phe Ala Gln Tyr Leu Gln Gln Cys Pro Phe Glu Asp His Val Lys
    50                  55                  60

Leu Val Asn Glu Val Thr Glu Phe Ala Lys Thr Cys Val Ala Asp Glu
65                  70                  75                  80

Ser Ala Glu Asn Cys Asp Lys Ser Leu His Thr Leu Phe Gly Asp Lys
                85                  90                  95

Leu Cys Thr Val Ala Thr Leu Arg Glu Thr Tyr Gly Glu Met Ala Asp
            100                 105                 110

Cys Cys Ala Lys Gln Glu Pro Glu Arg Asn Glu Cys Phe Leu Gln His
        115                 120                 125

Lys Asp Asp Asn Pro Asn Leu Pro Arg Leu Val Arg Pro Glu Val Asp
    130                 135                 140

```
Val Met Cys Thr Ala Phe His Asp Asn Glu Glu Thr Phe Leu Lys Lys
145                 150                 155                 160

Tyr Leu Tyr Glu Ile Ala Arg Arg His Pro Tyr Phe Tyr Ala Pro Glu
            165                 170                 175

Leu Leu Phe Phe Ala Lys Arg Tyr Lys Ala Ala Phe Thr Glu Cys Cys
                180                 185                 190

Gln Ala Ala Asp Lys Ala Ala Cys Leu Leu Pro Lys Leu Asp Glu Leu
            195                 200                 205

Arg Asp Glu Gly Lys Ala Ser Ser Ala Lys Gln Arg Leu Lys Cys Ala
            210                 215                 220

Ser Leu Gln Lys Phe Gly Glu Arg Ala Phe Lys Ala Trp Ala Val Ala
225                 230                 235                 240

Arg Leu Ser Gln Arg Phe Pro Lys Ala Glu Phe Ala Glu Val Ser Lys
                245                 250                 255

Leu Val Thr Asp Leu Thr Lys Val His Thr Glu Cys Cys His Gly Asp
                260                 265                 270

Leu Leu Glu Cys Ala Asp Asp Arg Ala Asp Leu Ala Lys Tyr Ile Cys
            275                 280                 285

Glu Asn Gln Asp Ser Ile Ser Ser Lys Leu Lys Glu Cys Cys Glu Lys
            290                 295                 300

Pro Leu Leu Glu Lys Ser His Cys Ile Ala Glu Val Glu Asn Asp Glu
305                 310                 315                 320

Met Pro Ala Asp Leu Pro Ser Leu Ala Ala Asp Phe Val Glu Ser Lys
                325                 330                 335

Asp Val Cys Lys Asn Tyr Ala Glu Ala Lys Asp Val Phe Leu Gly Met
                340                 345                 350

Phe Leu Tyr Glu Tyr Ala Arg Arg His Pro Asp Tyr Ser Val Val Leu
            355                 360                 365

Leu Leu Arg Leu Ala Lys Thr Tyr Glu Thr Thr Leu Glu Lys Cys Cys
            370                 375                 380

Ala Ala Ala Asp Pro His Glu Cys Tyr Ala Lys Val Phe Asp Glu Phe
385                 390                 395                 400

Lys Pro Leu Val Glu Glu Pro Gln Asn Leu Ile Lys Gln Asn Cys Glu
                405                 410                 415

Leu Phe Glu Gln Leu Gly Glu Tyr Lys Phe Gln Asn Ala Leu Leu Val
                420                 425                 430

Arg Tyr Thr Lys Lys Val Pro Gln Val Ser Thr Pro Thr Leu Val Glu
            435                 440                 445

Val Ser Arg Asn Leu Gly Lys Val Gly Ser Lys Cys Cys Lys His Pro
450                 455                 460

Glu Ala Lys Arg Met Pro Cys Ala Glu Asp Tyr Leu Ser Val Val Leu
465                 470                 475                 480

Asn Gln Leu Cys Val Leu His Glu Lys Thr Pro Val Ser Asp Arg Val
                485                 490                 495

Thr Lys Cys Cys Thr Glu Ser Leu Val Asn Arg Arg Pro Cys Phe Ser
                500                 505                 510

Ala Leu Glu Val Asp Glu Thr Tyr Val Pro Lys Glu Phe Asn Ala Glu
            515                 520                 525

Thr Phe Thr Phe His Ala Asp Ile Cys Thr Leu Ser Glu Lys Glu Arg
            530                 535                 540

Gln Ile Lys Lys Gln Thr Ala Leu Val Glu Leu Val Lys His Lys Pro
545                 550                 555                 560
```

```
Lys Ala Thr Lys Glu Gln Leu Lys Ala Val Met Asp Asp Phe Ala Ala
                565                 570                 575

Phe Val Glu Lys Cys Cys Lys Ala Asp Asp Lys Glu Thr Cys Phe Ala
            580                 585                 590

Glu Glu Gly Lys Lys Leu Val Ala Ala Ser Gln Ala Ala Leu Gly Leu
            595                 600                 605

<210> SEQ ID NO 80
<211> LENGTH: 607
<212> TYPE: PRT
<213> ORGANISM: Macaca fascicularis

<400> SEQUENCE: 80

Lys Trp Val Thr Phe Ile Ser Leu Leu Phe Leu Phe Ser Ser Ala Tyr
1               5                   10                  15

Ser Arg Gly Val Phe Arg Arg Asp Thr His Lys Ser Glu Val Ala His
            20                  25                  30

Arg Phe Lys Asp Leu Gly Glu Glu His Phe Lys Gly Leu Val Leu Val
        35                  40                  45

Ala Phe Ser Gln Tyr Leu Gln Gln Cys Pro Phe Glu His Val Lys
    50                  55                  60

Leu Val Asn Glu Val Thr Glu Phe Ala Lys Thr Cys Val Ala Asp Glu
65                  70                  75                  80

Ser Ala Glu Asn Cys Asp Lys Ser Leu His Thr Leu Phe Gly Asp Lys
                85                  90                  95

Leu Cys Thr Val Ala Thr Leu Arg Glu Thr Tyr Gly Glu Met Ala Asp
            100                 105                 110

Cys Cys Ala Lys Gln Glu Pro Glu Arg Asn Glu Cys Phe Leu Gln His
        115                 120                 125

Lys Asp Asp Asn Pro Asn Leu Pro Pro Leu Val Arg Pro Glu Val Asp
    130                 135                 140

Val Met Cys Thr Ala Phe His Asp Asn Glu Ala Thr Phe Leu Lys Lys
145                 150                 155                 160

Tyr Leu Tyr Glu Val Ala Arg Arg His Pro Tyr Phe Tyr Ala Pro Glu
                165                 170                 175

Leu Leu Phe Phe Ala Ala Arg Tyr Lys Ala Ala Phe Ala Glu Cys Cys
            180                 185                 190

Gln Ala Ala Asp Lys Ala Ala Cys Leu Leu Pro Lys Leu Asp Glu Leu
        195                 200                 205

Arg Asp Glu Gly Lys Ala Ser Ser Ala Lys Gln Arg Leu Lys Cys Ala
    210                 215                 220

Ser Leu Gln Lys Phe Gly Asp Arg Ala Phe Lys Ala Trp Ala Val Ala
225                 230                 235                 240

Arg Leu Ser Gln Lys Phe Pro Lys Ala Glu Phe Ala Glu Val Ser Lys
                245                 250                 255

Leu Val Thr Asp Leu Thr Lys Val His Thr Glu Cys Cys His Gly Asp
            260                 265                 270

Leu Leu Glu Cys Ala Asp Asp Arg Ala Asp Leu Ala Lys Tyr Met Cys
        275                 280                 285

Glu Asn Gln Asp Ser Ile Ser Ser Lys Leu Lys Glu Cys Cys Asp Lys
    290                 295                 300

Pro Leu Leu Glu Lys Ser His Cys Leu Ala Glu Val Glu Asn Asp Glu
305                 310                 315                 320

Met Pro Ala Asp Leu Pro Ser Leu Ala Ala Asp Tyr Val Glu Ser Lys
                325                 330                 335
```

Asp Val Cys Lys Asn Tyr Ala Glu Ala Lys Asp Val Phe Leu Gly Met
            340                 345                 350

Phe Leu Tyr Glu Tyr Ala Arg Arg His Pro Asp Tyr Ser Val Met Leu
            355                 360                 365

Leu Leu Arg Leu Ala Lys Ala Tyr Glu Ala Thr Leu Glu Lys Cys Cys
370                 375                 380

Ala Ala Ala Asp Pro His Glu Cys Tyr Ala Lys Val Phe Asp Glu Phe
385                 390                 395                 400

Gln Pro Leu Val Glu Glu Pro Gln Asn Leu Val Lys Gln Asn Cys Glu
            405                 410                 415

Leu Phe Glu Gln Leu Gly Glu Tyr Lys Phe Gln Asn Ala Leu Leu Val
            420                 425                 430

Arg Tyr Thr Lys Lys Val Pro Gln Val Ser Thr Pro Thr Leu Val Glu
            435                 440                 445

Val Ser Arg Asn Leu Gly Lys Val Gly Ala Lys Cys Cys Lys Leu Pro
450                 455                 460

Glu Ala Lys Arg Met Pro Cys Ala Glu Asp Tyr Leu Ser Val Val Leu
465                 470                 475                 480

Asn Arg Leu Cys Val Leu His Glu Lys Thr Pro Val Ser Glu Lys Val
            485                 490                 495

Thr Lys Cys Cys Thr Glu Ser Leu Val Asn Arg Arg Pro Cys Phe Ser
            500                 505                 510

Ala Leu Glu Leu Asp Glu Ala Tyr Val Pro Lys Ala Phe Asn Ala Glu
            515                 520                 525

Thr Phe Thr Phe His Ala Asp Met Cys Thr Leu Ser Glu Lys Glu Lys
            530                 535                 540

Gln Val Lys Lys Gln Thr Ala Leu Val Glu Leu Val Lys His Lys Pro
545                 550                 555                 560

Lys Ala Thr Lys Glu Gln Leu Lys Gly Val Met Asp Asn Phe Ala Ala
            565                 570                 575

Phe Val Glu Lys Cys Cys Lys Ala Asp Asp Lys Glu Ala Cys Phe Ala
            580                 585                 590

Glu Glu Gly Pro Lys Phe Val Ala Ala Ser Gln Ala Ala Leu Ala
            595                 600                 605

<210> SEQ ID NO 81
<211> LENGTH: 88
<212> TYPE: PRT
<213> ORGANISM: Artificial Sequence
<220> FEATURE:
<223> OTHER INFORMATION: synthetic sequence

<400> SEQUENCE: 81

Asp Ala Pro Ser Gln Ile Glu Val Lys Asp Val Thr Asp Thr Thr Ala
1               5                   10                  15

Leu Ile Thr Trp Phe Lys Pro Leu Ala Glu Ile Asp Gly Ile Glu Leu
            20                  25                  30

Thr Tyr Gly Ile Lys Asp Val Pro Gly Asp Arg Thr Thr Ile Asp Leu
            35                  40                  45

Thr Glu Asp Glu Asn Gln Tyr Ser Ile Gly Asn Leu Lys Pro Asp Thr
        50                  55                  60

Glu Tyr Glu Val Ser Leu Ile Ser Arg Arg Gly Asp Met Ser Ser Asn
65                  70                  75                  80

Pro Ala Lys Glu Thr Phe Thr Thr
                85

```
<210> SEQ ID NO 82
<211> LENGTH: 89
<212> TYPE: PRT
<213> ORGANISM: Artificial Sequence
<220> FEATURE:
<223> OTHER INFORMATION: synthetic sequence

<400> SEQUENCE: 82

Leu Asp Ala Pro Thr Asp Leu Gln Val Thr Asn Val Thr Asp Thr Ser
1               5                   10                  15

Ile Thr Val Ser Trp Thr Pro Pro Ser Ala Thr Ile Thr Gly Tyr Arg
            20                  25                  30

Ile Thr Tyr Thr Pro Ser Asn Gly Pro Gly Glu Pro Lys Glu Leu Thr
        35                  40                  45

Val Pro Pro Ser Ser Thr Ser Val Thr Ile Thr Gly Leu Thr Pro Gly
    50                  55                  60

Val Glu Tyr Val Val Ser Leu Tyr Ala Leu Lys Asp Asn Gln Glu Ser
65                  70                  75                  80

Pro Pro Leu Val Gly Thr Gln Thr Thr
                85

<210> SEQ ID NO 83
<211> LENGTH: 94
<212> TYPE: PRT
<213> ORGANISM: Artificial Sequence
<220> FEATURE:
<223> OTHER INFORMATION: synthetic sequence

<400> SEQUENCE: 83

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90
```

SERUM ALBUMIN-BINDING FIBRONECTIN TYPE III DOMAINS AND USES THEREOF

This application is a National Phase application of International Application No. PCT/US2020/065878, filed Dec. 18, 2020, which claims priority to U.S. Provisional Application No. 62/949,856, filed Dec. 18, 2019, each of which are incorporated herein by reference in their entireties.

TECHNICAL FIELD

The present embodiments relate to fibronectin type III (FN3) domains that bind serum albumin. Such FN3 domains may be used, for example, for extending the in vivo serum half-life of drugs or proteins conjugated thereto. Methods for the production of such molecules and pharmaceutical compositions comprising them are also provided.

BACKGROUND

Rapid elimination of drugs or biotherapeutic molecules from the blood stream can contribute to limited clinical effectiveness of these molecules or result in more frequent dosing for the patient. One method of elimination that commonly occurs is renal clearance due to glomerular filtration. This route of elimination is most associated with smaller biotherapeutics, as the rates of kidney filtration are greatly reduced for molecules with a molecular weight of greater 50,000 daltons (Kontermann, Curr Opin Biotechnol 2011). Several approved biotherapeutic drugs contain active portions that on their own fall below the filtration limit and are thus cleared quickly. To overcome this limitation, a number of technologies have been introduced to effectively increase the size of the therapeutic molecule to reduce kidney filtration. There is still a need for compounds or methods to increase the half-life of a drug or therapeutic. The present embodiments fulfills these needs as well as others.

SUMMARY

The present embodiments provide for serum albumin-binding fibronectin type III (FN3) domains. Also described are related polynucleotides capable of encoding the provided FN3 domains, cells expressing the provided FN3 domains, as well as associated vectors. In addition, methods of using the provided FN3 domains are described. For example, given the extended serum half-life of albumin, albumin-binding peptides can be used as fusion partners for creation of therapeutic proteins or drugs with long or extended serum half-lives.

In addition to the albumin-binding FN3 domains, also provided are polynucleotide sequences capable of encoding the described proteins. Vectors comprising the described polynucleotides are also provided, as are cells expressing the albumin-binding FN3 domains herein. Also described are cells capable of expressing the disclosed vectors. These cells may be mammalian cells (such as 293F cells, CHO cells), insect cells (such as Sf7 cells), yeast cells, plant cells, or bacteria cells (such as E. coli). A process for the production of the described FN3 domains (proteins) is also provided.

The present embodiments also provide methods of fusing or otherwise associating the provided albumin-binding FN3 domains to various molecules to extend the half-lives of such molecules. As such, the albumin-binding FN3 domains can be used, for example, to extend half-lives of therapeutic drugs.

In some embodiments, a pharmaceutical composition comprising the albumin-binding FN3 domain is administered in order to improve the in vivo half-life of the therapeutic partner. Such half-life extension can be assayed by a variety of methods known in the art, including, for example, by monitoring the pharmacokinetics of the albumin-binding FN3 domain. Non-limiting examples of such assays for these methods are provided in the Examples provided herein.

Also provided are kits including the provided albumin-binding FN3 domains. The kits may be used to carry out the methods of using the albumin-binding FN3 domains provided herein, or other methods known to those skilled in the art. In some embodiments the described kits may include the FN3 domains described herein and reagents for use in detecting the presence of human serum albumin in a biological sample. The described kits may include one or more of the FN3 domains described herein and a vessel for containing the FN3 domains when not in use, instructions for use of the FN3 domains affixed to a solid support, and/or detectably labeled forms of the FN3 domains, as described herein.

BRIEF DESCRIPTION OF DRAWINGS

FIG. 2 shows the pharmacokinetic profile of albumin-binding FN3 domains in cynomolgous monkeys following a single IV dose of 5 mg/kg (H9) or 5 mg/kg (ALB40 (B7).

DETAILED DESCRIPTION OF ILLUSTRATIVE EMBODIMENTS

Definitions

Figure 1:
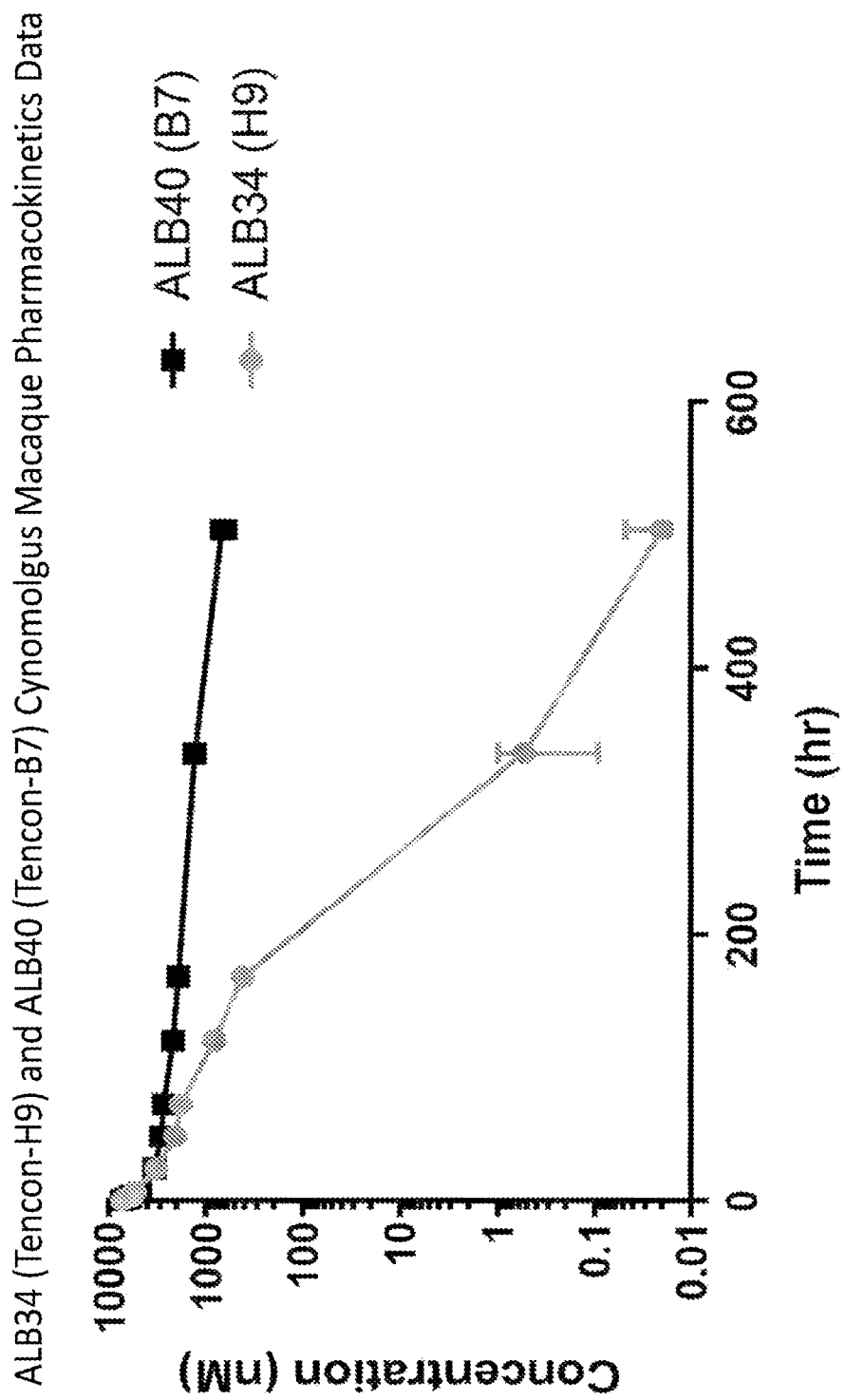
FIG. 1 shows the indirect pull-down of endogenous albumin from cynomolgus monkey and human serum using albumin-binding FN3 domains. FN3 domains that bind to domain 1 of albumin are boxed with dotted lines; FN3 domains that bind to domain 3 of albumin are boxed with solid lines. All constructs are prepared as bispecific genetic fusions with one null FN3 domain (TC25) and one albumin-binding FN3 domain. *ABD refers to albumin binding domain (ref. J. T. Andersen, R. Pehrson, V. Tolmachev, M. B. Daba, L. Abrahmsen, C. Ekblad, J. Biol. Chem. 286: 5234-5241 2011).

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of up to ±10% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

"Isolated" means a biological component (such as a nucleic acid, peptide or protein) has been substantially separated, produced apart from, or purified away from other biological components of the organism in which the component naturally occurs, i.e., other chromosomal and extrachromosomal DNA and RNA, and proteins. Nucleic acids, peptides and proteins that have been "isolated" thus include nucleic acids and proteins purified by standard purification methods. "Isolated" nucleic acids, peptides and proteins can be part of a composition and still be isolated if such composition is not part of the native environment of the nucleic acid, peptide, or protein. The term also embraces nucleic acids, peptides and proteins prepared by recombinant expression in a host cell as well as chemically synthesized nucleic acids. An "isolated" FN3 domain, as used herein, is intended to refer to an FN3 domain which is substantially free of other FN3 domains having different antigenic specificities (for instance, an isolated FN3 domain that specifically binds to human serum albumin is substantially free of FN3 domains that specifically bind antigens other than human serum albumin). An isolated FN3 domain that specifically binds to an epitope, isoform or variant of human serum albumin may, however, have cross-reactivity to other related antigens, for instance from other species (such as serum albumin species homologs).

The term "fibronectin type III (FN3) domain" (FN3 domain) as used herein refers to a domain occurring frequently in proteins including fibronectins, tenascin, intracellular cytoskeletal proteins, cytokine receptors and prokaryotic enzymes (Bork and Doolittle, Proc Nat Acad Sci USA 89:8990-8994, 1992; Meinke et al., J Bacteriol 175:1910-1918, 1993; Watanabe et al., J Biol Chem 265:15659-15665, 1990). Exemplary FN3 domains are the 15 different FN3 domains present in human tenascin C, the 15 different FN3 domains present in human fibronectin (FN), and non-natural synthetic FN3 domains as described for example in U.S. Pat. No. 8,278,419. Individual FN3 domains are referred to by domain number and protein name, e.g., the $3^{rd}$ FN3 domain of tenascin (TN3), or the $10^{th}$ FN3 domain of fibronectin (FN10).

The term "specifically binds" or "specific binding" as used herein refers to the ability of the FN3 domain of the invention to bind to a predetermined antigen with a dissociation constant ($K_D$) of about $1\times10^{-6}$ M or less, for example about $1\times10^{-7}$ M or less, about $1\times10^{-8}$ M or less, about $1\times10^{-9}$ M or less, about $1\times10^{-10}$ M or less, about $1\times10^{-11}$ M or less, about $1\times10^{-12}$ M or less, or about $1\times10^{-13}$ M or less. Typically the described FN3 domain binds to a predetermined antigen (i.e. human serum albumin) with a $K_D$ that is at least ten fold less than its $K_D$ for a nonspecific antigen (for example casein) as measured by surface plasmon resonance using for example a Proteon Instrument (BioRad). The described FN3 domains that specifically bind to human serum albumin may, however, have cross-reactivity to other related antigens, for example to the same predetermined antigen from other species (homologs), such as *Macaca fascicularis* (cynomolgous monkey, cyno) or Pan troglodytes (chimpanzee).

By "serum half-life", as used herein can generally be defined as the time taken for the serum concentration of the amino acid sequence, compound, or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally involve the steps of suitably administering to a warm-blooded animal (i.e. to a human or to another suitable mammal, such as a mouse, rabbit, rat, pig, dog or a primate, for example monkeys from the genus *Macaca* (such as, and in particular, cynomologus monkeys (*Macaca fascicularis*) and/or rhesus monkeys (*Macaca mulatta*)) and baboon (*Papio ursinus*)) a suitable dose of the amino acid sequence, compound or polypeptide of the disclosure; collecting blood samples or other samples from said animal; determining the level or concentration of the amino acid sequence, compound or polypeptide of the invention in said blood sample; and calculating, from (a plot of) the data thus obtained, the time until the level or concentration of the amino acid sequence, compound or polypeptide of the invention has been reduced by 50% compared to the initial level upon dosing. Reference is for example made to the Experimental Part below, as well as to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. edition (1982).

As will also be clear to the skilled person (see for example pages 6 and 7 of WO 04/003019 and in the further references cited therein), the half-life can be expressed using parameters such as the t½-alpha, t½-beta and the area under the curve (AUC). In the present specification, a "half-life" refers to a decrease in any one of these parameters, such as any two of these parameters, or essentially all three of these parameters.

The term "pharmacokinetics" or "pharmacokinetic" is used according to its art accepted meaning and refers to the study of the action of drugs in the body, for example the effect and duration of drug action, the rate at they are absorbed, distributed, metabolized, and eliminated by the body etc.

The term "substituting" or "substituted" or "mutating" or "mutated" as used herein refers to altering, deleting of inserting one or more amino acids or nucleotides in a polypeptide or polynucleotide sequence to generate a variant of that sequence.

The term "randomizing" or "randomized" or "diversified" or "diversifying" as used herein refers to making at least one substitution, insertion or deletion in a polynucleotide or polypeptide sequence.

"Variant" as used herein refers to a polypeptide or a polynucleotide that differs from a reference polypeptide or a reference polynucleotide by one or more modifications for example, substitutions, insertions or deletions.

The term "library" refers to a collection of variants. The library may be composed of polypeptide or polynucleotide variants.

"Tencon" as used herein refers to the synthetic fibronectin type III (FN3) domain having the sequence shown in SEQ ID NO: 1 and described in U.S. Pat. Publ. No. US2010/0216708.

"Polynucleotide," synonymously referred to as "nucleic acid molecule," "nucleotides" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

A "vector" is a replicon, such as plasmid, phage, cosmid, or virus in which another nucleic acid segment may be operably inserted so as to bring about the replication or expression of the segment.

As used herein, the term "host cell" can be any type of cell, e.g., a primary cell, a cell in culture, or a cell from a cell line. In specific embodiments, the term "host cell" refers to a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome. The terms "expression" and "production" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression or production of an antibody or antigen-binding fragment thereof may be within the cytoplasm of the cell, or into the extracellular milieu such as the growth medium of a cell culture. The meaning of "substantially the same" can differ depending on the context in which the term is used. Because of the natural sequence variation likely to exist among heavy and light chains and the genes encoding them, one would expect to find some level of variation within the amino acid sequences or the genes encoding the antibodies or antigen-binding fragments described herein, with little or no impact on their unique binding properties (e.g., specificity and affinity). Such an expectation is due in part to the degeneracy of the genetic code, as well as to the evolutionary success of conservative amino acid sequence variations, which do not appreciably alter the nature of the encoded protein.

Overview of the Disclosed FN3 Domains

Tencon (SEQ ID NO: 1) is a non-naturally occurring fibronectin type III (FN3) domain designed from a consensus sequence of fifteen FN3 domains from human tenascin-C (Jacobs et al., Protein Engineering, Design, and Selection, 25:107-117, 2012; U.S. Pat. Publ. No. 2010/0216708). The crystal structure of Tencon shows six surface-exposed loops that connect seven beta-strands as is characteristic to the FN3 domains, the beta-strands referred to as A, B, C, D, E, F, and G, and the loops referred to as AB, BC, CD, DE, EF, and FG loops (Bork and Doolittle, Proc Natl Acad Sci USA 89:8990-8992, 1992; U.S. Pat. No. 6,673,901). These loops, or selected residues within each loop, may be randomized in order to construct libraries of fibronectin type III (FN3) domains that may be used to select novel molecules that bind serum albumin. Table 1 shows positions and sequences of each loop and beta-strand in Tencon (SEQ ID NO: 1).

TABLE 1

| FN3 domain | Tencon (SEQ ID NO: 1) |
|---|---|
| A strand | 1-12 |
| AB loop | 13-16 |
| B strand | 17-21 |
| BC loop | 22-28 |
| C strand | 29-37 |
| CD loop | 38-43 |
| D strand | 44-50 |
| DE loop | 51-54 |
| E strand | 55-59 |
| EF loop | 60-64 |
| F strand | 65-74 |
| FG loop | 75-81 |
| G strand | 82-89 |

Library designed based on Tencon sequence may thus have randomized FG loop, or randomized BC and FG loops, such as libraries TCL1 or TCL2 as described below. The Tencon BC loop is 7 amino acids long, thus 1, 2, 3, 4, 5, 6 or 7 amino acids may be randomized in the library diversified at the BC loop and designed based on Tencon sequence. The Tencon FG loop is 7 amino acids long, thus 1, 2, 3, 4, 5, 6 or 7 amino acids may be randomized in the library diversified at the FG loop and designed based on Tencon sequence. Further diversity at loops in the Tencon libraries may be achieved by insertion and/or deletions of residues at loops. For example, the FG and/or BC loops may be extended by 1-22 amino acids, or decreased by 1-3 amino acids. The FG loop in Tencon is 7 amino acids long, whereas the corresponding loop in antibody heavy chains ranges from 4-28 residues. To provide maximum diversity, the FG loop may be diversified in sequence as well as in length to correspond to the antibody CDR3 length range of 4-28 residues. For example, the FG loop can further be diversified in length by extending the loop by additional 1, 2, 3, 4 or 5 amino acids.

Library designed based on Tencon sequence may also have randomized alternative surfaces that form on a side of the FN3 domain and comprise two or more beta strands, and at least one loop. One such alternative surface is formed by amino acids in the C and the F beta-strands and the CD and the FG loops (a C-CD-F-FG surface). A library design based on Tencon alternative C-CD-F-FG surface is is described in U.S. Pat. Publ. No. US2013/0226834. Library designed based on Tencon sequence also includes libraries designed based on Tencon variants, such as Tencon variants having substitutions at residues positions 11, 14, 17, 37, 46, 73, or 86 (residue numbering corresponding to SEQ ID NO: 1), and which variants display improve thermal stability. Exemplary Tencon variants are described in US Pat. Publ. No. 2011/0274623, and include Tencon27 (SEQ ID NO: 4) having substitutions E11R, L17A, N46V and E86I when compared to Tencon of SEQ ID NO: 1.

Tencon and other FN3 sequence based libraries may be randomized at chosen residue positions using a random or defined set of amino acids. For example, variants in the library having random substitutions may be generated using NNK codons, which encode all 20 naturally occurring amino acids. In other diversification schemes, DVK codons may be used to encode amino acids Ala, Trp, Tyr, Lys, Thr, Asn, Lys, Ser, Arg, Asp, Glu, Gly, and Cys. Alternatively, NNS codons may be used to give rise to all 20 amino acid residues and simultaneously reducing the frequency of stop codons. Libraries of FN3 domains with biased amino acid distribution at positions to be diversified may be synthesized for example using Slonomics® technology (http:_// www_sloning_com). This technology uses a library of premade double stranded triplets that act as universal building blocks sufficient for thousands of gene synthesis processes. The triplet library represents all possible sequence combinations necessary to build any desired DNA molecule. The codon designations are according to the well known IUB code.

The FN3 domains binding or specifically binding human serum albumin described herein may be isolated by producing the FN3 library such as the Tencon library using cis display to ligate DNA fragments encoding the scaffold proteins to a DNA fragment encoding RepA to generate a pool of protein-DNA complexes formed after in vitro translation wherein each protein is stably associated with the DNA that encodes it (U.S. Pat. No. 7,842,476; Odegrip et al., Proc Natl Acad Sci USA 101, 2806-2810, 2004), and assaying the library for specific binding to human serum albumin by any method known in the art and described in the Example. Exemplary well known methods which can be used are ELISA, sandwich immunoassays, and competitive and non-competitive assays (see, e.g., Ausubel et al., eds, 1994, Current Protocols in Molecular Biology, Vol. 1, John Wiley & Sons, Inc., New York). The identified FN3 domains specifically binding human serum albumin are further characterized according to the desired characteristics.

The FN3 domains specifically binding human serum albumin described herein may be generated using any FN3 domain as a template to generate a library and screening the library for molecules specifically binding human serum albumin using methods provided within. Exemplary FN3 domains that may be used are the 3rd FN3 domain of tenascin C (TN3) (SEQ ID NO: 81), Fibcon (SEQ ID NO: 82), and the 10$^{th}$ FN3 domain of fibronectin (FN10) (SEQ ID NO: 83). Standard cloning and expression techniques are used to clone the libraries into a vector or synthesize double stranded cDNA cassettes of the library, to express, or to translate the libraries in vitro. For example ribosome display (Hanes and Pluckthun, Proc Natl Acad Sci USA, 94, 4937-4942, 1997), mRNA display (Roberts and Szostak, Proc Natl Acad Sci USA, 94, 12297-12302, 1997), or other cell-free systems (U.S. Pat. No. 5,643,768) can be used. The libraries of the FN3 domain variants may be expressed as fusion proteins displayed on the surface for example of any suitable bacteriophage. Methods for displaying fusion polypeptides on the surface of a bacteriophage are well known (U.S. Pat. Publ. No. 2011/0118144; Int. Pat. Publ. No. WO2009/ 085462; U.S. Pat. Nos. 6,969,108; 6,172,197; 5,223,409; 6,582,915; 6,472,147).

In some embodiments described herein, the FN3 domain specifically binding human serum albumin is based on Tencon sequence of SEQ ID NO: 1 or Tencon27 sequence of SEQ ID NO: 4, the SEQ ID NO: 1 or the SEQ ID NO: 4, optionally having substitutions at residues positions 11, 14, 17, 37, 46, 73, and/or 86.

The FN3 domains specifically binding human serum albumin of the disclosure may be modified to improve their properties such as improve thermal stability and reversibility of thermal folding and unfolding. Several methods have been applied to increase the apparent thermal stability of proteins and enzymes, including rational design based on comparison to highly similar thermostable sequences, design of stabilizing disulfide bridges, mutations to increase alpha-helix propensity, engineering of salt bridges, alteration of the surface charge of the protein, directed evolution, and composition of consensus sequences (Lehmann and Wyss, Curr Opin Biotechnol, 12, 371-375, 2001). High thermal stability may increase the yield of the expressed protein, improve solubility or activity, decrease immunogenicity, and minimize the need of a cold chain in manufacturing. Residues that may be substituted to improve thermal stability of Tencon (SEQ ID NO: 1) are residue positions 11, 14, 17, 37, 46, 73, or 86, and are described in US Pat. Publ. No. 2011/0274623. Substitutions corresponding to these residues may be incorporated to the FN3 domain containing molecules of the invention.

Measurement of protein stability and protein lability can be viewed as the same or different aspects of protein integrity. Proteins are sensitive or "labile" to denaturation caused by heat, by ultraviolet or ionizing radiation, changes in the ambient osmolarity and pH if in liquid solution, mechanical shear force imposed by small pore-size filtration, ultraviolet radiation, ionizing radiation, such as by gamma irradiation, chemical or heat dehydration, or any other action or force that may cause protein structure disruption. The stability of the molecule can be determined using standard methods. For example, the stability of a molecule can be determined by measuring the thermal melting ("$T_m$") temperature, the temperature in ° Celsius (° C.) at which half of the molecules become unfolded, using standard methods. Typically, the higher the $T_m$, the more stable the molecule. In addition to heat, the chemical environment also changes the ability of the protein to maintain a particular three dimensional structure.

In one embodiment, the FN3 domain specifically binding human serum albumin of the disclosure may exhibit increased stability by at least 5%, 10%, 15%, 20%, 25%, 30%, 35%, 40%, 45%, 50%, 55%, 60%, 65%, 70%, 75%, 80%, 85%, 90%, or 95% or more compared to the same domain prior to engineering measured by the increase in the $T_m$.

Chemical denaturation can likewise be measured by a variety of methods. Chemical denaturants include guanidinium hydrochloride, guanidinium thiocyanate, urea, acetone, organic solvents (DMF, benzene, acetonitrile), salts (ammonium sulfate, lithium bromide, lithium chloride, sodium bromide, calcium chloride, sodium chloride); reducing agents (e.g. dithiothreitol, beta-mercaptoethanol, dinitrothiobenzene, and hydrides, such as sodium borohydride), non-ionic and ionic detergents, acids (e.g. hydrochloric acid (HCl), acetic acid ($CH_3COOH$), halogenated acetic acids), hydrophobic molecules (e.g. phospholipids), and targeted denaturants. Quantitation of the extent of denaturation can rely on loss of a functional property, such as ability to bind a target molecule, or by physiochemical properties, such as tendency to aggregation, exposure of formerly solvent inaccessible residues, or disruption or formation of disulfide bonds.

The FN3 domain of the disclosure may be generated as monomers, dimers, or multimers, for example, as a means to increase the valency and thus the avidity of target molecule binding, or to generate bi- or multispecific scaffolds simultaneously binding two or more different target molecules. The dimers and multimers may be generated by linking monospecific, bi- or multispecific protein scaffolds, for example, by the inclusion of an amino acid linker, for example a linker containing poly-glycine, glycine and serine, or alanine and proline. Exemplary linker include $(GS)_2$, (SEQ ID NO: 71), $(GGGS)_2$ (SEQ ID NO: 72), $(GGGGS)_5$ (SEQ ID NO: 73), $(AP)_2$ (SEQ ID NO: 74), $(AP)_5$ (SEQ ID NO: 75), $(AP)_{10}$ (SEQ ID NO: 76), $(AP)_{20}$ (SEQ ID NO: 77) and $A(EAAAK)_5AAA$ (SEQ ID NO: 78). The dimers and multimers may be linked to each other in a N- to C-direction. The use of naturally occurring as well as artificial peptide linkers to connect polypeptides into novel linked fusion polypeptides is well known in the literature (Hallewell et al., *J Biol Chem* 264, 5260-5268, 1989; Alfthan et al., *Protein Eng.* 8, 725-731, 1995; Robinson & Sauer, *Biochemistry* 35, 109-116, 1996; U.S. Pat. No. 5,856,456).

Human Serum Albumin Binders

FN3 domains are cleared rapidly from circulation via renal filtration and degradation due to their small size of ~10 kDa. In certain aspects, the disclosure provides FN3 domains that bind specifically to serum albumin, e.g., human serum albumin (HSA) to prolong the half-life of the FN3 domain or of another therapeutic to which the albumin-binding FN3 domain is associated or linked with.

In some embodiments, the human serum albumin-binding FN3 domains comprises an initiator methionine (Met) linked to the N-terminus of the molecule.

In some embodiments, the human serum albumin-binding FN3 domains comprise a cysteine (Cys) linked to a C-terminus or the N-terminus of the FN3 domain.

The addition of the N-terminal Met and/or the C-terminal Cys may facilitate expression and/or conjugation to another molecule, which can be another half-life extending molecules, such as PEG, a Fc region, another FN3 domains, and the like.

In some embodiments, the FN3 domain comprises the amino acid sequence of SEQ ID NOs: 51, 52, 53, 54, 55, 56, 57, 58, 59, 60, 61, 62, 63, 64, 65, 66, 67, 68, or 69. In some embodiments, the FN3 domain (protein) is isolated. In some embodiments, the FN3 protein comprises SEQ ID NO: 51 with at least one substitution as compared to SEQ ID NO: 51. In some embodiments, the substitution is at a residue that corresponds to position 10 of SEQ ID NO: 51. In some embodiments the substitution (mutation) is A10V. In some embodiments, the substitution is A10 to G, L, I, T, or S. In some embodiments, the substitution at position 10 is any naturally occurring amino acid.

In some embodiments, the FN3 domain comprises an amino acid sequence that is at least, or is, 85%, 86%, 87%, 88%, 89%, 90%, 91%, 92%, 93%, 94%, 95%, 96%, 97%, 98%, or 99% identical to the amino acid sequence of SEQ ID NO: 51, 52, 53, 54, 55, 56, 57, 58, 59, 60, 61, 62, 63, 64, 65, 66, 67, 68, or 69. In some embodiments the FN3 domain comprises an amino acid sequence that is at least, or is, 85%, 86%, 87%, 88%, 89%, 90%, 901%, 92%, 93%, 94%, 95%, 96%, 97%, 98%, or 99% identical to the amino acid sequence of SEQ ID NO: 51, 52, 53, 54, 55, 56, 57, 58, 59, 60, 61, 62, 63, 64, 65, 66, 67, 68, or 69 provided that the protein has a substitution that corresponds to position 10 of SEQ ID NO: 51, 52, 53, 54, 55, 56, 57, 58, 59, 60, 61, 62, 63, 64, 65, 66, 67, 68, or 69. In some embodiments, the substitution is A10V. In some embodiments, the substitution is A10G, A10L, A10I, A10T, or A10S. In some embodiments, the substitution at position 10 is any naturally occurring amino acid.

In some embodiments, the isolated FN3 domain comprises an amino acid sequence that has 1, 2, 3, 4, 5, 6, 7, 8, 9, 10, 11, 12, 13, or 14 substitutions when compared to the amino acid sequence of SEQ ID NOs: 51, 52, 53, 54, 55, 56, 57, 58, 59, 60, 61, 62, 63, 64, 65, 66, 67, 68, or 69. In some embodiments, the substitution is at a position that corresponds to position 10 of SEQ ID NOs: 51, 52, 53, 54, 55, 56, 57, 58, 59, 60, 61, 62, 63, 64, 65, 66, 67, 68, or 69.

In some embodiments, FN3 domains provided comprises a cysteine residue in at least one residue position corresponding to residue positions 6, 11, 22, 25, 26, 52, 53, 61, 88 or positions 6, 8, 10, 11, 14, 15, 16, 20, 30, 34, 38, 40, 41, 45, 47, 48, 53, 54, 59, 60, 62, 64, 70, 88, 89, 90, 91, or 93 of SEQ ID NO 1, or at a C-terminus. Although the positions are listed in a series, each position can also be chosen individually. In some embodiments, the cysteine is at a position that corresponds to position 6, 53, or 88.

In certain embodiments, the isolated FN3 domain as described herein may comprise the sequence as set forth in SEQ ID NO: 51, 52, 53, 54, 55, 56, 57, 58, 59, 60, 61, 62, 63, 64, 65, 66, 67, 68, or 69, wherein the C-strand, the CD loop, the F-strand and the FG-loops are replaced with a respective set of specified C-strand, the CD loop, the F-strand and the FG-loops from any of the described albumin-binding FN3 domain sequences (i.e., SEQ ID NOs: 51, 52, 53, 54, 55, 56, 57, 58, 59, 60, 61, 62, 63, 64, 65, 66, 67, 68, or 69), or sequences at least 85%, 90%, 95%, 97%, 98%, or 99% identical to the C-strand, the CD loop, the F-strand and the FG-loop sequences of the four core FN3 domain sequences.

In some embodiments, the isolated albumin-binding FN3 domains comprise a sequence as set forth in SEQ ID NO: 51, 52, 53, 54, 55, 56, 57, 58, 59, 60, 61, 62, 63, 64, 65, 66, 67, 68, or 69.

In some embodiments, the FN3 domain comprises SEQ ID NO: 51 with a substitution of: A10V, N33A, A35S, W37A, P39A, G40A, I41A, G42A, W47A, R49A, K69A, W71A, H73A, A79S, S80A, P82A, I85A, or R87A. In some embodiments, the FN3 domain comprises SEQ ID NO: 51 with a substitution at the position of 10, 33, 25, 37, 39, 40, 41, 42, 47, 49, 69, 71, 73, 79, 80, 82, 85, or 87. In some embodiments, the FN3 domain comprises SEQ ID NO: 51 with a substitution at the position of 10. In some embodiments, the FN3 domain comprises SEQ ID NO: 51 with a substitution at the position of 10 and additional substitutions of A10V, A10G, A10L, A10I, A10T, or A10S.

In some embodiments, the FN3 domain comprises an amino acid sequence that is 90% identical to the amino acid sequence of SEQ ID NO: 51, or that has 1, 2, 3, 4, 5, 6, 7, 8, 9, 10, 11, 12, 13, or 14 substitutions when compared to the amino acid sequence of SEQ ID NO: 51.

In some embodiments, the substitution is an alanine substitution. In some embodiments, the substitution is G, L, I, T, or S. In some embodiments, the substitution or change is to any other naturally occurring amino acid residue. "Naturally occurring amino acid residue" refers to the 20 amino acid residues, such as alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine. In some embodiments W37 or W47 is substituted with a different hydrophobic residue, such as glycine, alanine, valine, leucine, isoleucine, proline, phenylalanine, or methionine. In some embodiments W37 or W47 is substituted with a phenylalanine or tyrosine.

Fusions of Human Serum Albumin-Binding FN3 Domains

In some embodiments, the present disclosure provides for conjugates comprising a serum albumin binding FN3 domain and at least one additional moiety. The additional moiety may be useful for any diagnostic, imaging, or therapeutic purpose. In some embodiments, the additional moiety is an antisense oligonucleotide, a siRNA, miRNA, antibody, another FN3 domain, and the like. Examples of other FN3 domains include, but are not limited, to those provided for in U.S. Pat. Nos. 8,278,419, 9,200,059, 10,040,842, 8,569,227, 9,234,029, 9,982,253, 9,200,273, 9,897,612, 10,196,446, 8,415,291, 8,617,894, 9,695,228, 9,725,497, 9,156,887, or 10,280,200, each of which is incorporated in reference by its entirety, including the specific FN3 domains that are provided for in the same. or provided for in U.S. patent application Ser. Nos. 15/629,090, 16/218,990, 15/637,276, 15/148,312, 15/611,296, 15/839,915, 15/840,281, 15/840,303, 62/914,643, 62/914,654, or 62/914,725, each of which is incorporated in reference by its entirety, including the specific FN3 domains that are provided for in the same.

In certain embodiments, the serum half-life of the moiety fused to the described FN3 domain is increased relative to the serum half-life of the moiety when not conjugated to the FN3 domain. In certain embodiments, the serum half-life of the FN3 domain fusion is at least 20, 40, 60, 80, 100, 120, 150, 180, 200, 400, 600, 800, 1000, 1200, 1500, 1800, 1900, 2000, 2500, or 3000% longer relative to the serum half-life of the moiety when not fused to the described FN3 domain. In other embodiments, the serum half-life of the FN3 domain fusion is at least 1.5-fold, 2-fold, 2.5-fold, 3-fold, 3.5 fold, 4-fold, 4.5-fold, 5-fold, 6-fold, 7-fold, 8-fold, 10-fold, 12-fold, 13-fold, 15-fold, 17-fold, 20-fold, 22-fold, 25-fold, 27-fold, 30-fold, 35-fold, 40-fold, or 50-fold greater than the serum half-life of the moiety when not fused to the described FN3 domain. In some embodiments, the serum half-life of the FN3 domain fusion is at least 2 hours, 2.5 hours, 3 hours, 4 hours, 5 hours, 6 hours, 7 hours, 8 hours, 9 hours, 10 hours, 15 hours, 20 hours, 25 hours, 30 hours, 35 hours or 40 hours in cynomolgus monkey.

Accordingly, the described FN3 domain fusion molecules described herein are useful for increasing the half-life of a therapeutic moiety by creating a fusion between the therapeutic moiety and the described FN3 domain. Such fusion molecules may be used to treat conditions which respond to the biological activity of the therapeutic moiety contained in the fusion. The present disclosure contemplates the use of the described FN3 domain fusion molecules in diseases caused by the disregulation of any of the following proteins or molecules.

Heterologous Moiety

In some embodiments, the described FN3 domains are fused to a second moiety that is a small organic molecule, a nucleic acid molecule, or a protein. In some embodiments, the described FN3 domains is fused to a therapeutic moiety that targets receptors, receptor ligands, viral coat proteins, immune system proteins, hormones, enzymes, antigens, or cell signaling proteins. The fusion may be formed by attaching the second moiety to either end of the described FN3 domains, i.e., FN3 domain-therapeutic molecule or therapeutic molecule-FN3 domain arrangements.

In other exemplary embodiments, the described FN3 domain is fused to one or more additional FN3 domains. For example, the described FN3 domain may be fused to one, two, three, four or more additional FN3 domains. The additional FN3 domains may bind to the same or different targets other than serum albumin. Examples of FN3 domains are provided herein and are incorporated by reference.

In some embodiments, the described FN3 domains is linked to another molecule. In some embodiments, the another molecule is a drug or therapeutic, a protein, an antibody, a polymer, a toxin. In some embodiments, the another molecule is a FN3 domain that binds to a molecule other than human albumin. In some embodiments, the other FN3 domain binds to CD71. In some embodiments, the described FN3 domains is linked directly to the another molecule. In some embodiments, the described FN3 domains is linked through a linker to the another molecule. In some embodiments, the linker is a peptide linker. In some embodiments, the peptide linker comprises a sequence of (GS)2, (SEQ ID NO: 71), (GGGS)2 (SEQ ID NO: 72), (GGGGS)5 (SEQ ID NO: 73), (AP)2 (SEQ ID NO: 74), (AP)5 (SEQ ID NO: 75), (AP)10 (SEQ ID NO: 76), (AP)20 (SEQ ID NO: 77) and A(EAAAK)5AAA (SEQ ID NO: 78).

In certain embodiments, the application provides a FN3-Y fusion that may be represented by the formula: FN3-X-Y or Y-X FN3, wherein FN3 is an FN3 domain as described herein (including any N-terminal and/or C-terminal extensions), X is a polypeptide linker (suitable linkers include, for example, any one of SEQ ID NOs: 71-78), and Y is a therapeutic moiety as described herein.

In certain embodiments, the application provides a FN3-Y fusion that may be represented by the formula: FN3-Xi-Cys-$X_2$-Y or Y-Xi-Cys-$X_2$-FN3, wherein FN3 is a FN3 domain as described herein (including any N-terminal and/or C-terminal extensions), Xi is an optional polypeptide linker (suitable linkers include, for example, any one of SEQ ID NOs: 71-78), Cys is a cysteine residue, $X_2$ is a chemically derived spacer, and Y is a therapeutic moiety as described herein. In exemplary embodiments, the chemically derived spacer contains a maleimide moiety which may used to conjugate the therapeutic moiety to the C-terminal Cys of the described FN3 domains, or to conjugate the described FN3 domains to the C-terminal Cys of the therapeutic moiety, by Michael addition as described further herein. In other aspects, a described FN3 domain may be bound to two or more therapeutic moieties. For example, two moieties can be bound to a described FN3 domains in various arrangements, such as for example, from N-terminus to C-terminus of a fusion sequence, as follows: X-Y-FN3, X-FN3-Y, or FN3-X-Y, wherein X and Y represent two different therapeutic moieties. The two different therapeutic moieties may be selected from any of the moieties disclosed herein.

In certain embodiments, the bispecific FN3 molecule comprising a first FN3 domain and a second FN3 domain, wherein the first FN3 domain comprises a serum albumin binding FN3 domain described herein and the second FN3 domain binds to a target protein other than human serum albumin.

Deimmunization of Binding Polypeptides

The amino acid sequences of serum albumin binders and their fusions may be altered to eliminate one or more B- or T-cell epitopes. A protein, including the described FN3 domain fusions described herein, may be deimmunized to render it non-immunogenic, or less immunogenic, to a given species. Deimmunization can be achieved through structural alterations to the protein. Any deimmunization technique known to those skilled in the art can be employed, see e.g., WO 00/34317, the disclosure of which is incorporated herein in its entirety.

In one embodiment, the sequences of the serum albumin binders and their fusions can be analyzed for the presence of MHC class II binding motifs. For example, a comparison may be made with databases of MHC-binding motifs such as, for example by searching the "motifs" database on the worldwide web at sitewehil.wehi.edu.au. Alternatively, MHC class II binding peptides may be identified using computational threading methods such as those devised by Altuvia et al. (J. Mol. Biol. 249 244-250 (1995)) whereby consecutive overlapping peptides from the polypeptide are testing for their binding energies to MHC class II proteins. Computational binding prediction algorithms include iTope™, Tepitope, SYFPEITHI, EpiMatrix (EpiVax), and MHCpred. In order to assist the identification of MHC class II-binding peptides, associated sequence features which relate to successfully presented peptides such as amphipathicity and Rothbard motifs, and cleavage sites for cathepsin B and other processing enzymes can be searched for.

Having identified potential (e.g. human) T-cell epitopes, these epitopes are then eliminated by alteration of one or more amino acids, as required to eliminate the T-cell epitope. Usually, this will involve alteration of one or more amino acids within the T-cell epitope itself. This could involve altering an amino acid adjacent the epitope in terms of the primary structure of the protein or one which is not adjacent in the primary structure but is adjacent in the secondary structure of the molecule. The usual alteration contemplated will be amino acid substitution, but it is possible that in certain circumstances amino acid addition or deletion will be appropriate. All alterations can be accomplished by recombinant DNA technology, so that the final molecule may be prepared by expression from a recombinant host, for example by well established methods, but the use of protein chemistry or any other means of molecular alteration may also be used.

Once identified T-cell epitopes are removed, the deimmunized sequence may be analyzed again to ensure that new T-cell epitopes have not been created and, if they have, the epitope(s) can be deleted.

Not all T-cell epitopes identified computationally need to be removed. A person skilled in the art will appreciate the significance of the "strength" or rather potential immunogenicity of particular epitopes. The various computational methods generate scores for potential epitopes. A person skilled in the art will recognize that only the high scoring epitopes may need to be removed. A skilled person will also recognize that there is a balance between removing potential epitopes and maintaining binding affinity or other biological activity of the protein. Therefore, one strategy is to sequentially introduce substitutions into the described FN3 domains or FN3 domain fusion protein and then test for target binding or other biological activity and immunogenicity.

Additional Modifications

In certain embodiments, the serum albumin binders and their fusions may further comprise post-translational modifications. Exemplary post-translational protein modification include phosphorylation, acetylation, methylation, ADP-ribosylation, ubiquitination, glycosylation, carbonylation, sumoylation, biotinylation or addition of a polypeptide side chain or of a hydrophobic group. As a result, the modified serum albumin binders and their fusions s may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogenicity of the protein. See, e.g., Raju et al. Biochemistry. 2001 Jul. 31; 40(30):8868-76. Effects of such non-amino acid elements on the functionality of the serum albumin binders or their fusions may be tested for their ability to bind a particular serum albumin (e.g., HSA or RhSA) and/or the functional role conferred by a specific non-FN3 moiety in the context of a fusion (e.g., the effect of FGF21 on glucose uptake).

Vectors & Polynucleotides Embodiments

Also included in the present disclosure are nucleic acid sequences encoding any of the proteins described herein. As appreciated by those skilled in the art, because of third base degeneracy, almost every amino acid can be represented by more than one triplet codon in a coding nucleotide sequence. In addition, minor base pair changes may result in a conservative substitution in the amino acid sequence encoded but are not expected to substantially alter the biological activity of the gene product. Therefore, a nucleic acid sequence encoding a protein described herein may be modified slightly in sequence and yet still encode its respective gene product.

Nucleic acids encoding any of the various proteins or polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al, Proc Natl Acad Sci USA. 2003 100(2):438-42; Sinclair et al. Protein Expr Purif. 2002 (1):96-105; Connell N D. Curr Opin Biotechnol. 2001 (5):446-9; Makrides et al. Microbiol Rev. 1996 60(3):512-38; and Sharp et al. Yeast. 1991 7(7):657-78.

General techniques for nucleic acid manipulation are within the purview of one skilled in the art and are also described for example in Sambrook et al., Molecular Cloning: A Laboratory Manual, Vols. 1-3, Cold Spring Harbor Laboratory Press, 2 ed., 1989, or F. Ausubel et al, Current Protocols in Molecular Biology (Green Publishing and Wiley-Interscience: New York, 1987) and periodic updates, herein incorporated by reference. The DNA encoding a protein is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants are additionally incorporated. Suitable regulatory elements are well-known in the art.

The proteins and fusion proteins described herein may be produced as a fusion protein with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native signal sequence, the signal sequence is substituted by a prokaryotic signal sequence selected, for example, from the group of the alkaline phosphatase, penicillinase, lpp, or heat-stable enterotoxin II leaders. For yeast secretion, the native signal sequence may be substituted by, e.g., the yeast invertase leader, a factor leader (including *Saccharomyces* and *Kluyveromyces* alpha-factor leaders), or acid phosphatase leader, the *C. albicans* glucoamylase leader, or the signal described in PCT Publication No. WO 90/13646. In mammalian cell expression, mammalian signal sequences as well as viral secretory leaders, for example, the herpes simplex gD signal, are available. The DNA for such precursor regions may be ligated in reading frame to DNA encoding the protein.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the multivalent antibody. One useful transcription termination component is the bovine growth hormone polyadenylation region. See PCT Publication No. WO 94/11026 and the expression vector disclosed therein.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, New York, 1985), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). In some instance it will be desired to produce proteins in vertebrate cells, such as for glycosylation, and the propagation of vertebrate cells in culture (tissue culture) has become a routine procedure. Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. For many applications, the small size of the protein multimers described herein would make *E. coli* the preferred method for expression.

Protein Production

Host cells are transformed with the herein-described expression or cloning vectors for protein production and cultured in conventional nutrient media modified as appropriate for inducing promoters, selecting transformants, or amplifying the genes encoding the desired sequences.

The host cells used to produce the proteins of this invention may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al, Meth. Enz. 58:44 (1979), Barnes et al, Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Proteins disclosed herein can also be produced using cell-translation systems. For such purposes, the nucleic acids encoding the proteins must be modified to allow in vitro transcription to produce mRNA and to allow cell-free translation of the mRNA in the particular cell-free system being utilized. Exemplary eukaryotic cell-free translation systems include, for example, mammalian or yeast cell-free translation systems, and exemplary prokaryotic cell-free translation systems include, for example, bacterial cell-free translation systems.

Proteins disclosed herein can also be produced by chemical synthesis (e.g., by the methods described in Solid Phase Peptide Synthesis, 2nd ed., 1984, The Pierce Chemical Co., Rockford, IL). Modifications to the protein can also be produced by chemical synthesis.

The proteins disclosed herein can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, proteins may be exchanged into different buffers and/or concentrated by any of a variety of methods known to the art, including, but not limited to, filtration and dialysis.

The purified proteins are preferably at least 85% pure, more preferably at least 95% pure, and most preferably at least 98% pure. Regardless of the exact numerical value of the purity, the proteins are sufficiently pure for use as a pharmaceutical product.

Imaging, Diagnostic and Other Applications

The FN3 domain fusions provided herein may be used to treat a variety of diseases and disorders, based on the identity of the heterogenous molecule fused to the described FN3 domains. The applications for the FN3 domain fusions may be determined by the skilled artisan based on the knowledge in the art and the information provided herein. Uses for various FN3 domain fusion proteins are described in detail herein. FN3 domain fusions may be administered to any mammalian subject or patient, including both human and non-human organisms.

The serum albumin binders and fusion molecules described herein can be detectably labeled and used to contact cells expressing, e.g., a protein bound by the fusion molecule for imaging or diagnostic applications. Any method known in the art for conjugating a protein to the detectable moiety may be employed, including those methods described by Hunter, et al, Nature 144:945 (1962); David, et al, Biochemistry 13: 1014 (1974); Pain, et al, J. Immunol. Meth. 40:219 (1981); and Nygren, J. Histochem. and Cytochem. 30:407 (1982).

In certain embodiments, the serum albumin binders and fusion molecules described herein are further attached to a label that is able to be detected (e.g., the label can be a radioisotope, fluorescent compound, enzyme or enzyme co-factor). The label may be a radioactive agent, such as: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{123}$I, $^{125}$I, $^{13}$T, $^{132}$I, or $^{99}$Tc. A serum albumin binder or fusion molecule affixed to such a moiety may be used as an imaging agent and is administered in an amount effective for diagnostic use in a mammal such as a human and the localization and accumulation of the imaging agent is then detected. The localization and accumulation of the imaging agent may be detected by radioscintigraphy, nuclear magnetic resonance imaging, computed tomography or positron emission tomography. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety.

Serum albumin binders and fusion molecules also are useful as affinity purification agents. In this process, the proteins are immobilized on a suitable support, such a Sephadex resin or filter paper, using methods well known in the art. The proteins can be employed in any known assay method, such as competitive binding assays, direct and indirect sandwich assays, and immunoprecipitation assays (Zola, Monoclonal Antibodies: A Manual of Techniques, pp. 147-158 (CRC Press, Inc., 1987)). Exemplary Therapeutic Formulations and Modes of Administration The present invention provides methods for administering a therapeutic moiety fused to a described FN3 domain, wherein the half-life of the therapeutic moiety is extended when fused to the described FN3 domains. Techniques and dosages for administration of the fusion constructs will vary depending on the type of therapeutic moiety fused to the described FN3 domains and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA). In certain embodiments, pharmaceutical formulations of described FN3 domains and their fusion molecules comprise, e.g., 1-20 mM succinic acid, 2-10% sorbitol, and 1-10% glycine at pH 4.0-7.0. In an exemplary embodiment, pharmaceutical formulations of the described FN3 domain and their fusion molecules comprise, e.g., 10 mM succinic acid, 8% sorbitol, and 5% glycine at pH 6.0.

In some embodiments, the described FN3 domains and fusions thereof are pharmaceutically acceptable to a mammal, in particular a human. A "pharmaceutically acceptable" polypeptide refers to a polypeptide that is administered to an animal without significant adverse medical consequences. Examples of pharmaceutically acceptable FN3 domains disclosed herein and fusions thereof include FN3 domains that lack the integrin-binding domain (RGD) and compositions that are essentially endotoxin free or have very low endotoxin levels.

Therapeutic compositions may be administered with a pharmaceutically acceptable diluent, carrier, or excipient, in unit dosage form. Administration may be parenteral (e.g., intravenous, subcutaneous), oral, or topical, as non-limiting examples. The composition can be in the form of a pill, tablet, capsule, liquid, or sustained release tablet for oral administration; a liquid for intravenous, subcutaneous or parenteral administration; or a gel, lotion, ointment, cream, or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, PA). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The polypeptide may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

A therapeutically effective dose refers to a dose that produces the therapeutic effects for which it is administered. The exact dose will depend on the disorder to be treated, and may be ascertained by one skilled in the art using known techniques. In general, the FN3 domain fusion is administered at about 0.01 µg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or less frequently (e.g., once every other day, once or twice weekly, or monthly). In addition, as is known in the art, adjustments for age as well as the body weight, general health, sex, diet, time of administration, drug interaction, and the severity of the disease may be necessary, and will be ascertainable with routine experimentation by those skilled in the art.

Kits for Detecting Human Serum Albumin

Provided herein are kits for detecting human serum albumin in a biological sample. These kits include one or more of the serum albumin-binding FN3 domains described herein and instructions for use of the kit.

The provided serum albumin-binding FN3 domain may be in solution; lyophilized; affixed to a substrate, carrier, or plate; or detectably labeled.

The described kits may also include additional components useful for performing the methods described herein. By way of example, the kits may comprise means for obtaining a sample from a subject, a control or reference sample, e.g., a sample from a subject having slowly progressing cancer and/or a subject not having cancer, one or more sample compartments, and/or instructional material which describes performance of a method of the invention and tissue specific controls or standards.

The means for determining the level of serum albumin can further include, for example, buffers or other reagents for use in an assay for determining the level of serum albumin. The instructions can be, for example, printed instructions for performing the assay and/or instructions for evaluating the level of serum albumin.

The described kits may also include means for isolating a sample from a subject. These means can comprise one or more items of equipment or reagents that can be used to obtain a fluid or tissue from a subject. The means for obtaining a sample from a subject may also comprise means for isolating blood components, such as serum, from a blood sample. Preferably, the kit is designed for use with a human subject.

Embodiments described herein are directed to methods of detecting the presence of human serum albumin in a biological sample comprising contacting the biological sample with a serum albumin-binding FN3 domain described herein and evaluating the binding of the biological sample to the protein.

Embodiments described herein are directed to methods of extending the half-life of a target molecule in a human subject, the method comprising conjugating a serum albumin-binding FN3 domain described herein to the target molecule, thereby extending the half-life of the target molecule in a human subject. In some embodiments, the method further comprises administering the conjugated molecule to a human. In some embodiments, the target molecule is a drug, an antibody, a FN3 domain that binds to molecule other than human serum albumin, or a toxin. In some embodiments, the conjugation is a peptide linker. In some embodiments, the peptide linker comprises a sequence of (GS)2, (SEQ ID NO: 71), (GGGS)2 (SEQ ID NO: 72), (GGGGS)5 (SEQ ID NO: 73), (AP)2 (SEQ ID NO: 74), (AP)5 (SEQ ID NO: 75), (AP)10 (SEQ ID NO: 76), (AP)20 (SEQ ID NO: 77) and A(EAAAK)5AAA (SEQ ID NO: 78).

EXAMPLES

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

Example 1. Construction of Tencon Libraries with Randomized Loops

Tencon (SEQ ID NO: 1) is an immunoglobulin-like scaffold, fibronectin type III (FN3) domain, designed from a consensus sequence of fifteen FN3 domains from human tenascin-C (Jacobs et al., Protein Engineering, Design, and Selection, 25:107-117, 2012; U.S. Pat. No. 8,278,419). The crystal structure of Tencon shows six surface-exposed loops that connect seven beta-strands. These loops, or selected residues within each loop, can be randomized in order to construct libraries of fibronectin type III (FN3) domains that can be used to select novel molecules that bind to specific targets.

Tencon:

```
                                              (SEQ ID NO 1)
LPAPKNLVVSEVTEDSLRLSWTAPDAAFDSFLIQYQESEKVGEAINLTVP

GSERSYDLTGLKPGTEYTVSIYGVKGGHRSNPLSAEFTT:
```

Various libraries were generated using the tencon scaffold and various design strategies. In general, libraries TCL1 and TCL2 produced good binders. Generation of TCL1 and TCL2 libraries are described in detail in Int. Pat. Publ. No. WO2014081944A2.

Construction of TCL1 Library

A library designed to randomize only the FG loop of Tencon (SEQ ID NO: 1), TCL1, was constructed for use with the cis-display system (Jacobs et al., Protein Engineering, Design, and Selection, 25:107-117, 2012). In this system, a double-stranded DNA incorporating sequences for a Tac promoter, Tencon library coding sequence, RepA coding sequence, cis-element, and on element is produced. Upon expression in an in vitro transcription/translation system, a complex is produced of the Tencon-RepA fusion protein bound in cis to the DNA from which it is encoded. Complexes that bind to a target molecule are then isolated and amplified by polymerase chain reaction (PCR), as described below.

Construction of the TCL1 library for use with cis-display was achieved by successive rounds of PCR to produce the final linear, double-stranded DNA molecules in two halves; the 5' fragment contains the promoter and Tencon sequences, while the 3' fragment contains the repA gene and the cis- and on elements. These two halves are combined by restriction digest in order to produce the entire construct. The TCL1 library was designed to incorporate random amino acids only in the FG loop of Tencon, KGGHRSN (SEQ ID NO: 32). NNS codons were used in the construction of this library, resulting in the possible incorporation of all 20 amino acids and one stop codon into the FG loop. The TCL1 library contains six separate sub-libraries, each having a different randomized FG loop length, from 7 to 12 residues, in order to further increase diversity.

TCL1 library
(SEQ ID NO: 2)
LPAPKNLVVSEVTEDSLRLSWTAPDAAFDSFLIQYQESEKVGEAINLTVP

GSERSYDLTGLKPGTEYTVSIYGVX$_{7-12}$PLSAEFTT;

wherein
$X_1$, $X_2$, $X_3$, $X_4$, $X_5$, $X_6$, $X_7$ is any amino acid; and
$X_8$, $X_9$, $X_{10}$, $X_{11}$ and $X_{12}$ are any amino acid or deleted Construction of TCL2 Library TCL2 library was constructed in which both the BC and the FG loops of Tencon were randomized and the distribution of amino acids at each position was strictly controlled. Table 2 shows the amino acid distribution at desired loop positions in the TCL2 library. The designed amino acid distribution had two aims. First, the library was biased toward residues that were predicted to be structurally important for Tencon folding and stability based on analysis of the Tencon crystal structure and/or from homology modeling. For example, position 29 was fixed to be only a subset of hydrophobic amino acids, as this residue was buried in the hydrophobic core of the Tencon fold. A second layer of design included biasing the amino acid distribution toward that of residues preferentially found in the heavy chain HCDR3 of antibodies, to efficiently produce high-affinity binders (Birtalan et al., J Mol Biol 377:1518-28, 2008; Olson et al., Protein Sci 16:476-84, 2007). Towards this goal, the "designed distribution" in Table 2 refers to the distribution as follows: 6% alanine, 6% arginine, 3.9% asparagine, 7.5% aspartic acid, 2.5% glutamic acid, 1.5% glutamine, 15% glycine, 2.3% histidine, 2.5% isoleucine, 5% leucine, 1.5% lysine, 2.5% phenylalanine, 4% proline, 10% serine, 4.5% threonine, 4% tryptophan, 17.3% tyrosine, and 4% valine. This distribution is devoid of methionine, cysteine, and STOP codons.

TCL2 library
(SEQ ID NO: 3)
LPAPKNLVVSEVTEDSLRLSWX$_1$X$_2$X$_3$X$_4$X$_5$X$_6$X$_7$X$_8$SFLIQYQESEKVG

EAINLTVPGSERSYDLTGLKPGTEYTVSIYGVX$_9$X$_{10}$X$_{11}$X$_{12}$X$_{13}$SX$_{14}$

X$_{15}$LSAEFTT;
wherein $X_1$ is Ala, Arg, Asn, Asp, Glu, Gln, Gly, His, Ile, Leu, Lys, Phe, Pro, Ser, Thr, Trp, Tyr or Val;

$X_2$ is Ala, Arg, Asn, Asp, Glu, Gln, Gly, His, Ile, Leu, Lys, Phe, Pro, Ser, Thr, Trp, Tyr or Val;

$X_3$ Ala, Arg, Asn, Asp, Glu, Gln, Gly, His, Ile, Leu, Lys, Phe, Pro, Ser, Thr, Trp, Tyr or Val;

$X_4$ is Ala, Arg, Asn, Asp, Glu, Gln, Gly, His, Ile, Leu, Lys, Phe, Pro, Ser, Thr, Trp, Tyr or Val;

$X_5$ is Ala, Arg, Asn, Asp, Glu, Gln, Gly, His, Ile, Leu, Lys, Phe, Pro, Ser, Thr, Trp, Tyr or Val;

$X_6$ is Ala, Arg, Asn, Asp, Glu, Gln, Gly, His, Ile, Leu, Lys, Phe, Pro, Ser, Thr, Trp, Tyr or Val;

$X_7$ is Phe, Ile, Leu, Val or Tyr;

$X_8$ is Asp, Glu or Thr;

$X_9$ is Ala, Arg, Asn, Asp, Glu, Gln, Gly, His, Ile, Leu, Lys, Phe, Pro, Ser, Thr, Trp, Tyr or Val;

$X_{10}$ is Ala, Arg, Asn, Asp, Glu, Gln, Gly, His, Ile, Leu, Lys, Phe, Pro, Ser, Thr, Trp, Tyr or Val;

$X_{11}$ is Ala, Arg, Asn, Asp, Glu, Gln, Gly, His, Ile, Leu, Lys, Phe, Pro, Ser, Thr, Trp, Tyr or Val;

$X_{12}$ is Ala, Arg, Asn, Asp, Glu, Gln, Gly, His, Ile, Leu, Lys, Phe, Pro, Ser, Thr, Trp, Tyr or Val;

$X_{13}$ is Ala, Arg, Asn, Asp, Glu, Gln, Gly, His, Ile, Leu, Lys, Phe, Pro, Ser, Thr, Trp, Tyr or Val;

$X_{14}$ is Ala, Arg, Asn, Asp, Glu, Gln, Gly, His, Ile, Leu, Lys, Phe, Pro, Ser, Thr, Trp, Tyr or Val;
and $X_{15}$ is Ala, Arg, Asn, Asp, Glu, Gln, Gly, His, Ile, Leu, Lys, Phe, Pro, Ser, Thr, Trp, Tyr or Val.

TABLE 2

| Residue Position* | T residues | Distribution in the TCL2 library |
|---|---|---|
| 2 | T | designed distribution |
| 3 | A | designed distribution |
| 4 | P | 50% P + designed distribution |
| 5 | D | designed distribution |
| 6 | A | 20% A + 20% G + designed distribution |
| 7 | A | designed distribution |
| 8 | F | 20% F, 20% I, 20% L, 20% V, 20% Y |

TABLE 2-continued

| Residue Position* | T residues | Distribution in the TCL2 library |
|---|---|---|
| 9 | D | 33% D, 33% E, 33% T |
| 5 | K | designed distribution |
| 6 | G | designed distribution |
| 7 | G | designed distribution |
| 8 | H | designed distribution |
| 9 | R | designed distribution |
| 10 | S | 100% S |
| 11 | N | designed distribution |
| 12 | P | 50% P + designed distribution |

*residue numbering is based on Tencon sequence of SEQ ID NO: 1

Subsequently, these libraries were improved by various ways, including building of the libraries on a stabilized Tencon framework (U.S. Pat. No. 8,569,227) that incorporates substitutions E11R/L17A/N46V/E86I (Tencon27; SEQ ID NO: 4) when compared to the wild type tencon as well as altering of the positions randomized in the BC and FG loops. Tencon27 is described in Int. Pat. Appl. No. WO2013049275. From this, new libraries designed to randomize only the FG loop of Tencon (library TCL9), or a combination of the BC and FG loops (library TCL7) were generated. These libraries were constructed for use with the cis-display system (Odegrip et al., Proc Natl Acad Sci USA 101: 2806-2810, 2004). The details of this design are shown below:

```
Stabilized Tencon (Tencon27)
                                        (SEQ ID NO: 4)
LPAPKNLVVSRVTEDSARLSWTAPDAAFDSFLIQYQESEKVGEAIVLTV

PGSERSYDLTGLKPGTEYTVSIYGVKGGHRSNPLSAIFTT

TCL7 (randomized FG and BC loops)
                                        (SEQ ID NO: 5)
LPAPKNLVVSRVTEDSARLSWX₁X₂X₃X₄X₅X₆X₇X₈X₉FDSFLIQYQESEK

VGEAIVLTVPGSERSYDLTGLKPGTEYTVSIYGVX₁₀X₁₁X₁₂X₁₃X₁₄X₁₅

X₁₆X₁₇X₁₈X₁₉SNPLSAIFTT;
wherein

X₁, X₂, X₃, X₄, X₅, X₆, X₁₀, X₁₁, X₁₂, X₁₃, X₁₄, X₁₅ and X₁₆ is A, D, E, F, G, H, I, K, L, N, P, Q, R,

S, T, V, W or Y;
and

X₇, X₈, X₉, X₁₇, X₁₈ and X₁₉, is A, D, E, F, G, H,

I, K, L, N, P, Q, R, S, T, V, W, Y or deleted.

TCL9 (randomized FG loop)
                                        (SEQ ID NO: 6)
LPAPKNLVVSRVTEDSARLSWTAPDAAFDSFLIQYQESEKVGEAIVLTV

PGSERSYDLTGLKPGTEYTVSIYGV X₁X₂X₃X₄X₅X₆X₇X₈X₉ X₁₀X₁₁X₁₂

SNPLSAIFTT; X₁, X₂, X₃, X₄, X₅, X₆ and X₇, is A, D,

E, F, G, H, I, K, L, N, P, Q, R, S, T, V, W or Y;
and

X₈, X₉, X₁₀, X₁₁ and X₁₂ is A, D, E, F, G, H, I, K,

L, N, P, Q, R, S, T, V, W, Y or deleted.
```

For library construction, DNA fragments encoding randomized BC loops (lengths 6-9 positions) or FG loops (lengths 7-12 positions) were synthesized using Slonomics technology (Sloning Biotechnology GmbH) so as to control the amino acid distribution of the library and to eliminate stop codons. Two different sets of DNA molecules randomizing either the BC loop or the FG loops were synthesized independently and later combined using PCR to produce the full library product.

Construction of FG Loop Libraries (TCL9)

A set of synthetic DNA molecules consisting of a 5' Tac promoter followed by the complete gene sequence of Tencon with the exception of randomized codons in the FG loop was produced (SEQ ID NOs: 26-31). For FG loop randomization, all amino acids except cysteine and methionine were encoded at equal percentages. The lengths of the diversified portion are such that they encode for 7, 8, 9, 10, 11, or 12 amino acids in the FG loop. Sub-libraries of each length variation were synthesized individually at a scale of 2 ug and then amplified by PCR using oligos Sloning-FOR (SEQ ID NO: 9) and Sloning-Rev (SEQ ID NO: 10).

The 3' fragment of the library is a constant DNA sequence containing elements for display, including a PspOMI restriction site, the coding region of the repA gene, and the cis- and on elements. PCR reactions were performed to amplify this fragment using a plasmid (pCR4Blunt) (Invitrogen) as a template with M13 Forward and M13 Reverse primers. The resulting PCR products were digested by PspOMI overnight and gel-purified. To ligate the 5' portion of library DNA to the 3' DNA containing repA gene, 2 pmol (~540 ng to 560 ng) of 5' DNA was ligated to an equal molar (~1.25 μg) of 3' repA DNA in the presence of NotI and PspOMI enzyme and T4 ligase at 37° C. overnight. The ligated library product was amplified by using 12 cycles of PCR with oligos POP2250 (SEQ ID NO: 11) and DigLigRev (SEQ ID NO: 12). For each sub-library, the resulting DNA from 12 PCR reactions were combined and purified by Qiagen spin column. The yield for each sub-library of TCL9 ranged from 32-34 μg.

Construction of FG/BC Loop Libraries (TCL7)

The TCL7 library provides for a library with randomized Tencon BC and FG loops. In this library, BC loops of lengths 6-9 amino acids were mixed combinatorially with randomized FG loops of 7-12 amino acids in length. Synthetic Tencon fragments BC6, BC7, BC8, and BC9 (SEQ ID NO: 13-16) were produced to include the Tencon gene encoding for the N-terminal portion of the protein up to and including residue VX such that the BC loop is replaced with either 6, 7, 8, or 9 randomized amino acids. These fragments were synthesized prior to the discovery of L17A, N46V and E83I mutations (CEN5243) but these mutations were introduced in the molecular biology steps described below. In order to combine this fragment with fragments encoding for randomized FG loops, the following steps were taken.

First, a DNA fragment encoding the Tac promoter and the 5' sequence of Tencon up to the nucleotide encoding for amino acid A17 (130mer-L17A, SEQ ID NO: 17) was produced by PCR using oligos POP2222ext (SEQ ID NO: 18) and LS1114 (SEQ ID NO: 19). This was done to include the L17A mutation in the library (CEN5243). Next, DNA fragments encoding for Tencon residues R18-V75 including randomized BC loops were amplified by PCR using BC6, BC7, BC8, or BC9 as a templates and oligos LS1115 (SEQ ID NO: 20) and LS1117 (SEQ ID NO: 21). This PCR step introduced a BsaI site at the 3' end. These DNA fragments were subsequently joined by overlapping PCR using oligos POP2222ext and LS1117 as primers. The resulting PCR product of 240 bp was pooled and purified by Qiagen PCR purification kit. The purified DNA was digested with BsaI-HF and gel purified.

Fragments encoding the FG loop were amplified by PCR using FG7 (SEQ ID NO: 31), FG8 (SEQ ID NO: 30), FG9 (SEQ ID NO: 29), FG10 (SEQ ID NO: 28), FG11 (SEQ ID NO: 27), and FG12 (SEQ ID NO: 26) as templates with oligonucleotides SDG10 (SEQ ID NO: 22) and SDG24 (SEQ ID NO: 23) to incorporate a BsaI restriction site and N46V and E86I variations (CEN5243).

The digested BC fragments and FG fragments were ligated together in a single step using a 3-way ligation. Four ligation reactions in the 16 possible combinations were set up, with each ligation reaction combining two BC loop lengths with 2 FG loop lengths. Each ligation contained ~300 ng of total BC fragment and 300 ng of the FG fragment. These 4 ligation pools were then amplified by PCR using oligos POP2222 (SEQ ID NO: 24) and SDG28 (SEQ ID NO: 25). 7.5 µg of each reaction product were then digested with Not1 and cleaned up with a Qiagen PCR purification column. 5.2 µg of this DNA, was ligated to an equal molar amount of RepA DNA fragment (~14 µg) digested with PspOMI and the product amplified by PCR using oligos POP2222.

Example 2: Generation of Tencon Libraries Having Alternative Binding Surfaces The choice of residues to be randomized in a particular library design governs the overall shape of the interaction surface created. X-ray crystallographic analysis of an FN3 domain containing scaffold protein selected to bind maltose binding protein (MBP) from a library in which the BC, DE, and FG loops were randomized was shown to have a largely curved interface that fits into the active site of MBP (Koide et al., Proc Natl Acad Sci USA 104: 6632-6637, 2007). In contrast, an ankyrin repeat scaffold protein that was selected to bind to MBP was found to have a much more planar interaction surface and to bind to the outer surface of MBP distant from the active (Binz et al., Nat Biotechnol 22: 575-582, 2004). These results suggest that the shape of the binding surface of a scaffold molecule (curved vs. flat) may dictate what target proteins or specific epitopes on those target proteins are able to be bound effectively by the scaffold. Published efforts around engineering protein scaffolds containing FN3 domains for protein binding has relied on engineering adjacent loops for target binding, thus producing curved binding surfaces. This approach may limit the number of targets and epitopes accessible by such scaffolds.

Tencon and other FN3 domains contain two sets of CDR-like loops lying on the opposite faces of the molecule, the first set formed by the BC, DE, and FG loops, and the second set formed by the AB, CD, and EF loops. The two sets of loops are separated by the beta-strands that form the center of the FN3 structure. If the image of the Tencon is rotated by 90 degrees, an alternative surface can be visualized. This slightly concave surface is formed by the CD and FG loops and two antiparallel beta-strands, the C and the F beta-strands, and is herein called the C-CD-F-FG surface. The C-CD-F-FG surface can be used as a template to design libraries of protein scaffold interaction surfaces by randomizing a subset of residues that form the surface. Beta-strands have a repeating structure with the side chain of every other residue exposed to the surface of the protein. Thus, a library can be made by randomizing some or all surface exposed residues in the beta strands. By choosing the appropriate residues in the beta-strands, the inherent stability of the Tencon scaffold should be minimally compromised while providing a unique scaffold surface for interaction with other proteins.

Library TCL14 (SEQ ID NO: 7), was designed into Tencon27 scaffold (SEQ ID NO: 4).

A full description of the methods used to construct this library is described in US. Pat. Publ. No. US2013/0226834.

```
TCL14 library (SEQ ID NO: 7):
LPAPKNLVVSRVTEDSARLSWTAPDAAFDSFX₁IX₂YX₃EX₄X₅X₆X₇GEAI

VLTVPGSERSYDLTGLKPGTEYX₈VX₉IX₁₀GVKGGX₁₁X₁₂SX₁₃PLSAIFT

T;
Wherein

X₁, X₂, X₃, X₄, X₅, X₆, X₁₀, X₁₁, X₁₂ and X₁₃ are A, D,

E, F, G, H, I, K, L, N, P, Q, R, S, T, V, W, Y, or

M.
```

The two beta strands forming the C-CD-F-FG surface in Tencon27 have a total of 9 surface exposed residues that could be randomized; C-strand: S30, L32, Q34, Q36; F-strand: E66, T68, S70, Y72, and V74, while the CD loop has 6 potential residues: S38, E39, K40, V41, G42, and E43 and the FG loop has 7 potential residues: K75, G76, G77, H78, R79, S80, and N81. Select residues were chosen for inclusion in the TCL14 design due to the larger theoretical size of the library if all 22 residues were randomized.

Thirteen positions in Tencon were chosen for randomizing: L32, Q34 and Q36 in C-strand, S38, E39, K40 and V41 in CD-loop, T68, S70 and Y72 in F-strand, H78, R79, and N81 in FG-loop. In the C and F strands S30 and E66 were not randomized as they lie just beyond the CD and FG loops and do not appear to be as apparently a part of the C-CD-F-FG surface. For the CD loop, G42 and E43 were not randomized as glycine, providing flexibility, can be valuable in loop regions, and E43 lies at the junction of the surface. The FG loop had K75, G76, G77, and S80 excluded. The glycines were excluded for the reasons above while careful inspection of the crystal structures revealed S80 making key contacts with the core to help form the stable FG loop. K75 faces away from the surface of the C-CD-F-FG surface and was a less appealing candidate for randomization. Although the above mentioned residues were not randomized in the original TCL14 design, they could be included in subsequent library designs to provide additional diversity for de novo selection or for example for an affinity maturation library on a select TCL14 target specific hit.

Subsequent to the production of TCL14, 3 additional Tencon libraries of similar design were produced. These two libraries, TCL19, TCL21 and TCL23, are randomized at the same positions as TCL14 (see above) however the distribution of amino acids occurring at these positions is altered (Table 3). TCL19 and TCL21 were designed to include an equal distribution of 18 natural amino acids at every position (5.55% of each), excluding only cysteine and methionine. TCL23 was designed such that each randomized position approximates the amino acid distribution found in the HCDR3 loops of functional antibodies (Birtalan et al., J Mol Biol 377: 1518-1528, 2008) as described in Table 2. As with the TCL21 library, cysteine and methionine were excluded.

A third additional library was built to expand potential target binding surface of the other libraries library. In this library, TCL24, 4 additional Tencon positions were randomized as compared to libraries TCL14, TCL19, TCL21, and TCL23. These positions include N46 and T48 from the D strand and S84 and I86 from the G strand. Positions 46, 48, 84, and 86 were chosen in particular as the side chains of these residues are surface exposed from beta-strands D and G and lie structurally adjacent to the randomized portions of the C and F strand, thus increasing the surface area accessible for binding to target proteins. The amino acid distribution used at each position for TCL24 is identical to that described for TCL19 and TCL21 in Table 3.

```
TCL24 Library
                                              (SEQ ID NO: 8)
LPAPKNLVVSRVTEDSARLSWTAPDAAFDSFX₁IX₂YX₃EX₄X₅X₆X₇GEAI

X₈LX₉VPGSERSYDLTGLKPGTEYX₁₀VX₁₁IX₁₂GVKGGX₁₃X₁₄SX₁₅PLX₁₆

AX₁₇FTT;
wherein

X₁, X₂, X₃, X₄, X₅, X₆, X₁₀, X₁₁, X₁₂ and X₁₃ are A,

D, E, F, G, H, I, K, L, N, P, Q, R, S, T, V or W.
```

TABLE 3

Amino acid frequency (%) at each randomized position for TCL21, TCL23, and TCL24.

| Amino Acid | TCL19 | TCL21 | TCL23 | TCL24 |
|---|---|---|---|---|
| Ala | 5.6 | 5.6 | 6.0 | 5.6 |
| Arg | 5.6 | 5.6 | 6.0 | 5.6 |
| Asn | 5.6 | 5.6 | 3.9 | 5.6 |
| Asp | 5.6 | 5.6 | 7.5 | 5.6 |
| Cys | 0.0 | 0.0 | 0.0 | 0.0 |
| Gln | 5.6 | 5.6 | 1.5 | 5.6 |
| Glu | 5.6 | 5.6 | 2.5 | 5.6 |
| Gly | 5.6 | 5.6 | 15.0 | 5.6 |
| His | 5.6 | 5.6 | 2.3 | 5.6 |
| Ile | 5.6 | 5.6 | 2.5 | 5.6 |
| Leu | 5.6 | 5.6 | 5.0 | 5.6 |
| Lys | 5.6 | 5.6 | 1.5 | 5.6 |
| Met | 0.0 | 0.0 | 0.0 | 0.0 |
| Phe | 5.6 | 5.6 | 2.5 | 5.6 |
| Pro | 5.6 | 5.6 | 4.0 | 5.6 |
| Ser | 5.6 | 5.6 | 10.0 | 5.6 |
| Thr | 5.6 | 5.6 | 4.5 | 5.6 |
| Trp | 5.6 | 5.6 | 4.0 | 5.6 |
| Tyr | 5.6 | 5.6 | 17.3 | 5.6 |
| Val | 5.6 | 5.6 | 4.0 | 5.6 |

Generation of TCL21, TCL23, and TCL24 Libraries

The TCL21 library was generated using Colibra library technology (Isogenica) in order to control amino acid distributions. TCL19, TCL23, and TCL24 gene fragments were generated using Slonomics technology (Morphosys) to control amino acid distributions. PCR was used to amplify each library following initial synthesis followed by ligation to the gene for RepA in order to be used in selections using the CIS-display system (Odegrip et al., Proc Natl Acad Sci USA 101: 2806-2810, 2004) as described above for the loop libraries.

Example 3: Selection of Fibronectin Type III (FN3) Domains that Bind Human Serum Albumin Library Screening Cis-display was used to select human serum albumin binding domains from the TCL14, TCL19, TCL21, TCL23, and TCL24 libraries. Recombinant human and cyno serum albumin and human albumin domain II (Albumin Biosciences) was biotinylated using standard methods and used for panning. For in vitro transcription and translation (ITT), 3 µg of library DNA were incubated with 0.1 mM complete amino acids, 1×S30 premix components, and 15 µL of S30 extract (Promega) in a total volume of 50 µL and incubated at 30° C. After 1 hour, 375 µL of blocking solution ((0.1% Casein (Thermo Fisher, Rockford, IL), 100 mg/ml Herring Sperm DNA (Promega, Madison, WI), 1 mg/mL heparin (Sigma-Aldrich, St. Louis, MO)) was added and the reaction was incubated on ice for 15 minutes. For selection, biotinylated antigen was added at concentrations of 400 nM (Round 1), 200 nM (Rounds 2 and 3) and 100 nM (Rounds 4 and 5). Bound library members were recovered using neutravidin magnetic beads (Thermo Fisher, Rockford, IL) (Rounds 1, 3, and 5) or streptavidin magnetic beads (Promega, Madison, WI) (Rounds 2 and 4) and unbound library members were removed by washing the beads 5-14 times with 500 µL PBST followed by 2 washes with 500 µL PBS. Additional selection rounds were performed in order to identify FN3 domain molecules with improved affinities. Briefly, outputs from round 5 were prepared as described above and subjected to additional iterative rounds of selection with the following changes: incubation with biotinylated antigen was decreased from 1 hour to 15 minutes and bead capture was decreased from 20 minutes to 15 minutes, bt-HSA decreased to 25 nM (Rounds 6 and 7) or 2.5 nM (Rounds 8 and 9), and an additional 1 hour wash was performed in the presence of an excess of non-biotinylated target protein. The goal of these changes was to simultaneously select for binders with a potentially faster on-rate and a slower off-rate yielding a substantially lower $K_D$.

Following panning, selected FN3 domains were amplified by PCR using oligos Tcon6 (SEQ ID NO: 33) and Tcon5shortE86I (SEQ ID NO: 34), subcloned by annealing into a pET15-LIC and transformed into BL21-GOLD (DE3) cells (Agilent, Santa Clara, CA) for soluble expression in *E. coli* using standard molecular biology techniques. Single clones were picked and grown to saturation in 1 mL LB with ampicillin in 96 deepwell plates at 37° C. The following day, 25 uL was transferred to fresh 1 mL LB-Amp media in 96 deepwell plates and grown at 37° C. for 2 hours. IPTG was added at 1 mM final concentration and protein expression was induced at 30° C. for 16 hours. The cells were harvested by centrifugation and subsequently lysed with Bugbuster HT (EMD Chemicals, Gibbstown, NJ) supplemented with 0.2 mg/mL final Chicken Egg White Lysozyme (Sigma-Aldrich, St. Louis, MO). Bacterial lysates were clarified by centrifugation and supernatants were transferred to new 96 deepwell plates and tested for binding to the target protein by ELISA.

Selection of FN3 Domains that Bind Human Serum Albumin

An enzyme linked immunosorbant assay (ELISA) was performed on individual clones from selected panning outputs to identify Human Serum Albumin Binders. Maxisorp plates (Nunc, Rochester, NY) were coated with either 5 ug HSA, cynomolgous SA or 5 ug/ml Fc overnight (Sigma-Aldrich, St. Louis, MO), washed with Tris-Buffered Saline, pH 7.4 with 0.05% Tween-20 (TBST) and blocked using Starting Block T20 (Thermo Fisher, Rockford, IL). Clarified bacterial lysates (described above) were applied onto the wells of the coated HSA, cSA and Fc plates. Plates were incubated for 1 hour, washed with TBST and bound Centyrin was detected with anti-V5 tag antibody and POD chemiluminescent substrate (Roche, Indianapolis, IN) using a Molecular Devices M5 plate reader. Hits were defined as Binding Signal for Human and Cynomolgous Serum Albumin over Binding Signal for Fc >10.

One FN3 domain, B7, demonstrated significant binding to human and cyno albumin and to domain II of human albumin as shown in Table 4 below. Residues important for binding to human SA were further characterized by preparing variants where each residue in the putative binding site was individually mutated to alanine. Table 5 shows the full amino sequences of the domain II binding FN3 domain and alanine variants. SEQ ID NO: 51 was compared to the sequence of H9 (SEQ ID NO: 70) and found to have a significant increase in half-life in cynomologus monkeys. This was unexpected.

TABLE 4

| Clone | SEQ ID | HSA (RLU) | cSA (RLU) | HSA domain II (RLU) | HSA/Fc (RLU) | cSA/Fc (RLU) | HSA domain II/Fc (RLU) |
|---|---|---|---|---|---|---|---|
| B7 | 51 | 82400 | 863550 | 118250 | 34 | 360 | 49 |

TABLE 5

Amino Acid Sequences of the Selected FN3 domains

| Clone | SEQ ID | SEQUENCE |
|---|---|---|
| B7 | 51 | MLPAPKNLVASRVTEDSARLSWTAPDAAFDSFNIAYWE PGIGGEAIWLRVPGSERSYDLTGLKPGTEYKVWIHGVK GGASSPPLIARFTT |
| A10V | 52 | MLPAPKNLVVSRVTEDSARLSWTAPDAAFDSFNIAYWE PGIGGEAIWLRVPGSERSYDLTGLKPGTEYKVWIHGVK GGASSPPLIARFTT |
| A10V, N33A | 53 | MLPAPKNLVVSRVTEDSARLSWTAPDAAFDSFAIAYWE PGIGGEAIWLRVPGSERSYDLTGLKPGTEYKVWIHGVK GGASSPPLIARFTT |
| A10V, A35S | 54 | MLPAPKNLVVSRVTEDSARLSWTAPDAAFDSFNISYWE PGIGGEAIWLRVPGSERSYDLTGLKPGTEYKVWIHGVK GGASSPPLIARFTT |
| A10V, W37A | 55 | MLPAPKNLVVSRVTEDSARLSWTAPDAAFDSFNIAYAE PGIGGEAIWLRVPGSERSYDLTGLKPGTEYKVWIHGVK GGASSPPLIARFTT |
| A10V, P39A | 56 | MLPAPKNLVVSRVTEDSARLSWTAPDAAFDSFNIAYWE AGIGGEAIWLRVPGSERSYDLTGLKPGTEYKVWIHGVK GGASSPPLIARFTT |
| A10V, G40A | 57 | MLPAPKNLVVSRVTEDSARLSWTAPDAAFDSFNIAYWE PAIGGEAIWLRVPGSERSYDLTGLKPGTEYKVWIHGVK GGASSPPLIARFTT |
| A10V, I41A | 58 | MLPAPKNLVVSRVTEDSARLSWTAPDAAFDSFNIAYWE PGAGGEAIWLRVPGSERSYDLTGLKPGTEYKVWIHGVK GGASSPPLIARFTT |
| A10V, G42A | 59 | MLPAPKNLVVSRVTEDSARLSWTAPDAAFDSFNIAYWE PGIAGEAIWLRVPGSERSYDLTGLKPGTEYKVWIHGVK GGASSPPLIARFTT |
| A10V, W47A | 60 | MLPAPKNLVVSRVTEDSARLSWTAPDAAFDSFNIAYWE PGIGGEAIALRVPGSERSYDLTGLKPGTEYKVWIHGVK GGASSPPLIARFTT |
| A10V, R49A | 61 | MLPAPKNLVVSRVTEDSARLSWTAPDAAFDSFNIAYWE PGIGGEAIWLAVPGSERSYDLTGLKPGTEYKVWIHGVK GGASSPPLIARFTT |
| A10V, K69A | 62 | MLPAPKNLVVSRVTEDSARLSWTAPDAAFDSFNIAYWE PGIGGEAIWLRVPGSERSYDLTGLKPGTEYAVWIHGVK GGASSPPLIARFTT |
| A10V, W71A | 63 | MLPAPKNLVVSRVTEDSARLSWTAPDAAFDSFNIAYWE PGIGGEAIWLRVPGSERSYDLTGLKPGTEYKVAIHGVK GGASSPPLIARFTT |
| A10V, H73A | 64 | MLPAPKNLVVSRVTEDSARLSWTAPDAAFDSFNIAYWE PGIGGEAIWLRVPGSERSYDLTGLKPGTEYKVWIAGVK GGASSPPLIARFTT |
| A10V, A79S | 65 | MLPAPKNLVVSRVTEDSARLSWTAPDAAFDSFNIAYWE PGIGGEAIWLRVPGSERSYDLTGLKPGTEYKVWIHGVK GGSSSPPLIARFTT |
| A10V, S80A | 66 | MLPAPKNLVVSRVTEDSARLSWTAPDAAFDSFNIAYWE PGIGGEAIWLRVPGSERSYDLTGLKPGTEYKVWIHGVK GGAASPPLIARFTT |
| A10V, P82A | 67 | MLPAPKNLVVSRVTEDSARLSWTAPDAAFDSFNIAYWE PGIGGEAIWLRVPGSERSYDLTGLKPGTEYKVWIHGVK GGASSAPLIARFTT |
| A10V, I85A | 68 | MLPAPKNLVVSRVTEDSARLSWTAPDAAFDSFNIAYWE PGIGGEAIWLRVPGSERSYDLTGLKPGTEYKVWIHGVK GGASSPPLAARFTT |
| A10V, R87A | 69 | MLPAPKNLVVSRVTEDSARLSWTAPDAAFDSFNIAYWE PGIGGEAIWLRVPGSERSYDLTGLKPGTEYKVWIHGVK GGASSPPLIAAFTT |
| ALB-H9 | 70 | LPAPKNLVVSRVTEDSARLSWTAPDAAFDSFHIEYWEQ SIVGEAIVLTVPGSERSYDLTGLKPGTEYRVWIYGVKG GNDSWPLSAIFTT |

Small Scale Expression and Purification Identified FN3 Domains Binding Human Serum Albumin Select FN3 domain clones were picked and grown to saturation in 1 mL Luria Broth (LB) supplemented with 100 ug/mL ampicillin (LB-Amp media) in 96 deep well plates at 37° C. The following day, 25 uL was transferred to fresh 5 mL LB-Amp media in 24 deep well plates and grown at 37° C. for 2 hours. IPTG was added at 1 mM final concentration and protein expression was induced at 30° C. for 16 hours. Cells were harvested by centrifugation and lysed with Bugbuster HT (EMD Chemicals, Gibbstown, NJ) supplemented with 0.2 mg/mL final chicken egg white lysozyme (Sigma-Aldrich, St. Louis, MO). Bacterial lysates were clarified by centrifugation and supernatants were transferred to new 96 deepwell plates. The His-tagged FN3 domains were purified using a 96 well Ni-NTA Multitrap Plate following the manufacturers recommendation (GE Lifesciences, Piscataway, NJ).

Size Exclusion Chromatography Analysis

Size exclusion chromatography was used to determine the aggregation state of the FN3 domains binding Human Serum Albumin. Aliquots (10 μL) of each purified FN3 domain were injected onto a Superdex 75 5/150 column (GE Healthcare) at a flow rate of 0.3 mL/min in a mobile phase of PBS pH 7.4. Elution from the column was monitored by absorbance at 280 nm. FN3 domains that exhibited high levels of aggregation by SEC were excluded from further analysis.

Example 4: Characterization of Human Serum Albumin-Binding FN3 Domains

Immunoprecipitation of Human Serum Albumin-FN3 Domain Complexes

To evaluate the functionality of binders, selected FN3 domains were tested for their ability to complex with endogenous albumin in normal serum. The method to determine this are provided in U.S. application Ser. No. 15/611, 296, which is hereby incorporated by reference. Most of the sequences even those with substitutions were found to bind with and pulldown albumin. Certain positions may not tolerate an alanine substitution but other substitutions at these positions may be made without elimination albumin interaction. The results are illustrated in Table 6.

TABLE 6

| Clone ID | SEQ ID | Pull Down (Human SA) | Pull Down (Cyno SA) |
|---|---|---|---|
| B7 | 51 | Yes | Yes |
| A10V | 52 | Yes | Yes |
| A10V, N33A | 53 | No | No |
| A10V, A35S | 54 | Yes | Yes |
| A10V, W37A | 55 | No | No |
| A10V, P39A | 56 | Yes | Yes |
| A10V, G40A | 57 | Yes | Yes |
| A10V, I41A | 58 | Yes | Yes |
| A10V, G42A | 59 | Yes | Yes |
| A10V, W47A | 60 | No | No |
| A10V, R49A | 61 | Yes | Yes |
| A10V, K69A | 62 | Yes | Yes |
| A10V, W71A | 63 | No | No |
| A10V, H73A | 64 | No | No |
| A10V, A79S | 65 | No | No |
| A10V, S80A | 66 | Yes | Yes |
| A10V, P82A | 67 | Yes | Yes |
| A10V, I85A | 68 | No | No |
| A10V, R87A | 69 | Yes | Yes |

The FN3 proteins were also tested in an ELISA assay to determine their ability to bind to immobilized human or cynomolgous albumin. The binding of 667 nM B7 and B7 variants to human or cynomolgous albumin are illustrated in Table 7. The negative control is wt Tencon.

TABLE 7

| Clone | SEQ ID | Cyno Albumin (RLU) | Human Albumin (RLU) |
|---|---|---|---|
| wt Tencon | | 775 | 8350 |
| B7 | 51 | 145250 | 97400 |
| A10V | 52 | 43550 | 23100 |
| A10V, N33A | 53 | 1500 | 2350 |
| A10V, A35S | 54 | 2950 | 2950 |
| A10V, W37A | 55 | 500 | 600 |
| A10V, P39A | 56 | 73550 | 107400 |
| A10V, G40A | 57 | 64375 | 69775 |
| A10V, I41A | 58 | 46200 | 50600 |
| A10V, G42A | 59 | 9175 | 4475 |
| A10V, W47A | 60 | 2000 | 2100 |
| A10V, R49A | 61 | 1150 | 1025 |
| A10V, K69A | 62 | 42300 | 15875 |
| A10V, W71A | 63 | 1600 | 950 |
| A10V, H73A | 64 | 600 | 550 |
| A10V, A79S | 65 | 9200 | 250 |
| A10V, S80A | 66 | 2950 | 2950 |
| A10V, P82A | 67 | 24125 | 21725 |
| A10V, I85A | 68 | 2500 | 1000 |
| A10V, R87A | 69 | 66275 | 47450 |

Pharmacokinetics of Albumin Binding FN3 Domains in Cynomolgus Monkeys:

In-vivo studies were performed with B7 and H9. Cynomolgus monkeys were were administered by intravenous (IV) bolus injection either B7 or H9 at a dose of 5 mg/kg. The methods of administration and methods for determining the concentration of the protein was determined according to the methods described in U.S. patent application Ser. No. 15/611,296, which is hereby incorporated by reference. FIGS. 1 and 2 illustrate the pharmacokinetics, including the increase of half-life of the albumin FN3 domain referred to as B7 or ALB40.

```
Sequence information

SEQ ID NO: 1 = Original Tencon Sequence
LPAPKNLVVSEVTEDSLRLSWTAPDAAFDSFLIQYQESEKVGEAINLTVPGSERSYDLTGLKPGTEYTVSIYGVKGGHRSNPLSAEFTT SEQ ID NO: 2 = TCL1 library
LPAPKNLVVSEVTEDSLRLSWTAPDAAFDSFLIQYQESEKVGEAINLTVPGSERSYDLTGLKPGTEYTVSIYGV(X)₇₋₁₂PLSAEFTT;
wherein X₁, X₂, X₃, X₄, X₅, X₆, X₇ is any amino acid; and X₈, X₉, X₁₀, X₁₁ and X₁₂ are any amino acid
or deleted SEQ ID NO: 3 = TCL2 library
LPAPKNLVVSEVTEDSLRLSWX₁X₂X₃X₄X₅X₆X₇X₈SFLIQYQESEKVGEAINLTVPGSERSYDLTGLKPGTEYTVSIYGVX₉X₁₀X₁₁X₁₂X₁₃
SX₁₄X₁₅LSAEFTT;
wherein X₁ is Ala, Arg, Asn, Asp, Glu, Gln, Gly, His, Ile, Leu, Lys, Phe, Pro, Ser, Thr, Trp, Tyr
or Val;

X₂ is Ala, Arg, Asn, Asp, Glu, Gln, Gly, His, Ile, Leu, Lys, Phe, Pro, Ser, Thr, Trp, Tyr
or Val;

X₃ Ala, Arg, Asn, Asp, Glu, Gln, Gly, His, Ile, Leu, Lys, Phe, Pro, Ser, Thr, Trp, Tyr or
Val;

X₄ is Ala, Arg, Asn, Asp, Glu, Gln, Gly, His, Ile, Leu, Lys, Phe, Pro, Ser, Thr, Trp, Tyr
or Val;

X₅ is Ala, Arg, Asn, Asp, Glu, Gln, Gly, His, Ile, Leu, Lys, Phe, Pro, Ser, Thr, Trp, Tyr
or Val;
```

| Sequence information |
| --- |

$X_6$ is Ala, Arg, Asn, Asp, Glu, Gln, Gly, His, Ile, Leu, Lys, Phe, Pro, Ser, Thr, Trp, Tyr or Val;

$X_7$ is Phe, Ile, Leu, Val or Tyr;

$X_8$ is Asp, Glu or Thr;

$X_9$ is Ala, Arg, Asn, Asp, Glu, Gln, Gly, His, Ile, Leu, Lys, Phe, Pro, Ser, Thr, Trp, Tyr or Val;

$X_{10}$ is Ala, Arg, Asn, Asp, Glu, Gln, Gly, His, Ile, Leu, Lys, Phe, Pro, Ser, Thr, Trp, Tyr or Val;

$X_{11}$ is Ala, Arg, Asn, Asp, Glu, Gln, Gly, His, Ile, Leu, Lys, Phe, Pro, Ser, Thr, Trp, Tyr or Val;

$X_{12}$ is Ala, Arg, Asn, Asp, Glu, Gln, Gly, His, Ile, Leu, Lys, Phe, Pro, Ser, Thr, Trp, Tyr or Val;

$X_{13}$ is Ala, Arg, Asn, Asp, Glu, Gln, Gly, His, Ile, Leu, Lys, Phe, Pro, Ser, Thr, Trp, Tyr or Val;

$X_{14}$ is Ala, Arg, Asn, Asp, Glu, Gln, Gly, His, Ile, Leu, Lys, Phe, Pro, Ser, Thr, Trp, Tyr or Val;
and $X_{15}$ is Ala, Arg, Asn, Asp, Glu, Gln, Gly, His, Ile, Leu, Lys, Phe, Pro, Ser, Thr, Trp, Tyr or Val.
SEQ ID NO: 4 = Stabilized Tencon (Tencon 27)
LPAPKNLVVSRVTEDSARLSWTAPDAAFDSFLIQYQESEKVGEAIVLTVPGSERSYDLTGLKPGTEYTVSIYGVKGGHRSNPLSAIFTT SEQ ID NO: 5 = TCL7 (FG and BC loops)
LPAPKNLVVSRVTEDSARLSWX$_1$X$_2$X$_3$X$_4$X$_5$X$_6$X$_7$X$_8$X$_9$FDSFLIQYQESEKVGEAIVLTVPGSERSYDLTGLKPGTEYTVSIYGVX$_{10}$X$_{11}$X$_{12}$X$_{13}$X$_{14}$X$_{15}$X$_{16}$X$_{17}$X$_{18}$X$_{19}$SNPLSAIFTT;
wherein $X_1$, $X_2$, $X_3$, $X_4$, $X_5$, $X_6$, $X_{10}$, $X_{11}$, $X_{12}$, $X_{13}$, $X_{14}$, $X_{15}$ and $X_{16}$ are A, D, E, F, G, H, I, K, L, N, P, Q, R, S, T, V, W or Y;
and $X

| Sequence information |
|---|
| SEQ ID NO: 12 = DigLigRev<br>CATGATTACGCCAAGCTCAGAA<br><br>SEQ ID NO: 13 = BC9<br>GTGACACGGCGGTTAGAACGCGGCTACAATTAATACATAACCCCATCCCCCTGTTGACAATTAATCATCGGCTCGTATAATGTGTGGAA<br>TTGTGAGCGGATAACAATTTCACACAGGAAACAGGATCTACCATGCTGCCGGCGCCGAAAAACCTGGTTGTTTCTGAAGTTACCGAAGA<br>CTCTCTGCGTCTGTCTTGGNNNNNNNNNNNNNNNNNNNNNNNNNNNNTTYGACTCTTTCCTGATCCAGTACCAGGAATCTGAAAAAGTTG<br>GTGAAGCGATCAACCTGACCGTTCCGGGTTCTGAACGTTCTTACGACCTGACCGGTCTGAAACCGGGTACCGAATACACCGTTTCTATC<br>TACGGTGTTCTTAGAAGCTTCCCAAAGGC<br><br>SEQ ID NO: 14 = BC8<br>GTGACACGGCGGTTAGAACGCGGCTACAATTAATACATAACCCCATCCCCCTGTTGACAATTAATCATCGGCTCGTATAATGTGTGGAA<br>TTGTGAGCGGATAACAATTTCACACAGGAAACAGGATCTACCATGCTGCCGGCGCCGAAAAACCTGGTTGTTTCTGAAGTTACCGAAGA<br>CTCTCTGCGTCTGTCTTGGNNNNNNNNNNNNNNNNNNNNNNNNNNNTTYGACTCTTTCCTGATCCAGTACCAGGAATCTGAAAAAGTTGGTG<br>AAGCGATCAACCTGACCGTTCCGGGTTCTGAACGTTCTTACGACCTGACCGGTCTGAAACCGGGTACCGAATACACCGTTTCTATCTAC<br>GGTGTTCTTAGAAGCTTCCCAAAGGC<br><br>SEQ ID NO: 15 = BC7<br>GTGACACGGCGGTTAGAACGCGGCTACAATTAATACATAACCCCATCCCCCTGTTGACAATTAATCATCGGCTCGTATAATGTGTGGAA<br>TTGTGAGCGGATAACAATTTCACACAGGAAACAGGATCTACCATGCTGCCGGCGCCGAAAAACCTGGTTGTTTCTGAAGTTACCGAAGA<br>CTCTCTGCGTCTGTCTTGGNNNNNNNNNNNNNNNNNNNNNNNNNNNTTYGACTCTTTCCTGATCCAGTACCAGGAATCTGAAAAGTTGGTGAAG<br>CGATCAACCTGACCGTTCCGGGTTCTGAACGTTCTTACGACCTGACCGGTCTGAAACCGGGTACCGAATACACCGTTTCTATCTACGGT<br>GTTCTTAGAAGCTTCCCAAAGGC<br><br>SEQ ID NO: 16 = BC6<br>GTGACACGGCGGTTAGAACGCGGCTACAATTAATACATAACCCCATCCCCCTGTTGACAATTAATCATCGGCTCGTATAATGTGTGGAA<br>TTGTGAGCGGATAACAATTTCACACAGGAAACAGGATCTACCATGCTGCCGGCGCCGAAAAACCTGGTTGTTTCTGAAGTTACCGAAGA<br>CTCTCTGCGTCTGTCTTGGNNNNNNNNNNNNNNNNNNNNNNNNNNTTYGACTCTTTCCTGATCCAGTACCAGGAATCTGAAAAGTTGGTGAAGCGA<br>TCAACCTGACCGTTCCGGGTTCTGAACGTTCTTACGACCTGACCGGTCTGAAACCGGGTACCGAATACACCGTTTCTATCTACGGTGTT<br>CTTAGAAGCTTCCCAAAGGC<br><br>SEQ ID NO: 17 = 130mer-L17A<br>CGGCGGTTAGAACGCGGCTACAATTAATACATAACCCCATCCCCCTGTTGACAATTAATCATCGGCTCGTATAATGTGTGGAATTGTGA<br>GCGGATAACAATTTCACACAGGAAACAGGATCTACCATGCTG<br><br>SEQ ID NO: 18 = POP222ext<br>CGG CGG TTA GAA CGC GGC TAC AAT TAA TAC<br><br>SEQ ID NO: 19 = LS1114<br>CCA AGA CAG ACG GGC AGA GTC TTC GGT AAC GCG AGA AAC AAC CAG GTT TTT CGG CGC CGG CAG CAT<br>GGT AGA TCC TGT TTC<br><br>SEQ ID NO: 20 = LS1115<br>CCG AAG ACT CTG CCC GTC TGT CTT GG<br><br>SEQ ID NO: 21 = LS1117<br>CAG TGG TCT CAC GGA TTC CTG GTA CTG GAT CAG GAA AGA GTC GAA<br><br>SEQ ID NO: 22 = SDG10<br>CATGCGGTCTCTTCCGAAAAAGTTGGTGAAGCGATCGTCCTGACCGTTCCGGGT<br><br>SEQ ID NO: 23 = SDG24<br>GGTGGTGAAGATCGCAGACAGCGGGTTAG<br><br>SEQ ID NO: 24 = POP2222<br>CGGCGGTTAGAACGCGGCTAC<br><br>SEQ ID NO: 25 = SDG28<br>AAGATCAGTTGCGGCCGCTAGACTAGAACCGCTGCCACCGCCGGTGGTGAAGATCGCAGAC<br><br>SEQ ID NO: 26 = FG12<br>GTGACACGGCGGTTAGAACGCGGCTACAATTAATACATAACCCCATCCCCCTGTTGACAATTAATCATCGGCTCGTATAATGTGTGGAA<br>TTGTGAGCGGATAACAATTTCACACAGGAAACAGGATCTACCATGCTGCCGGCGCCGAAAAACCTGGTTGTTTCTCGCGTTACCGAAGA<br>CTCTCTGCGCGTCTGTCTTGGACCGCGCCGGACGCGGCGTTCGACTCTTTCCTGATCCAGTACCAGGAATCTGAAAAAGTTGGTGAAGCGA<br>TCGTGCTGACCGTTCCGGGTTCTGAACGTTCTTACGACCTGACCGGTCTGAAACCGGGTACCGAATACACCGTTTCTATCTACGGTGTT<br>NNNNNNNNNNNNNNNNNNNNNNNNNNNNNNNNNNNTCTAACCCGCTGTCTGCGATCTTCACCACCGGCGGTCACCATCACCATCACCA<br>TGGCAGCGGTTCTAGTCTAGCGGCCGCAACTGATCTTGGC<br><br>SEQ ID NO: 27 = FG11<br>GTGACACGGCGGTTAGAACGCGGCTACAATTAATACATAACCCCATCCCCCTGTTGACAATTAATCATCGGCTCGTATAATGTGTGGAA<br>TTGTGAGCGGATAACAATTTCACACAGGAAACAGGATCTACCATGCTGCCGGCGCCGAAAAACCTGGTTGTTTCTCGCGTTACCGAAGA<br>CTCTCTGCGCGTCTGTCTTGGACCGCGCCGGACGCGGCGTTCGACTCTTTCCTGATCCAGTACCAGGAATCTGAAAAAGTTGGTGAAGCGA<br>TCGTGCTGACCGTTCCGGGTTCTGAACGTTCTTACGACCTGACCGGTCTGAAACCGGGTACCGAATACACCGTTTCTATCTACGGTGTT<br>NNNNNNNNNNNNNNNNNNNNNNNNNNNNNNNNNTCTAACCCGCTGTCTGCGATCTTCACCACCGGCGGTCACCATCACCATCACCATGG<br>CAGCGGTTCTAGTCTAGCGGCCGCAACTGATCTTGGC |

-continued

Sequence information

SEQ ID NO: 28 = FG10
GTGACACGGCGGTTAGAACGCGGCTACAATTAATACATAACCCCATCCCCCTGTTGACAATTAATCATCGGCTCGTATAATGTGTGGAA
TTGTGAGCGGATAACAATTTCACACAGGAAACAGGATCTACCATGCTGCCGGCGCCGAAAAACCTGGTTGTTTCTCGCGTTACCGAAGA
CTCTGCGCGTCTGTCTTGGACCGCGCCGGACGCGGCGTTCGACTCTTTCCTGATCCAGTACCAGGAATCTGAAAAAGTTGGTGAAGCGA
TCGTGCTGACCGTTCCGGGTTCTGAACGTTCTTACGACCTGACCGGTCTGAAACCGGGTACCGAATACACCGTTTCTATCTACGGTGTT
NNNNNNNNNNNNNNNNNNNNNNNNNNNNNNNNTCTAACCCGCTGTCTGCGATCTTCACCACCGGCGGTCACCATCACCATCACCATGGCAG
CGGTTCTAGTCTAGCGGCCGCAACTGATCTTGGC

SEQ ID NO: 29 = FG9
GTGACACGGCGGTTAGAACGCGGCTACAATTAATACATAACCCCATCCCCCTGTTGACAATTAATCATCGGCTCGTATAATGTGTGGAA
TTGTGAGCGGATAACAATTTCACACAGGAAACAGGATCTACCATGCTGCCGGCGCCGAAAAACCTGGTTGTTTCTCGCGTTACCGAAGA
CTCTGCGCGTCTGTCTTGGACCGCGCCGGACGCGGCGTTCGACTCTTTCCTGATCCAGTACCAGGAATCTGAAAAAGTTGGTGAAGCGA
TCGTGCTGACCGTTCCGGGTTCTGAACGTTCTTACGACCTGACCGGTCTGAAACCGGGTACCGAATACACCGTTTCTATCTACGGTGTT
NNNNNNNNNNNNNNNNNNNNNNNNNNNNNTCTAACCCGCTGTCTGCGATCTTCACCACCGGCGGTCACCATCACCATCACCATGGCAGCGG
TTCTAGTCTAGCGGCCGCAACTGATCTTGGC

SEQ ID NO: 30 = FG8
GTGACACGGCGGTTAGAACGCGGCTACAATTAATACATAACCCCATCCCCCTGTTGACAATTAATCATCGGCTCGTATAATGTGTGGAA
TTGTGAGCGGATAACAATTTCACACAGGAAACAGGATCTACCATGCTGCCGGCGCCGAAAAACCTGGTTGTTTCTCGCGTTACCGAAGA
CTCTGCGCGTCTGTCTTGGACCGCGCCGGACGCGGCGTTCGACTCTTTCCTGATCCAGTACCAGGAATCTGAAAAAGTTGGTGAAGCGA
TCGTGCTGACCGTTCCGGGTTCTGAACGTTCTTACGACCTGACCGGTCTGAAACCGGGTACCGAATACACCGTTTCTATCTACGGTGTT
NNNNNNNNNNNNNNNNNNNNNNNNNNNNTCTAACCCGCTGTCTGCGATCTTCACCACCGGCGGTCACCATCACCATCACCATGGCAGCGGTTC
TAGTCTAGCGGCCGCAACTGATCTTGGC

SEQ ID NO: 31 = FG7
GTGACACGGCGGTTAGAACGCGGCTACAATTAATACATAACCCCATCCCCCTGTTGACAATTAATCATCGGCTCGTATAATGTGTGGAA
TTGTGAGCGGATAACAATTTCACACAGGAAACAGGATCTACCATGCTGCCGGCGCCGAAAAACCTGGTTGTTTCTCGCGTTACCGAAGA
CTCTGCGCGTCTGTCTTGGACCGCGCCGGACGCGGCGTTCGACTCTTTCCTGATCCAGTACCAGGAATCTGAAAAAGTTGGTGAAGCGA
TCGTGCTGACCGTTCCGGGTTCTGAACGTTCTTACGACCTGACCGGTCTGAAACCGGGTACCGAATACACCGTTTCTATCTACGGTGTT
NNNNNNNNNNNNNNNNNNNNNNNNNNTCTAACCCGCTGTCTGCGATCTTCACCACCGGCGGTCACCATCACCATCACCATGGCAGCGGTTCTAG
TCTAGCGGCCGCAACTGATCTTGGC

SEQ ID NO: 32 FG loop of Tencon
KGGHRSN

SEQ ID NO: 33 = Tcon 6
AAGAAGGAGAACCGGTATGCTGCCGGCGCCGAAAAAC

SEQ ID NO: 34 = Tcon5E86Ishort
GAG CCG CCG CCA CCG GTT TAA TGG TGA TGG TGA TGG TGA CCA CCG GTG GTG AAG ATC GCA GAC AG SEQ ID NO: 35 Original tencon C-strand
sfliqyqe SEQ ID NO: 36 ALB-E05 C-strand
sfQiEyWe SEQ ID NO: 37 = ALB-E07 C-strand
sfKiLyEe SEQ ID NO: 38 = ALB-H9 C-strand SEQ ID NO: 39 = Original tencon CD-loop
sekvge SEQ ID NO: 40 = ALB-E05 CD-loop
DDVGge SEQ ID NO: 41 = ALB-E07 CD-loop
YLVFge SEQ ID NO: 42 = ALB-H9 CD-loop
QSIVge SEQ ID NO: 43 Original tencon F-strand
eytvsiygvk SEQ ID NO: 44 ALB-E05 F-strand
eyDvYiLgvk SEQ ID NO: 45 ALB-E07 F-strand
eyWvAiWgvk

| Sequence information |
|---|
| SEQ ID NO: 46 ALB-H9 F-strand<br>eyRvWiYgvk |
| SEQ ID NO: 47 Original tencon FG-loop<br>gghrsnp |
| SEQ ID NO: 48 ALB-E05 FG-loop<br>ggWEsGP |
| SEQ ID NO: 49 ALB-E07 FG-loop<br>ggQVsGT |
| SEQ ID NO: 50 ALB-H9 FG-loop<br>ggNDsWP |
| B7-SEQ ID NO: 51<br>MLPAPKNLVASRVTEDSARLSWTAPDAAFDSFNIAYWEPGIGGEAIWLRVPGSERSYDLTGLKPGTEYKVWIHGVKGGASSPPLIARFT<br>T |
| A10V SEQ ID NO: 52<br>MLPAPKNLVVSRVTEDSARLSWTAPDAAFDSFNIAYWEPGIGGEAIWLRVPGSERSYDLTGLKPGTEYKVWIHGVKGGASSPPLIARFT<br>T |
| A10V, N33A SEQ ID NO: 53<br>MLPAPKNLVVSRVTEDSARLSWTAPDAAFDSFAIAYWEPGIGGEAIWLRVPGSERSYDLTGLKPGTEYKVWIHGVKGGASSPPLIARFT<br>T |
| A10V, A35S SEQ ID NO: 54<br>MLPAPKNLVVSRVTEDSARLSWTAPDAAFDSFNISYWEPGIGGEAIWLRVPGSERSYDLTGLKPGTEYKVWIHGVKGGASSPPLIARFT<br>T |
| A10V, W37A SEQ ID NO: 55<br>MLPAPKNLVVSRVTEDSARLSWTAPDAAFDSFNIAYAEPGIGGEAIWLRVPGSERSYDLTGLKPGTEYKVWIHGVKGGASSPPLIARFT<br>T |
| A10V, P39A SEQ ID NO: 56<br>MLPAPKNLVVSRVTEDSARLSWTAPDAAFDSFNIAYWEAGIGGEAIWLRVPGSERSYDLTGLKPGTEYKVWIHGVKGGASSPPLIARFT<br>T |
| A10V, G40A SEQ ID NO: 57<br>MLPAPKNLVVSRVTEDSARLSWTAPDAAFDSFNIAYWEPAIGGEAIWLRVPGSERSYDLTGLKPGTEYKVWIHGVKGGASSPPLIARFT<br>T |
| A10V, I41A SEQ ID NO: 58<br>MLPAPKNLVVSRVTEDSARLSWTAPDAAFDSFNIAYWEPGAGGEAIWLRVPGSERSYDLTGLKPGTEYKVWIHGVKGGASSPPLIARFT<br>T |
| A10V, G42A SEQ ID NO: 59<br>MLPAPKNLVVSRVTEDSARLSWTAPDAAFDSFNIAYWEPGIAGEAIWLRVPGSERSYDLTGLKPGTEYKVWIHGVKGGASSPPLIARFT<br>T |
| A10V, W47A SEQ ID NO: 60<br>MLPAPKNLVVSRVTEDSARLSWTAPDAAFDSFNIAYWEPGIGGEAIALRVPGSERSYDLTGLKPGTEYKVWIHGVKGGASSPPLIARFT<br>T |
| A10V, R49A SEQ ID NO: 61<br>MLPAPKNLVVSRVTEDSARLSWTAPDAAFDSFNIAYWEPGIGGEAIWLAVPGSERSYDLTGLKPGTEYKVWIHGVKGGASSPPLIARFT<br>T |
| A10V, K69A SEQ ID NO: 62<br>MLPAPKNLVVSRVTEDSARLSWTAPDAAFDSFNIAYWEPGIGGEAIWLRVPGSERSYDLTGLKPGTEYAVWIHGVKGGASSPPLIARFT<br>T |
| A10V, W71A SEQ ID NO: 63<br>MLPAPKNLVVSRVTEDSARLSWTAPDAAFDSFNIAYWEPGIGGEAIWLRVPGSERSYDLTGLKPGTEYKVAIHGVKGGASSPPLIARFT<br>T |
| A10V, H73A SEQ ID NO: 64<br>MLPAPKNLVVSRVTEDSARLSWTAPDAAFDSFNIAYWEPGIGGEAIWLRVPGSERSYDLTGLKPGTEYKVWIAGVKGGASSPPLIARFT<br>T |
| A10V, A79S SEQ ID NO: 65<br>MLPAPKNLVVSRVTEDSARLSWTAPDAAFDSFNIAYWEPGIGGEAIWLRVPGSERSYDLTGLKPGTEYKVWIHGVKGGSSSPPLIARFT<br>T |

-continued

| Sequence information |
|---|

A10V, S80A SEQ ID NO: 66
MLPAPKNLVVSRVTEDSARLSWTAPDAAFDSFNIAYWEPGIGGEAIWLRVPGSERSYDLTGLKPGTEYKVWIHGVKGGAASPPLIARFT
T

A10V, P82A SEQ ID NO: 67
MLPAPKNLVVSRVTEDSARLSWTAPDAAFDSFNIAYWEPGIGGEAIWLRVPGSERSYDLTGLKPGTEYKVWIHGVKGGASSAPLIARFT
T

A10V, I85A SEQ ID NO: 68
MLPAPKNLVVSRVTEDSARLSWTAPDAAFDSFNIAYWEPGIGGEAIWLRVPGSERSYDLTGLKPGTEYKVWIHGVKGGASSPPLAARFT
T

A10V, R87A SEQ ID NO: 69
MLPAPKNLVVSRVTEDSARLSWTAPDAAFDSFNIAYWEPGIGGEAIWLRVPGSERSYDLTGLKPGTEYKVWIHGVKGGASSPPLIAAFT
T

SEQ ID NO: 70 ALB-H9
LPAPKNLVVSRVTEDSARLSWTAPDAAFDSFHIEYWEQSIVGEAIVLTVPGSERSYDLTGLKPGTEYRVWIYGVKGGNDSWPLSAIFT
T

SEQ ID NO: 71 (GS)$_2$
GSGS

SEQ ID NO: 72 (GGGS)$_2$
GGGSGGGS

SEQ ID NO: 73 (GGGGS)$_2$
GGGGSGGGGSGGGGSGGGGSGGGGS

SEQ ID NO: 74 (AP)$_2$
APAP

SEQ ID NO: 75 (AP)$_5$
APAPAPAPAP

SEQ ID NO: 76 (AP)$_{10}$
APAPAPAPAPAPAPAPAPAP

SEQ ID NO: 77 (AP)$_{20}$
APAPAPAPAPAPAPAPAPAPAPAPAPAPAPAPAPAPAPAP

SEQ ID NO: 78 A(EAAAK)$_5$AAA
AEAAAKEAAAKEAAAKEAAAKEAAAKAAA

SEQ ID NO: 79 Human Serum Albumin
KWVTFISLLFLFSSAYSRGVFRRDAHKSEVAHRFKDLGEENFKALVLIAFAQYLQQCPFEDHVKLVNEVTEFAKTCVADESAENCDKSL
HTLFGDKLCTVATLRETYGEMADCCAKQEPERNECFLQHKDDNPNLPRLVRPEVDVMCTAFHDNEETFLKKYLYEIARRHPYFYAPELL
FFAKRYKAAFTECCQAADKAACLLPKLDELRDEGKASSAKQRLKCASLQKFGERAFKAWAVARLSQRFPKAEFAEVSKLVTDLTKVHTE
CCHGDLLECADDRADLAKYICENQDSISSKLKECCEKPLLEKSHCIAEVENDEMPADLPSLAADFVESKDVCKNYAEAKDVFLGMFLYE
YARRHPDYSVVLLLRLAKTYETTLEKCCAAADPHECYAKVFDEFKPLVEEPQNLIKQNCELFEQLGEYKFQNALLVRYTKKVPQVSTPT
LVEVSRNLGKVGSKCCKHPEAKRMPCAEDYLSVVLNQLCVLHEKTPVSDRVTKCCTESLVNRRPCFSALEVDETYVPKEFNAETFTFHA
DICTLSEKERQIKKQTALVELVKHKPKATKEQLKAVMDDFAAFVEKCCKADDKETCFAEEGKKLVAASQAALGL SEQ ID NO: 80 Cynomolgus Serum Albumin
KWVTFISLLFLFSSAYSRGVFRRDTHKSEVAHRFKDLGEEHFKGLVLVAFSQYLQQCPFEEHVKLVNEVTEFAKTCVADESAENCDKSL
HTLFGDKLCTVATLRETYGEMADCCAKQEPERNECFLQHKDDNPNLPPLVRPEVDVMCTAFHDNEATFLKKYLYEVARRHPYFYAPELL
FFAARYKAAFAECCQAADKAACLLPKLDELRDEGKASSAKQRLKCASLQKFGDRAFKAWAVARLSQKFPKAEFAEVSKLVTDLTKVHTE
CCHGDLLECADDRADLAKYMCENQDSISSKLKECCDKPLLEKSHCLAEVENDEMPADLPSLAADYVESKDVCKNYAEAKDVFLGMFLYE
YARRHPDYSVMLLLRLAKAYEATLEKCCAAADPHECYAKVFDEFQPLVEEPQNLVKQNCELFEQLGEYKFQNALLVRYTKKVPQVSTPT
LVEVSRNLGKVGAKCCKLPEAKRMPCAEDYLSVVLNRLCVLHEKTPVSEKVTKCCTESLVNRRPCFSALELDEAYVPKAFNAETFTFHA
DMCTLSEKEKQVKKQTALVELVKHKPKATKEQLKGVMDNFAAFVEKCCKADDKEACFAEEGPKFVAASQAALA SEQ ID NO: 81 Tenascin C (TN3)
DAPSQIEVKDVTDTTALITWFKPLAEIDGIELTYGIKDVPGDRTTIDLTEDENQYSIGNLKPDTEYEVSLISRRGDMSSNPAKETFTT SEQ ID NO: 82 Fibcon
LDAPTDLQVTNVTDTSITVSWTPPSATITGYRITYTPSNGPGEPKELTVPPSSTSVTITGLTPGVEYVVSLYALKDNQESPPLVGTQTT SEQ ID NO: 83 FN10
VSDVPRDLEVVAATPTSLLISWDAPAVTVRYYRITYGETGGNSPVQEFTVPGSKSTATISGLKPGVDYTITVYAVTGRGDSPASSKPIS
INYRT

What is claimed is:

1. A protein comprising an amino acid sequence that is at least 85% identical to an amino acid sequence selected from the group consisting of SEQ ID NO: 51, 52, 53, 54, 55, 56, 57, 58, 59, 60, 61, 62, 63, 64, 65, 66, 67, 68, and 69.

2. The protein of claim 1, wherein the protein comprises a substitution at a position that corresponds to residue position 10 of SEQ ID NO: 51.

3. The protein of claim 2, wherein the substitution is selected from the group consisting of A10V, A10G, A10L, A10I, A10T, and A10S.

4. The protein of claim 1, wherein the protein comprises a substitution selected from A10V, N33A, A35S, W37A, P39A, G40A, I41A, G42A, W47A, R49A, K69A, W71A, H73A, A79S, S80A, P82A, I85A, R87A, or combinations thereof, corresponding to SEQ ID NO: 51.

5. The protein of claim 1, wherein the protein comprises a substitution at a position selected from 10, 33, 25, 37, 39, 40, 41, 42, 47, 49, 69, 71, 73, 79, 80, 82, 85, 87, or combinations thereof, of SEQ ID NO: 51.

6. The protein of claim 1, wherein the protein is linked to another molecule.

7. The protein of claim 6, wherein the another molecule is a drug, a protein, an antibody, a polymer, or a toxin.

8. The protein of claim 6, wherein the another molecule is a FN3 domain that binds to a molecule other than human albumin.

9. The protein of claim 8, wherein the FN3 domain binds to CD71.

10. The protein of claim 6, wherein the protein is linked through a linker to the another molecule.

11. The protein of claim 10, wherein the linker is a peptide linker comprising a sequence selected from $(GS)_2$, (SEQ ID NO: 71), $(GGGS)_2$ (SEQ ID NO: 72), $(GGGGS)_5$ (SEQ ID NO: 73), $(AP)_2$ (SEQ ID NO: 74), $(AP)_5$ (SEQ ID NO: 75), $(AP)_{10}$ (SEQ ID NO: 76), $(AP)_{20}$ (SEQ ID NO: 77) or A $(EAAAK)_5AAA$ (SEQ ID NO: 78).

12. The protein of claim 1, wherein the protein comprises an amino acid sequence that is at least 90% identical to an amino acid sequence selected from the group consisting of SEQ ID NO: 51, 52, 53, 54, 55, 56, 57, 58, 59, 60, 61, 62, 63, 64, 65, 66, 67, 68, and 69.

13. The protein of claim 1, wherein the protein comprises an amino acid sequence that is at least 95% identical to an amino acid sequence selected from the group consisting of SEQ ID NO: 51, 52, 53, 54, 55, 56, 57, 58, 59, 60, 61, 62, 63, 64, 65, 66, 67, 68, and 69.

14. The protein of claim 13, wherein the protein comprises a cysteine substitution in at least one residue position selected from 6, 11, 22, 25, 26, 52, 53, 61, 88, or combinations thereof, corresponding to the residue positions of SEQ ID NO: 1.

15. The protein of claim 13, wherein the protein comprises a cysteine at the N and/or C-terminus of the protein.

16. The protein of claim 13, wherein the protein is linked to another molecule.

17. The protein of claim 16, wherein the another molecule is a drug, a protein, an antibody, a polymer, a toxin, or a FN3 domain that binds to a molecule other than human albumin.

18. The protein of claim 17, wherein the FN3 domain binds to CD71.

19. The protein of claim 16, wherein the protein is linked through a linker to the another molecule, and wherein the linker is a peptide linker comprising a sequence selected from $(GS)_2$, (SEQ ID NO: 71), $(GGGS)_2$ (SEQ ID NO: 72), $(GGGGS)_5$ (SEQ ID NO: 73), $(AP)_2$ (SEQ ID NO: 74), $(AP)_5$ (SEQ ID NO: 75), $(AP)_{10}$ (SEQ ID NO: 76), $(AP)_{20}$ (SEQ ID NO: 77) or A $(EAAAK)_5AAA$ (SEQ ID NO: 78).

20. The protein of claim 1, wherein the protein comprises an amino acid sequence that is at least 95% identical to the amino acid sequence of SEQ ID NO: 51.

21. The protein of claim 1, wherein the protein comprises an amino acid sequence that is at least 98% identical to SEQ ID NO: 51.

22. The protein of claim 21, wherein the protein comprises a cysteine substitution in at least one residue position selected from 6, 11, 22, 25, 26, 52, 53, 61, 88, or combinations thereof, corresponding to the residue positions of SEQ ID NO: 1.

23. The protein of claim 1, wherein the protein comprises an amino acid sequence that is at least 98% identical to an amino acid sequence selected from the group consisting of SEQ ID NO: 51, 52, 53, 54, 55, 56, 57, 58, 59, 60, 61, 62, 63, 64, 65, 66, 67, 68, and 69.

24. The protein of claim 23, wherein the protein comprises a cysteine substitution in at least one residue position selected from 6, 11, 22, 25, 26, 52, 53, 61, 88, or combinations thereof, corresponding to the residue positions of SEQ ID NO: 1.

25. The protein of claim 23, wherein the protein is linked to another molecule.

26. The protein of claim 25, wherein the another molecule is a drug, a protein, an antibody, a polymer, a toxin, or a FN3 domain that binds to a molecule other than human albumin.

27. The protein of claim 26, wherein the FN3 domain binds to CD71.

28. The protein of claim 25, wherein the protein is linked through a linker to the another molecule, and wherein the linker is a peptide linker comprising a sequence selected from $(GS)_2$, (SEQ ID NO: 71), $(GGGS)_2$ (SEQ ID NO: 72), $(GGGGS)_5$ (SEQ ID NO: 73), $(AP)_2$ (SEQ ID NO: 74), $(AP)_5$ (SEQ ID NO: 75), $(AP)_{10}$ (SEQ ID NO: 76), $(AP)_{20}$ (SEQ ID NO: 77) or A $(EAAAK)_5AAA$ (SEQ ID NO: 78).

29. A protein comprising an amino acid sequence selected from the group consisting of SEQ ID NO: 51, 52, 53, 54, 55, 56, 57, 58, 59, 60, 61, 62, 63, 64, 65, 66, 67, 68, and 69.

30. A protein comprising the amino acid sequence of SEQ ID NO: 51.

31. The protein of claim 29, wherein the protein is linked to another molecule.

32. The protein of claim 31, wherein the another molecule is a drug, a protein, an antibody, a polymer, a toxin, or a FN3 domain that binds to a molecule other than human albumin.

33. The protein of claim 32, wherein the FN3 domain binds to CD71.

34. The protein of claim 31, wherein the protein is linked through a linker to the another molecule, and wherein the linker is a peptide linker comprising a sequence selected from $(GS)_2$, (SEQ ID NO: 71), $(GGGS)_2$ (SEQ ID NO: 72), $(GGGGS)_5$ (SEQ ID NO: 73), $(AP)_2$ (SEQ ID NO: 74), $(AP)_5$ (SEQ ID NO: 75), $(AP)_{10}$ (SEQ ID NO: 76), $(AP)_{20}$ (SEQ ID NO: 77) or A $(EAAAK)_5AAA$ (SEQ ID NO: 78).

35. An isolated polynucleotide encoding the proteins of claim 1.

36. A vector comprising the polynucleotide of claim 35.

37. An isolated host cell comprising the vector of claim 36.

38. A pharmaceutical composition comprising the protein of claim 13 and a pharmaceutically acceptable carrier.

* * * * *